US008431393B2

(12) United States Patent
Kim et al.

(10) Patent No.: US 8,431,393 B2
(45) Date of Patent: *Apr. 30, 2013

(54) AIMP2-DX2 GENE AND ITS USES

(75) Inventors: Sunghoon Kim, Seoul (KR); Jin Woo Choi, Seoul (KR)

(73) Assignee: Neomics Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/011,174

(22) Filed: Jan. 21, 2011

(65) Prior Publication Data

US 2011/0136119 A1    Jun. 9, 2011

Related U.S. Application Data

(60) Division of application No. 12/255,943, filed on Oct. 22, 2008, now Pat. No. 8,003,780, which is a continuation-in-part of application No. 11/264,725, filed on Nov. 1, 2005, now Pat. No. 7,459,529.

(30) Foreign Application Priority Data

Nov. 24, 2004 (KR) ......................... 10-2004-0097164
May 10, 2005 (KR) ......................... 10-2005-0039073

(51) Int. Cl.
*C07H 21/04* (2006.01)
*C07K 1/00* (2006.01)
*C12N 15/00* (2006.01)
*C12N 5/00* (2006.01)

(52) U.S. Cl.
USPC ...... 435/320.1; 530/350; 536/23.1; 536/23.5; 435/325

(58) Field of Classification Search ............... 435/320.1, 435/325; 530/350; 536/23.1, 23.5
See application file for complete search history.

(56) References Cited

U.S. PATENT DOCUMENTS

| | | | |
|---|---|---|---|
| 7,070,940 | B2 | 7/2006 | Corti et al. |
| 7,459,529 | B2 | 12/2008 | Kim et al. |
| 2004/0175375 | A1 | 9/2004 | Kim et al. |
| 2005/0239731 | A1 | 10/2005 | McSwiggen et al. |
| 2006/0110397 | A1 | 5/2006 | Kim et al. |
| 2007/0031844 | A1 | 2/2007 | Khvorova et al. |
| 2008/0044439 | A1 | 2/2008 | David |
| 2008/0199426 | A1 | 8/2008 | Sukhatme et al. |
| 2009/0156536 | A1 | 6/2009 | Kim et al. |

FOREIGN PATENT DOCUMENTS

EP         1454628     *  9/2004

OTHER PUBLICATIONS

Sambrook et al (Molecular Cloning, A Laboratory Manual, Cold Spring Harbor, 1989, pp. p. 16.3-4.).*
U.S. Appl. No. 13/011,386, filed Jan. 21, 2011, Sunghoon Kim et al.
Kim et al., "Downregulation of Fuse-Binding Protein and c-myc by tRNA Synthetase Cofactor p38 is Required for Lung Cell Differentiation," Nat. Genet. 34:330-336, 2003.
Tuschl et al., "The siRNA User Guideline: Selection of siRNA Duplexes form the Target mRNA Sequence," pp. 1-7, 2004.
U.S. Appl. No. 11/264,725, Prosecution Table of Contents from PAIR dated May 5, 2009.
U.S. Appl. No. 11/264,725, Notice to File Corrected Application Papers dated Nov. 25, 2005.
U.S. Appl. No. 11/264,725, Reply to Notice to File Corrected Application Papers filed Dec. 9, 2005.
U.S. Appl. No. 11/264,725, Restriction Requirement dated Nov. 14, 2006.
U.S. Appl. No. 11/264,725, Reply to Restriction Requirement filed Dec. 13, 2006.
U.S. Appl. No. 11/264,725, Office Action dated Feb. 8, 2007.
U.S. Appl. No. 11/264,725, Reply to Office Action filed Jun. 8, 2007.
U.S. Appl. No. 11/264,725, Final Office Action dated Sep. 7, 2007.
U.S. Appl. No. 11/264,725, Reply to Final Office Action, Declaration, Notice of Appeal, and Sequence Listing filed Mar. 7, 2008.
U.S. Appl. No. 11/264,725, Advisory Action dated Apr. 8, 2008.
U.S. Appl. No. 11/264,725, Reply to Office Action filed May 16, 2008.
U.S. Appl. No. 11/264,725, Notice of Allowance, Notice of Allowability, and Examiner's Amendment dated Aug. 6, 2008.
U.S. Appl. No. 11/264,725, Issue Fee Payment and Reply to Notice of Allowance filed Oct. 29, 2008.
U.S. Appl. No. 12/255,943, Table of Contents from PAIR dated Mar. 28, 2011.
U.S. Appl. No. 12/255,943, Sequence Requirement dated Dec. 11, 2008.
U.S. Appl. No. 12/255,943, Reply to Sequence Requirement filed Feb. 11, 2009.
U.S. Appl. No. 12/255,943, Information Disclosure Statement filed Feb. 19, 2009.
U.S. Appl. No. 12/255,943, Information Disclosure Statement filed Jun. 8, 2009.
U.S. Appl. No. 12/255,943, Restriction Requirement dated Nov. 18, 2009.
U.S. Appl. No. 12/255,943, Reply to Restriction Required filed Jan. 19, 2010.
U.S. Appl. No. 12/255,943, Reply to Restriction Requirement (resubmission) filed Mar. 31, 2010.
U.S. Appl. No. 12/255,943, Examiner Interview Summary dated Apr. 6, 2010.
U.S. Appl. No. 12/255,943, Office Action dated Apr. 19, 2010.
U.S. Appl. No. 12/255,943, Reply to Office Action dated Jul. 19, 2010.
U.S. Appl. No. 12/255,943, Examiner Interview Summary dated Sep. 8, 2010.
U.S. Appl. No. 12/255,943, Final Office Action dated Sep. 21, 2010.
U.S. Appl. No. 12/255,943, Reply to Office Action filed Jan. 21, 2010.
U.S. Appl. No. 12/255,943, Ex Parte Quayle Action dated Feb. 7, 2011.

* cited by examiner

*Primary Examiner* — Stephen Rawlings
*Assistant Examiner* — Yan Xiao
(74) *Attorney, Agent, or Firm* — Clark & Elbing LLP

(57) ABSTRACT

The present invention relates to a variant of AIMP2 lacking exon 2 gene, named as AIMP2-DX2 gene, which is specifically expressed in cancer cells. The AIMP2-DX2 gene and siRNA targeting AIMP2-DX2 can be successfully used in the development of diagnosis and treatment of cancer.

4 Claims, 40 Drawing Sheets

AIMP2 Genomic DNA

RT primer: CAGCACCACGTCTGC

Primers for exon 1-3
1: TCTGACGGTTTCTGAGCGTT
5: AAGTGAATCCCAGCTGATAG

Primers for exon3-4
6: AGTGCTTTGGAGAACAGAAT
7: AAGAGCAGAGTTCATGGAGC

Primers for AIMP2-DX2
DX2-F: CGT AAT CCT GCA CGT GGC CAG
DX2-B: TGC TTT GGT TCT GCC ATG CCG

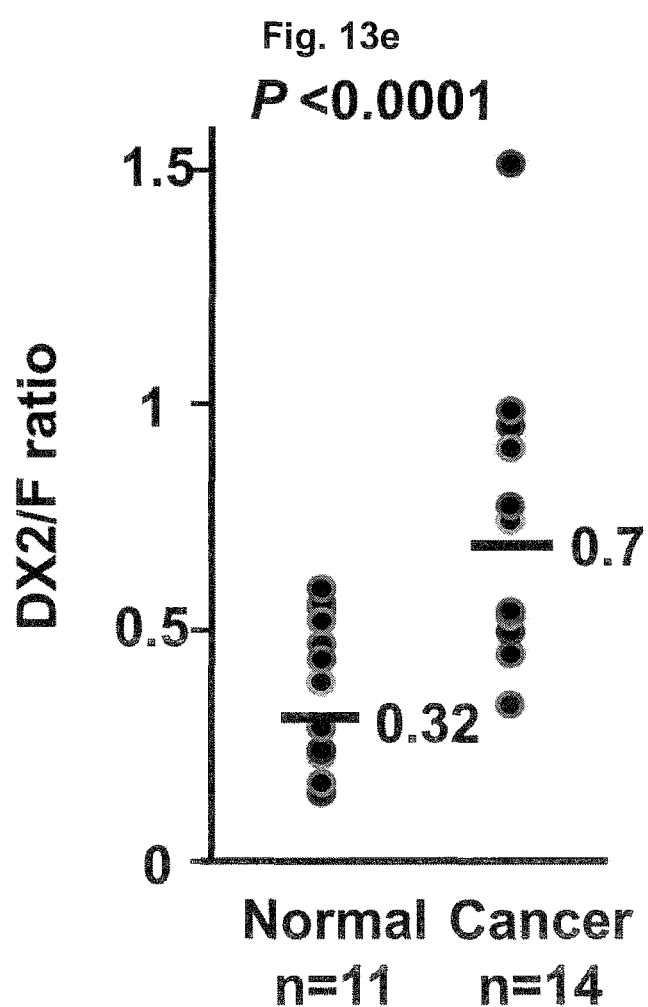

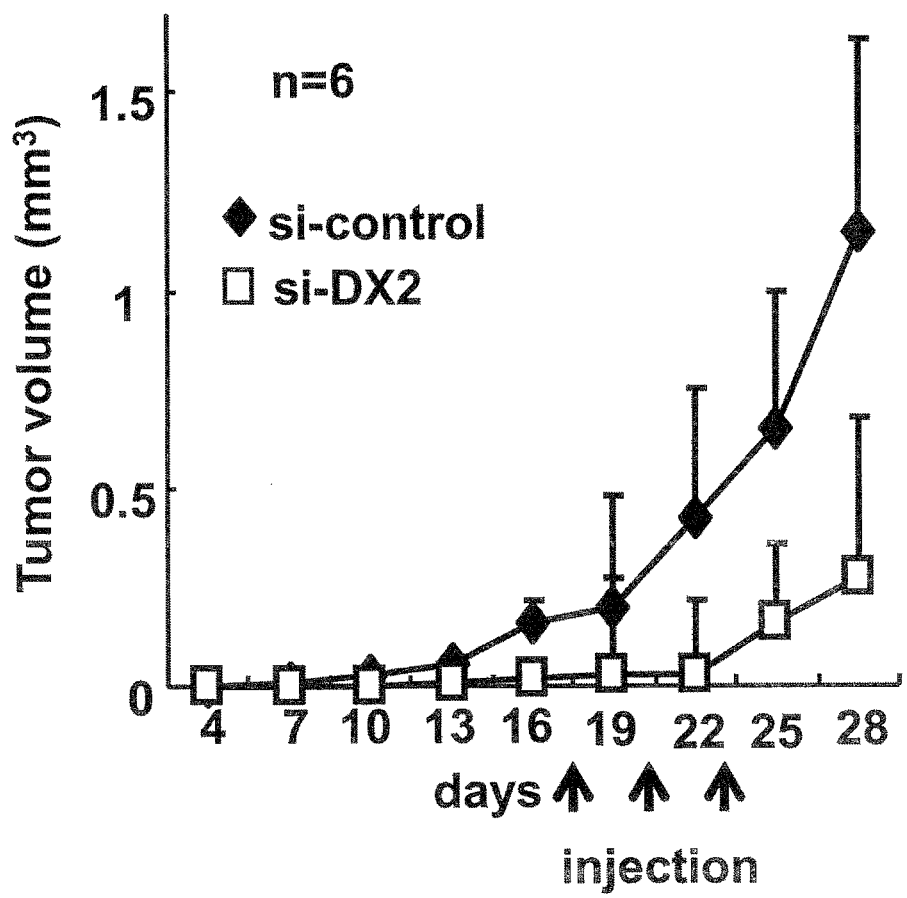

si-cont si-DX2

Carrier | GFP vector

SUV mean

|  | before treatment | 8 weeks after treatment |
|---|---|---|
| EV-treated #1 | 0.456 | 1.812 |
| EV-treated #2 | 0.585 | 1.434 |
| shDX2-treated #1 | 0.510 | 1.106 |
| shDX2-treated #2 | 0.423 | 0.657 |

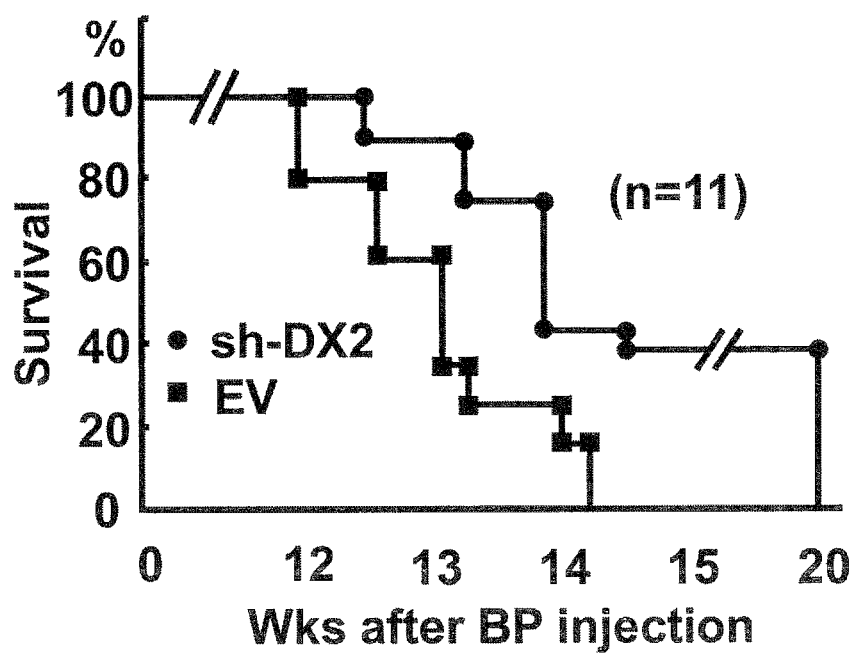

AIMP2-DX2 GENE AND ITS USES

CROSS-REFERENCE TO RELATED APPLICATIONS

This application is a divisional of, and claims priority from, U.S. patent application Ser. No. 12/255,943, filed Oct. 22, 2008, which is a continuation-in-part of U.S. Ser. No. 11/264, 725, filed Nov. 1, 2005, which claims priority from Korean Patent Application Nos. 10-2004-0097164 and 10-2005-0039073, filed Nov. 24, 2004 and May 10, 2005, respectively in the Korean Intellectual Property Office. The disclosures of the priority applications, including the sequence listings and tables submitted in electronic form in lieu of paper, are incorporated by reference into the instant specification.

BACKGROUND OF THE INVENTION

1. Field of the Invention

The present invention relates to a variant of AIMP2 lacking exon 2, named as AIMP2-DX2 gene and SiRNA targeting AIMP2-DX2.

2. Description of the Related Art

Cancer is generally diagnosed by radiography examinations such as X-ray radiography, computed tomography and bronchography or bronchoscopy examination. However, such methods provide no diagnostic data in terms of cell physiology molecular genetics, while they allow to determine anatomical progress of cancer. Lung and liver cancers are known to exhibit high incidence rate and mortality over the world.

To overcome shortcomings of such conventional examination technologies, a number of markers have been suggested for diagnosing lung or liver cancer as described hereunder:

Korean Pat. Appln. No. 10-1998-0038212 relating to the process for evaluating metastasis of lung cancer discloses that local metastatic lung cancer may be assessed by measuring the expression of mitogen activated protein kinase phosphatase-1 (MKP-1) in lung tissues. WO 2004/005891 suggests various diagnostic markers for lung cancer such as AOE372, ATP5D, B4GALT, Ppase, GRP58, GSTM4, P4HB, TPI and UCHL1. Monoclonal antibodies to LCGA have been proposed to diagnose and treat non-small cell lung carcinoma and ovary cancer as described in U.S. Pat. No. 6,117,981. EP 0804451 discloses a method for diagnosing and treating lung cancer by use of lung cancer-specific antigen HCAVIII. In addition, U.S. Pat. Nos. 6,746,846 and 6,737,514 and EP 0621480 also discuss lung cancer markers.

Korean Pat. Appln. No. 10-2000-0040609 discloses the early detection method for liver diseases including liver cirrhosis and cancer by measuring the level of asialo-glycoproteins in accordance with sandwich assay in which lectins serve as a capture protein and/or probe protein. Korean Pat. Appln. No. 10-2002-0035260 describes that compositions comprising long-chain fatty-acid-Coenzyme A ligase 4, farnesyl diphosphate synthase, syndecan 2, emopamil-binding protein, preferentially expressed antigen in melanoma and histidine ammonia-lyase are useful in diagnosing human liver cancer. EP 0334962 suggests that the comparison of level of UDP-N-acetyglucosamine with that of glycoprotein N-acetylglucosamine transferase permits to detect liver cancer. Furthermore, EP 0339097 discloses diagnostic methods for liver cancer by measuring the level of inhibitors of collagenase in serum, plasma or synovia in a sandwich assay format.

However, markers for lung and liver cancers so far proposed permit restricted application in the senses that they are also detectable in normal cells. Therefore, assays or diagnostics using such markers are generally carried out by comparing their expression levels in normal and cancerous cells, resulting in unreliable and erroneous diagnosis.

Accordingly, there remains a need to propose novel diagnostic makers for lung or live cancer.

Throughout this application, several patents and publications are referenced and citations are provided in parentheses. The disclosure of these patents and publications is incorporated into this application in order to more fully describe this invention and the state of the art to which this invention pertains.

SUMMARY OF THE INVENTION

Under such circumstances, the present inventors have made intensive research to develop a novel cancer-specific molecular species and a result, found that a variant of AIMP2 lacking exon 2, AIMP2-DX2 is specifically expressed in cancer cells not normal cells and permits to diagnose cancer occurrence in more reliable manner. In addition, the present inventors have discovered that antibody, siRNA and antisense oligonucleotide specific to AIMP2-DX2 allow to effectively treat cancer.

Accordingly, it is an object of this invention to provide a AIMP2-DX2 protein with deleted exon 2 region of AIMP2.

It is another object of this invention to provide a nucleic acid molecule comprising a nucleotide sequence encoding the AIMP2-DX2 protein.

It is still another object of this invention to provide a recombinant vector carrying a nucleotide sequence encoding the AIMP2-DX2 protein.

It is further object of this invention to provide a transformant which is transformed with the recombinant vector carrying a nucleotide sequence encoding the AIMP2-DX2 protein.

It is still further object of this invention to provide an antibody against the AIMP2-DX2 protein.

It is another object of this invention to provide a diagnostic kit for cancer comprising an antibody specific to the AIMP2-DX2 protein.

It is still another object of this invention to provide a method for diagnosing cancer.

It is further object of this invention to provide an antisense oligonucleotide which is complementary to a region of an mRNA of the AIMP2-DX2 protein.

It is still further object of this invention to provide a pharmaceutical composition for treating cancer.

It is another object of this invention to provide a method of screening for an agent which inhibits the formation of a heterodimer between the AIMP2-DX2 protein and the AIMP2 protein.

It is still another object of this invention to a method of screening for an agent which inhibits the expression of the AIMP2-DX2 gene.

It is another object of this invention to an isolated siRNA (small interfering RNA) molecule comprising a sense region and an antisense region that down regulates expression of an AIMP2-DX2 gene via RNA interference (RNAi), wherein each strand of the siRNA molecules is independently about 18 to about 28 nucleotides in length, wherein one strand of the siRNA molecule comprises nucleotide sequence having sufficient complementarity to an RNA of the AIMP2-DX2 gene for the siRNA molecule to direct cleavage of the RNA via RNA interference.

It is still another object of this invention to a recombinant nucleic acid construct comprising a nucleic acid that is capable of directing transcription of a small interfering RNA (siRNA), the nucleic acid comprising: (a) at least one promoter; (b) a DNA polynucleotide segment that is operably linked to the promoter, the segment comprising nucleotide sequence having sufficient complementarity to an RNA of the AIMP2-DX2 gene for the siRNA molecule to direct cleavage of the RNA via RNA interference; (c) a linker sequence comprising at least 4 nucleotides operably linked to the DNA polynucleotide segment of (b); and (d) operably linked to the linker sequence a second polynucleotide of at least 18 nucleotides that is complementary to the segment of (b).

Other objects and advantages of the present invention will become apparent from the detailed description to follow taken in conjugation with the appended claims and drawings.

BRIEF DESCRIPTION OF THE DRAWINGS

In FIG. 1a, the cells were incubated with the indicated concentrations (0, 2 and 4 ng/ml) of TGF-β1 for 6 hr. Thymidine incorporation in the untreated cells was taken as 1 and the values are the averages of four independent experiments. In FIG. 1b, AIMP2$^{+/+}$ and AIMP2$^{-/-}$ MEFs (14.5 day) were cultivated in the presence of TGF-β (2 ng/ml) for 4 day, fixed with paraformaldehyde, and the colonies were visualized by Giemsa staining. In FIG. 1c, MEFs were treated with TGF-β for 24 hr, and the portion of G0/G1 phase cells was determined by flow cytometry (FACS caliubur, Becton Dickinson, US). In FIG. 1d, MEFs were treated with TGF-β (2 ng/ml) for 1 hr. Smad2 and Smad3 were reacted with their specific antibodies and visualized by FITC-conjugated antibody (green). Nuclei were stained with PI (red). In FIG. 1e, the interactions of AIMP2 with Smad2 and Smad3 were tested by co-immunoprecipitation with antibodies against Smad2 and Smad3.

In FIG. 2a, A549 cells were harvested at the indicated times after treatment of TGF-β (2 ng/ml) and the extracted proteins were immunoprecipitated with anti-Smad2 or Smad3 antibody, and coprecipitation of AIMP2 was determined with anti-AIMP2 antibody. WCL stands for the Western blots of the proteins of whole cell lysates. In FIG. 2b, the expression of the TGF-β target genes, p15, p21 and PAI-1 was determined by RT-PCR in the control and AIMP2-transfected DU145. FIG. 2c demonstrates the effect of AIMP2 on the phosphorylation of Smad2 in AIMP2$^{-/-}$ MEFs. In FIG. 2d, the different domains of Smad2 (Mad-homology domain, MH1, MH2 and linker) were expressed as LexA fusion proteins and tested for the interaction with B42-fused AIMP2 by the blue colony formation on X-gal-containing yeast medium. In FIG. 2e, the TGF-β-dependent interaction of Smad2 with TGF-β receptor was determined by coimmunoprecipitation. MEFs were treated with TGF-β at 37° C. and incubated at 8° C. before immunoprecipitation. The association of TGF-β receptor with Smad2 was monitored by immunoblotting with anti-TβRI antibody (Santa Cruz biotech). FIG. 2f shows the time course of the total Smad2, phosphorylated Smad2 (p-Smad2), and AIMP2 levels in AIMP2$^{+/+}$ and AIMP2$^{-/-}$ MEFs after TGF-β treatment.

In FIG. 3b, "negative" indicates DU145 treated only with secondary antibody. 2000 cells were analyzed for each cell line. In FIG. 3c, the AIMP2 transcript level was compared by RT-PCR with different primer pairs. The transcripts spanning exons 3-4 and 1-3 were generated by the primer pairs of 6/7 and 1/5 (see FIG. 8b), respectively. GAPDH is a loading control. Note the generation of a smaller AIMP2 transcript from the primer pair for the transcript of exon 1-3. This smaller transcript is the alternative splicing form of AIMP2 lacking exon 2 (AIMP2-DX2). This transcript was produced only from the low-AIMP2 cell lines by RT-PCR with the primer AIMP2-DX2-F and the other one specific to the junction sequence between exon 1 and 3 (AIMP2-DX2-B) (see FIG. 8b). In FIG. 3d, TGF-β-dependent induction and nuclear translocation of AIMP2 were examined by immunofluorescence staining after the incubation with TGF-β for 2 hr. In FIG. 3e, the effect of TGF-β was compared on the proliferation of the indicated cells by [$^3$H] thymidine incorporation (n=4). In FIG. 3f, TGF-β-dependent induction of the target genes, p21 and PAI-1, was compared by RT-PCR after the incubation with TGF-β for 2 hr.

In FIG. 4a, AIMP2-DX2 was transfected into DU145 untreated or treated with TGF-β for 2 hr, and the AIMP2 level was determined by Western blotting. The expression of c-Myc, AIMP2-DX2 and GAPDH (control) was monitored by RT-PCR. In FIG. 4b, AIMP2-DX2 or empty vector was transfected into DU145, and its effect on the TGF-β-dependent cell growth inhibition was monitored by thymidine incorporation (n=4). In FIG. 4c, the interaction between AIMP2-F and AIMP2-DX2 was determined by yeast two hybrid assay as previously described (Rho, S. B. et al., PNAS. USA, 96:4488-93 (1999)). In FIG. 4d, AIMP2-F and AIMP2-DX2 were synthesized by in vitro translation in the presence of [$^{35}$S] methionine, mixed with either GST-AIMP2-F or -CDK2 (control), and precipitated with glutathione-Sepharose. The precipitated proteins were separated by SDS-PAGE and detected by autoradiography. In FIG. 4e, the interaction of AIMP2-F or AIMP2-DX2 with FUSE-binding protein (FBP; Kim, M. J. et al., Nat. Genet. 34:330-336: 2003)) and Smad2 was determined by yeast two hybrid assay. In FIG. 4f, the effect of the proteasome inhibitor, ALLN (50 μM for 4 hr) on the levels of the full-length (F) and AIMP2-DX2 of AIMP2 was monitored in the AIMP2-DX2-generating H322 cells by Western blotting with anti-AIMP2 antibody. The AIMP2-DX2 form was confirmed by its co-migration in gel with its in vitro synthesized counterpart. In FIG. 4g, the increase of AIMP2 by the treatment of ALLN (20 μM for 2 hr) was also shown by immunofluorescence staining with anti-AIMP2 antibody in H322 cells. In FIG. 4h, myc-tagged AIMP2-DX2 was transfected to DU145 that were treated with ALLN. Then, AIMP2 was immunoprecipitated with anti-AIMP2 antibody, and the ubiquitinated AIMP2 molecules were monitored by immunoblotting with anti-ubiquitin antibody (Ubi).

In FIG. 5a, AIMP2-DX2 (or empty vector) was transfected into MEFs and monitored its effect on cell growth. The cells and colonies were visualized by light microscopy (top) and Giemsa staining (bottom), respectively. In FIG. 5b, siRNA targeting AIMP2-DX2 (si-DX2) was introduced into H322 and its suppressive effect on the AIMP2-DX2 transcript was determined by RT-PCR (top). si-DX2 did not affect the full-length AIMP2 transcript as shown by RT-PCR of the transcript for exon 3-4. The effect of si-DX2 on the phosphorylation of Smad2 and AIMP2 expression was also determined by Western blotting (bottom). The effect of si-DX2 on the restoration of the TGF-β signaling was also determined by immunofluorescence staining of p-Smad2 (FIG. 5c), TGF-β-dependent reporter assay under 3TP promoter (FIG. 5d) and growth arrest (FIG. 5e) using H322 cells. In FIG. 5c, p-Smad2 and nuclei were stained with FITC-conjugated secondary antibody (green) and PI (red), respectively, 30 min after TGF-β treatment. Notice that p-Smad2 was increased and nuclear located by the transfection of si-DX2.

In FIG. 6a, lung tumor formation was monitored at time interval after the intraperitoneal administration of benzo-(α)-pyrene into AIMP2$^{+/+}$ and AIMP2$^{+/-}$ mice. "N" stands for the number of the sacrificed mice. In FIG. 6b, total RNAs were isolated from the tissues, and subjected to RT-PCR with the AIMP2-DX2-specific primer. Normal and tumor tissues of the same patients (indicated by code number) were RT-PCR (FIG. 6c). In FIG. 6c, the exon 4 region of AIMP2 and GAPDH were used as control.

In FIG. 8a, the AIMP2 gene is composed of four exons encoding the polypeptides of the indicated size. FIG. 8b is the schematic representation for the locations of the primers used to generate the cDNAs spanning different regions of AIMP2 and their sequences (RT Primer: SEQ ID NO:15; primers for exon 1-3: SEQ ID NOS: 5 and 6; primers for exon 3-4: SEQ ID NOS: 3 and 4; and primers for AIMP2-DX2: SEQ ID NOS: 8 and 7).

In FIG. 9a, to compare the AIMP2 levels between the AIMP2-DX2-positive and -negative cells, we cultured DU145 and H460 cells in one dish, and performed immunofluorescence staining with anti-AIMP2 antibody (green). The two cells lines were distinguished by immunofluorescence staining of p53 (red) since DU145 cells express p53 at high level due to its mutation, whereas H460 cells containing the wild type p53 maintain it at low level. The cells were treated with TGF-β for 2 hr, and fixed with methanol. In FIG. 9b, to address the effect of AIMP2-DX2 on expression of AIMP2, we monitored the AIMP2 level by flow cytometry. We transfected 2 μg/ml of empty vector or AIMP2-DX2 into DU145 cells, and incubated for 24 hr. The cells were then fixed with 70% ethanol and reacted with anti-AIMP2 antibody, and subsequently FITC-conjugated secondary antibody. In FIG. 9c, the effect of AIMP2-DX2 on the TGF-β-dependent cell cycle arrest was compared by flow cytometry. While the portion of the G0/G1 phase cells was increased in DU145 cells transfected with empty vector, but not in the AIMP2-DX2-transfected cells. The black and blues lines indicated the cells untreated and treated with TGF-β, respectively. In FIG. 9d, we compared the AIMP2 levels in H460 cells that were untreated (control) or treated with 10 μM ALLN for 2 hr. "Negative" indicates the cells incubated only with FITC-conjugated secondary antibody.

In FIG. 12, the abbreviations, pCMV, BGH pA, f1 or neomycin, ampicillin, SV40, SV40 pA, ColE1, T7 and Sp6 denote human cytomegalovirus immediate-early promoter, bovine growth hormone polyadenylation signal, f1 replication origin, neomycin resistance gene, ampicillin resistance gene, SV40 replication origin, SV40 polyadenylation signal, ColE1 replication origin, T7 viral promoter and Sp6 viral promoter.

In FIG. 13.d, tumor formation in lung was confirmed by histological analysis (×100). Numbers indicate the different mouse id.

FIG. 14 shows oncogenic property of AIMP2-DX2.

FIG. 15 shows knock-down of AIMP2-DX2 using si-AIMP2-DX2 suppresses tumor growth. In FIG. 15a, the si-control and si-AIMP2-DX2 expressing NCI-H460 cells were injected into nude mice (n=6) and tumor volumes were measured at the indicated times. The si-control or -AIMP2-DX2 RNA was additionally delivered directly into the growing tumors on 17, 20 and 23 days after cell transplantation.

FIG. 16 shows delivery of GFP-expressing plasmid to the various parts of mouse lung via intranasal inhalation.

DETAILED DESCRIPTION OF THIS INVENTION

Figure 1A:
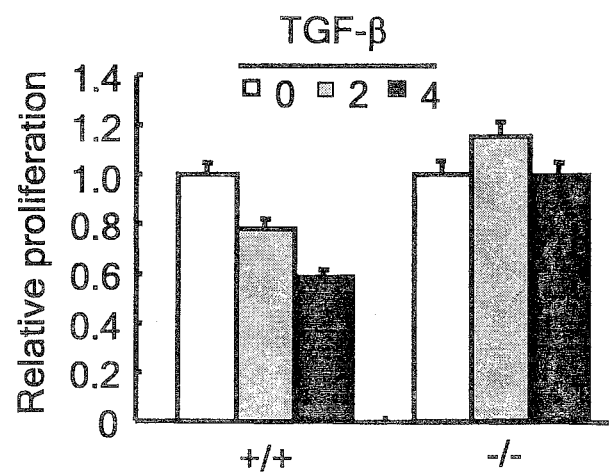
FIGS. 1a-1e represent the functional importance of AIMP2 in TGF-β signaling and its interaction with Smad2/3. AIMP2$^{+/+}$ and AIMP2$^{-/-}$ MEFs were compared in the effect of TGF-β on cell proliferation (FIG. 1a), colony formation (FIG. 1b), cell cycle progression (FIG. 1c), and nuclear translocation of Smad2 and Smad3 (FIG. 1d).

The present inventors elucidated that the genetic disruption of p38 (newly designated herein as "AIMP2") to induce overexpression of c-myc causes neonatal lethality in mice through overproliferation of alveolar epithelial cells and transforming growth factor-β (TGF-β) induces AIMP2 expression and promoted its translocation to nuclei for the downregulation of c-myc (M. J. Kim, et al., *Nat. Genet.* 34:330-336 (2003)).

Following the previous research, the present inventors have revealed that AIMP2 is a novel tumor suppressor, playing a unique role in TGF-β signaling via interaction with Smad2/3. In addition, we have discovered that the aberrant variant of AIMP2 lacking exon II (AIMP2-DX2) is specifically expressed in cancer cell lines and tissues. The existence of AIMP2 lacking exon II (AIMP2-DX2) was verified by RT-PCR using combinations of AIMP2-specific primers. When the primers were used to generate AIMP2 cDNA spanning exon 3 and 4, the decrease of AIMP2 transcript was not observed in the cells showing the reduced level of AIMP2 in Western blot analysis. When we used the primers generating the transcript from exon 1 to 3, we obtained not only the transcript of the expected size, but also a smaller one. Sequencing analysis of this small transcript revealed that it lacks exon 2 encoding 69 amino acid residues of AIMP2. RT-PCR analysis using the primer targeting to the junction sequence of exon 1 and 3 showed that the cell lines expressing lower AIMP2 level generated the smaller transcript, confirming the generation of AIMP2-DX2.

Furthermore, the inventors observed that AIMP2 level was dramatically reduced regardless of TGF-β, demonstrating that the generation of AIMP2-DX2 leads to loss of AIMP2 activity. In addition to this, the introduction of AIMP2-DX2 elevated the expression of c-myc and relived the growth arrest by TGF-β. Surprisingly, we found that AIMP2-DX2 forms a heterodimer with AIMP2 that is ubiquitinated to be rapidly degraded by proteasome-dependent degradation process. Consequently, we are urged to reason that AIMP2-DX2 is closely associated with tumorigenesis by inducing the decrease of AIMP2 level. In vivo study provides additional evidences to verify that AIMP2-DX2 is strongly related to lung and liver cancer formation as well.

It should be noted that p38DX2 described in the priority documents of this application, i.e., the Korean Pat. Appln. Nos. 2004-0097164 and 2005-0039073 is newly named as AIMP2-DX2.

In one aspect of this invention, there is provided a AIMP2-DX2 protein comprising a AIMP2 amino acid sequence in which the exon 2 region of the AIMP2 amino acid sequence is deleted, that is specifically expressed in cancer cells, in particular, lung and liver cancer cells.

Preferably, the AIMP2-DX2 protein consists of the AIMP2 amino acid sequence in which the exon 2 region of the AIMP2 amino acid sequence is deleted.

The AIMP2-DX2 protein is a deletion variant of AIMP2 lacking exon 2. The amino acid sequence of the AIMP2 protein is found in several databases (312aa version: accession Nos. AAC50391.1 and GI:1215669; 320aa version: accession Nos. AAH13630.1, GI:15489023 and BC013630.1 available from GenBank) and publications (312aa version: Nicolaides, N. C., Kinzler, K. W. and Vogelstein, B. Analysis of the 5' region of PMS2 reveals heterogeneous transcripts and a novel overlapping gene, *Genomics* 29 (2):329-334 (1995); 320 aa version: Generation and initial analysis of more than 15,000 full-length human and mouse cDNA sequences, *Proc. Natl. Acad. Sci. U.S.A.* 99(26): 16899-16903 (2002)). The amino acid sequence of the AIMP2-DX2 protein comprises, preferably, consists of that of AIMP2 lacking exon 2 region as afore-described known sequences. The Korean Pat. Appln. No. 10-2003-0018424 discloses cancer therapy efficacy of the AIMP2 protein, teachings of which are incorporated herein by reference in its entity.

In addition, the AIMP2-DX2 protein includes exon 2-deleted variant of AIMP2 equivalents, for example, functional equivalents resulting from substitution, deletion, insertion or their combinations of AIMP2 that exhibit substantially identical activity to the wild type AIMP2, or functional derivatives with modifications to alter physical and/or biochemical properties of the wild type AIMP2 that exhibit substantially identical activity to the wild type AIMP2.

The deletion of exon 2 in AIMP2 as described herein means that the amino acid sequence spanning exon 2 region in AIMP2 (corresponding to amino acid 46-114) is partially or wholly deleted to generate a deletion variant of AIMP2 capable of forming a heterodimer with AIMP2 to inhibit normal function of AIMP2 and promote degradation of AIMP2. Accordingly, the AIMP2-DX2 protein of this invention may include any variant of AIMP2 with whole or partial exon 2 deletion in which exon 1, 3 and/or 4 is natural or modified by amino acid substitution, deletion or insertion, so long as the variant is able to form a heterodimer with AIMP2 to inhibit normal function of AIMP2. Preferably, the AIMP2-DX2 protein comprises a whole exon 2 deletion and intact exon 1, 3 and 4. More preferably, the AIMP2-DX2 protein comprises, most preferably, consists of an amino acid sequence of SEQ ID NO:2.

The AIMP2-DX2 protein may comprise its natural-occurring amino acid sequences and variants having modified sequences as well, so long as the variants retain activity of the AIMP2-DX2 protein described above. The variants of the AIMP2-DX2 protein refer to proteins having different sequences from its natural-occurring amino acid sequence prepared by deletion, insertion, non-conserved or conserved substitution or their combinations. The silent alteration of amino acid residues not to substantially impair protein activity is well known to one skilled in the art (H. Neurath, R. L. Hill, The Proteins, Academic Press, New York, 1979). Such amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

In addition, the AIMP2-DX2 protein may comprise post-translational modifications such as phosphorylation, sulfation, acrylation, glycosylation, methylation and farnesylation.

The AIMP2-DX2 protein and its variants may be obtained by the isolation from natural sources, synthesis (Merrifleld, *J. Amer. Chem. Soc.* 85:2149-2156 (1963)) or recombinant DNA technology (Joseph Sambrook, et al., *Molecular Cloning, A Laboratory Manual*, Cold Spring Harbor Laboratory Press, Cold Spring Harbor, N.Y. (2001)). Where a recombinant DNA technology is applied, host cells are transformed with an expression vector carrying a nucleic acid molecule encoding AIMP2-DX2 and then cultured, followed by recovering the AIMP2-DX2 expressed.

As described previously, the AIMP2-DX2 protein is specifically expressed in a variety of cancer cells including breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease esophageal cancer, small intestine cancer, endocrine cancer, thyroid cancer, parathyroid cancer, adrenal cancer, soft tissue tumor, urethral cancer, penile cancer, prostate cancer, bronchogenic cancer, nasopharyngeal cancer, laryngeal cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas and pituitary adenoma, in particular, lung and liver cancer tissues, demonstrating that the AIMP2-DX2 protein can serve as a cancer diagnostic marker.

In another aspect of this invention, there is provided a nucleic acid molecule comprising a nucleotide sequence encoding the AIMP2-DX2 protein described above.

Preferably, the nucleic acid molecule coding for the AIMP2-DX2 protein comprises a nucleotide sequence of SEQ ID NO:1. More preferably, the nucleic acid molecule of this invention consists of a nucleotide sequence of SEQ ID NO:1.

It is well understood by the skilled artisan that homologous sequences due to codon degeneracy may be encompassed within the nucleic acid molecule of the present invention, showing at least 60%, preferably 80%, most preferably 90-95% nucleotide similarity to that of SEQ ID NO:1, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44 (1988); Higgins and Sharp, *CABIOS* 5:151-3 (1989); Corpet et al., *Nuc. Acids Res.* 16:10881-90 (1988); Huang et al., *Comp. Appl. BioSci.* 8:155-65 (1992); and Pearson et al., *Meth. Mol. Biol.* 24:307-31 (1994). The NCBI Basic Local Alignment Search Tool (BLAST) (Altschul et al., *J. Mol. Biol.* 215:403-10 (1990)) is available from several sources, including the National Center for Biological Information (NBCl, Bethesda, Md.) and on the Internet, for use in connection with the sequence analysis programs blastp, blasm, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

The nucleic acid molecule of this invention may be single- or double-chain DNA (cDNA and gDNA) or single-chain RNA (mRNA).

The nucleic acid molecule encoding the AIMP2-DX2 protein may be prepared by the isolation from natural sources, synthesis or recombinant DNA technology. The AIMP2-DX2 nucleic acid molecule may be included in a suitable vector to provide the AIMP2-DX2 protein.

In still another aspect of this invention, there is provided a recombinant vector which comprises a nucleic acid molecule comprising a nucleotide sequence encoding the AIMP2-DX2 protein.

The term "recombinant vector" used herein refers to a genetic carrier to express a protein or RNA of interest in a suitable host cell, comprising a corresponding foreign sequence operably linked to a nucleic acid expression control sequence (such as a promoter, signal sequence and array of transcription factor binding sites).

The term "operably linked" used herein refers to functional linkage between a nucleic acid expression control sequence and a second nucleic acid sequence of interest, wherein the expression control sequence affects transcription and/or translation of the nucleic acid corresponding to the second sequence. The vector of this invention may be constructed according to conventional recombinant DNA technology in which site-specific DNA cleavage and ligation are performed using commercially available enzymes.

The vector of the present invention includes plasmid, cosmid, bacteriophage and viral vectors, but not limited to. The vector may comprise expression control elements such as promoter, operator, start and stop codons, polyadenylation signal and enhancer as well as signal or leader sequences for membrane targeting or secretion. The promoter used in vectors may be constitutive or inducible one. Furthermore, the vector may carry a selection marker for selecting host cells harboring the vector and a replication origin.

The signal sequence in the vector includes, but not limited to, PhoA and OmpA signal sequences for *Escherichia* host cells, α-amylase and subtilicin signal sequences for *Bacillus* host cells, MFα and SUC2 signal sequences for yeast host cells, and insulin, α-interferon and antibody molecule signal sequences for animal host cells.

In further aspect of this invention, there is provided a transformant which is transformed with the recombinant vector of this invention described above.

The transformation may be carried out according to any known approach for transforming nucleic acid molecules into organism, cell, tissue or organ, including electroporation, protoplasm fusion, $CaPO_4$ precipitation, $CaCl_2$ precipitation, agitation using silicon carbamide fiber, *Agrobacterium*-mediated transformation, PEG, dextran sulfate and lipofectamine, but not limited to. A suitable transformation method may be selected based on the type of host cells.

A suitable host cell is generally decided in considering the expression level and post-translation modification. Host cells include, but not limited to, prokaryotic cells such as *Escherichia coli*, *Bacillus subtilis*, *Streptomyces*, *Pseudomonas*, *Proteus mirabilis* and *Staphylococcus*, fungi (e.g., *Aspergillus*), yeast (e.g., *Pichia pastoris*, *Saccharomyces cerevisiae*, *Schizosaccharomyces* and *Neurospora crassa*), insect cells, plant cells and mammalian cells.

In still further aspect of this invention, there is provided a process for preparing the AIMP2-DX2 protein by culturing transformed cells described previously.

The culturing is carried out by conventional methods known to those skilled in the art under conditions suitable to express the AIMP2-DX2 protein of interest.

The AIMP2-DX2 protein expressed may be purified by conventional methods, for example, salting out (e.g., ammonium sulfate and sodium phosphate precipitation), solvent precipitation (e.g., protein fractionation precipitation using acetone or ethanol), dialysis, gel filtration, ion exchange, reverse-phase column chromatography, ultrafiltration or their combinations (Sambrook et al., *Molecular Cloning*: A Laboratory Manual, 3rd Ed., Cold Spring Harbor Laboratory Press (2001); and Deutscher, M., Guide to Protein Purification Methods, Enzymology, vol. 182. Academic Press. Inc., San Diego, Calif. (1990)).

The term "cancer marker" used herein refers to a substance that provides information to evaluate cancer likelihood, occurrence or development by examining qualitatively or quantitatively its expression in tissues or cells. Preferably, the term means an organic biomolecule (e.g., protein, DNA and RNA) that is expressed in cancer cells in a different pattern from normal cells. The AIMP2-DX2 gene or protein of this invention is specifically expressed in cancer cells but not in normal cells, permitting to accurately diagnose cancer (preferably, lung and liver cancer). Preferably, the cancer diagnosis using AIMP2-DX2 expression is performed in mRNA and/or protein level.

In another aspect of this invention, there is provided an antibody specific to the AIMP2-DX2 protein.

The term "antibody" used herein means a protein molecule specifically directed toward an antigenic site. The antibody of this invention refers to antibodies to specifically recognize AIMP2-DX2 with discriminating AIMP2, including polyclonal and monoclonal antibodies.

Antibodies against the novel protein, AIMP2-DX2, may be prepared in accordance with conventional technologies known to one skilled in the art.

Polyclonal antibodies may be prepared according to known processes in which the AIMP2-DX2 protein as an immunogen is injected into animals and then antiserum is collected. Immunized animals include, but not limited to, goat, rabbit, sheep, monkey, horse, pig, cattle and dog.

Monoclonal antibodies may be prepared in accordance with a fusion method (Kohler and Milstein, *European Journal of Immunology*, 6:511-519 (1976)), a recombinant DNA method (U.S. Pat. No. 4,816,56) or a phage antibody library (Clackson et al, *Nature*, 352:624-628 (1991); and Marks et al, *J. Mol. Biol.*, 222:58, 1-597 (1991)).

Antibodies against the AIMP2-DX2 protein may be an intact immunoglobulin molecule or its fragments containing antigen-binding site such as F(v), Fab, Fab' and F(ab')2.

The antibodies of this invention specific to AIMP2-DX2 permit to diagnose cancer (preferably, lung and liver cancer) as well as to treat cancer (preferably, lung and liver cancer) by suppressing the activity of AIMP2-DX2. Where the antibodies are used as a therapeutic agent, they may be coupled to conventional therapeutic agents in direct or indirect (through a linker) manner.

The therapeutic agent coupled to the antibodies of this invention includes, but not limited to, radionuclide (e.g., 131I, 90Y, 105Rh, 47Sc, 67Cu, 212Bi, 211At, 67Ga, 125I, 186Re, 188Re, 177Lu, 153Sm, 123I and 111In), drug (e.g., methotrexate and adriamycin), lymphokine (interferon), toxin (ricin, abrin and diphtheria) and heterofunctional antibody that forms a complex with other antibody to posses a bi-functional binding capacity both to cancer cell and effector cell (e.g., T killer cell).

The antibody of this invention may be administered per se or in the form of a pharmaceutical composition.

The pharmaceutical composition comprising antibody may be formulated with a pharmaceutically acceptable carrier. The form of the pharmaceutical composition varies depending on the administration mode. Typically, the composition comprises one of surfactants for facilitating transmembrane delivery. Such surfactant includes steroid-derived compounds, cationic lipids such as N-[1-(2,3-dioleyloxy) propyl]-N,N,N-trimethylammonium chloride (DOTMA), cholesterol hemisuccinate and phosphatidyl glycerol.

The pharmaceutical composition comprising the antibody of this invention is administered in a pharmaceutically effective amount to treat cancer or prevent cancer metastasis. The pharmaceutical composition may be administered in a single or multiple dosing regimen. The administration mode of the pharmaceutical composition includes parenteral, subcutaneous, intraperitoneal, intrapulmonary, intranasal, and local administration. Parenteral administration includes subcutaneous, intradermal, intramuscular, intravenous, intrabursa, intrasternal, intrathecal and intraperitoneal injection. The pharmaceutical composition is generally formulated in a pH range of 4-8 for antibody stability (chemical and physical stability) and safety. In addition, the pharmaceutical composition may be formulated in an oral dosing form. Typical dose is optimized using standard clinical techniques.

Furthermore, the antibody of this invention may be administered in a form of nucleic acid molecule to induce in vivo production of antibody (WO 96/07321).

In still another aspect of this invention, there is provided a diagnostic kit for cancer, which comprises an antibody specific to the AIMP2-DX2 protein.

The cancer diagnosis kit of this invention may comprise antibody specific to AIMP2-DX2 as well as general instruments and reagents for immunoassay including carrier, detectable signal-generating label, dissolving agent, washing agent, buffer and stabilizer. Where an enzyme is used as a label, its substrate and reaction quencher may be included. Non-limiting examples of carrier include soluble carriers, for example, physiologically acceptable buffer known in the art (e.g. PBS), insoluble carriers, for example, polystyrene, polyethylene, polypropylene, polyester, polyacrylonitrile, fluorine resin, cross-linked dextran, polysaccharides, polymers such as magnetic microparticles made of latex coated with a metal, paper, glass, metals, agarose and combinations thereof.

Non-limiting examples of the assay system useful in the cancer diagnosis kit of the present invention include ELISA plates, dip-stick devices, immunochromatography test strips and radial partition immunoassy devices and flow-through devices.

In further aspect of this invention, there is provided a method for diagnosing cancer, which comprises the steps of: (a) providing a sample to be assayed; and (b) detecting in the sample an expression of a nucleotide sequence encoding the AIMP2-DX2 protein of claim 1, wherein the detection of the expression of the nucleotide sequence encoding the AIMP2-DX2 protein is indicative of cancer.

The sample used in the present invention includes any biological sample such as tissue, cell, whole blood, serum, plasma, saliva, semen, urine, synovia and spinal fluid and may be pretreated for assay.

The present method may be carried out at protein or mRNA level. Where it is performed to detect the AIMP2-DX2 protein, antibodies to specifically recognize the AIMP2-DX2 protein are used and the detection is carried out by contacting the sample to the antibody specific to the AIMP2-DX2 protein and evaluating a formation of antigen-antibody complex. The evaluation on antigen-antibody complex formation may be carried out using immunohistochemical staining, radioimmuno assay (RIA), enzyme-linked immunosorbentassay (ELISA), Western blotting, immunoprecipitation assay, immunodiffusion assay, complement fixation assay, FACS and protein chip assay. The evaluation on antigen-antibody complex formation may be performed qualitatively or quantitatively, in particular, by measuring signal from detection label.

The label to generate measurable signal for antigen-antibody complex formation includes, but not limited to, enzyme, fluorophore, ligand, luminophore, microparticle, redox molecules and radioisotopes. The enzymatic label includes, but not limited to, β-glucuronidase, β-D-glucosidase, β-D-galactosidase, urease, peroxidase, alkaline phosphatase, acetylcholinesterase, glucose oxidase, hexokinase, GDPase, RNase, luciferase, phosphofructokinase, phosphoenolpyruvate carboxylase, aspartate aminotransferase, phosphenolpyruvate decarboxylase, β-lactamase. The fluorescent label includes, but not limited to, fluorescein, isothiocyanate, rhodamine, phycoerythrin, phycocyanin, allophysocyanin, o-phthalate and fluorescamine. The ligand serving as a label includes, but not limited to, biotin derivatives. Non-limiting examples of the luminescent label includes acridinium ester, luciferin and luciferase. Microparticles as label include colloidal gold and colored latex, but not limited to. Redox molecules for labeling include ferrocene, lutenium complex compound, viologen, quinone, Ti ion, Cs ion, diimide, 1,4-benzoquinone, hydroquinone, $K_4W(CN)_8$, $[Os(bpy)_3]^{2+}$, $[Ru(bpy)_3]^{2+}$ and $[Mo(CN)_8]^{4-}$, but not limited to. The radioisotopes includes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{131}I$ and $^{186}Re$, but not limited to.

Where the present method is performed to detect the AIMP2-DX2 mRNA, the detection step may be carried out by an amplification reaction or a hybridization reaction well-known in the art.

The phrase "detection of the AIMP2-DX2 mRNA" used herein is intended to refer to analyze the existence or amount of the AIMP2-DX2 mRNA as cancer diagnosis marker in cells by use of primer or probe specifically hybridized with the AIMP2-DX2 mRNA.

The term "primer" used herein means an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleoside triphosphates and a thermostable enzyme in an appropriate buffer and at a suitable temperature.

The term "probe" used herein refers to a linear oligomer of natural or modified monomers or linkages, including deoxyribonucleotides, ribonucleotides and the like, which is capable of specifically hybridizing with a target nucleotide sequence, whether occurring naturally or produced synthetically. The probe used in the present method may be prepared in the form of oligonucleotide probe, single-stranded DNA probe, double-stranded DNA probe and RNA probe. It may be labeled with biotin, FITC, rhodamine, DIG and radioisotopes.

The method to detect the AIMP2-DX2 mRNA using either primer or probe includes, but not limited to, DNA sequencing, RT-PCR (reverse transcription-polymerase chain reaction), primer extension method (Nikiforov, T. T. et al., *Nucl Acids Res* 22, 4167-4175 (1994)), oligonucleotide ligation analysis (OLA)(Nickerson, D. A. et al., *Pro Nat Acad Sci USA,* 87, 8923-8927 (1990)), allele-specific PCR (Rust, S. et al., *Nucl Acids Res,* 6, 3623-3629 (1993)), RNase mismatch cleavage (Myers R. M. et al., *Science,* 230, 1242-1246 (1985)), single strand conformation polymorphism (SSCP; Orita M. et al., Pro Nat Acad Sci USA, 86, 2766-2770 (1989)), simultaneous analysis of SSCP and heteroduplex (Lee et al., Mol Cells, 5:668-672 (1995)), denaturation gradient gel electrophoresis (DGGE; Cariello N F. et al., Am J Hum Genet, 42, 726-734 (1988)) and denaturing high performance liquid chromatography (D-HPLC, Underhill P A. et al., Genome Res, 7, 996-1005 (1997)).

Preferably, the method by amplification reaction is carried out by RT-PCR using a primer capable of differentiating an mRNA of AIMP2-DX2 from an mRNA of AIMP2. RT-PCR process suggested by P. Seeburg (1986) for RNA research involves PCR amplification of cDNA obtained from mRNA reverse transcription. For amplification, a primer pair specifically annealed to AIMP2-DX2 is used. Preferably, the primer is designed to generate two different sized bands in electrophoresis in which one is specific to the AIMP2 mRNA and the other to AIMP2-DX2 mRNA. Alternatively, the primer is designed to generate only electrophoresis band specific to AIMP2-DX2 mRNA. The primer pair to generate two different sized bands for the AIMP2 mRNA and AIMP2-DX2 mRNA is prepared to amplify a region corresponding to exon 2. The nucleotide sequence of such primers is not limited; most preferably, a primer set consisting of SEQ ID NOs:5 and 6. To observe only one electrophoresis band specific to AIMP2-DX2 mRNA, one of primers is designed to comprise the junction sequence between C-terminal of exon 1 and N-terminal of exon 3. In Examples described below, the primer of SEQ ID NO:8 annealed to the junction sequence is used together with the primer of SEQ ID NO:7 for RT-PCR. The RT-PCR analysis is convenient in the senses that cancer diagnosis is accomplished by observing the electrophoresis band pattern to evaluate expression of the AIMP2-DX2 mRNA.

The present method may be carried out in accordance with hybridization reaction using suitable probes.

The stringent conditions of nucleic acid hybridization suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985). As used herein the term "stringent condition" refers to the conditions of temperature, ionic strength (buffer concentration), and the presence of other compounds such as organic solvents, under which hybridization or annealing is conducted. As understood by those of skill in the art, the stringent conditions are sequence dependent and are different under different environmental parameters. Longer sequences hybridize or anneal specifically at higher temperatures.

The probes used in the hybridization reaction have a AIMP2-DX2 specific nucleotide sequence which is not found in AIMP2. Preferably, the probes are designed to comprise the junction sequence between exons 1 and 3, most preferably, having the nucleotide sequence of SEQ ID NO:8.

The present method is very useful in diagnosing a variety of cancer including breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease esophageal cancer, small intestine cancer, endocrine cancer, thyroid cancer, parathyroid cancer, adrenal cancer, soft tissue tumor, urethral cancer, penile cancer, prostate cancer, bronchogenic cancer, nasopharyngeal cancer, laryngeal cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas and pituitary adenoma. More preferably, the present method is used for diagnosing lung cancer and liver cancer, most preferably, lung cancer.

In still further aspect of this invention, there is provided a siRNA (small interfering RNA) molecule which comprise a nucleotide sequence complementary to a region of an mRNA of the AIMP2-DX2 protein.

The term "siRNA" used herein refers to a short RNA duplex to induce RNAi (RNA interference) phenomenon through mRNA cleavage. The siRNA consists of a sense RNA strand corresponding to target mRNA and an antisense RNA strand complementary to target mRNA. siRNA to inhibit expression of a target gene provides effective gene knockdown method or gene therapy method.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably, 15-80 nucleotides, and more preferably, 20-70 nucleotides. The siRNA may comprise either blunt or cohesive end so long as it enables to silent the AIMP2-DX2 expression due to RNAi effect. The cohesive end may be prepared in 3'-end overhanging structure or 5'-end overhanging structure. The overhanging bases are not limited in its length, for example, 1-8 nucleotides, preferably, 2-6 nucleotides. The overall length as described herein is expressed as the total of length of central double-stranded portion and terminal single-stranded overhanging portion. Furthermore, as long as AIMP2-DX2 siRNA is able to maintain its gene silencing effect on the target gene, it may contain a low molecular weight RNA (which may be a natural RNA molecule such as tRNA, rRNA or viral RNA, or an artificial RNA molecule), for example, in the overhanging portion at its either end. It is not necessary that both ends of AIMP2-DX2 siRNA have a cleavage structure. The AIMP2-DX2 siRNA of this invention may comprise a stem-loop structure in which either end (head or tail) is connected via a linker. The length of the linker is not limited unless it impairs base pairing in stem structure.

Sequence specific siRNA molecule of the present invention may be designed using one or more of several criteria. For example, to design a siRNA polynucleotide that has 18 consecutive nucleotides identical to a sequence encoding a polypeptide of interest (e.g., AIMP2-DX2), the open reading frame of the polynucleotide sequence may be scanned for 21-base sequences that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence (such an evaluation can be readily determined using computer programs available to a skilled artisan such as BLAST to search publicly available databases). Alternatively, a siRNA polynucleotide sequence may be designed and chosen using a computer software available commercially from various vendors (e.g., OligoEngine™ (Seattle, Wash.); Dharmacon, Inc. (Lafayette, Colo.); Ambion Inc. (Austin, Tex.); and QIAGEN, Inc. (Valencia, Calif.)). (See also Elbashir et al., Genes & Development 15:188-200 (2000); Elbashir et al., Nature 411: 494-98 (2001); and [online] Internet:URL<http://www-.mpibpc.gwdg.de/abteilungen/100/105/Tusch1_MIV2-(3) 2002.pdf.).

The siRNA polynucleotides may then be tested for their ability to interfere with the expression of the target polypeptide according to methods known in the art and described herein. The determination of the effectiveness of an siRNA polynucleotide includes not only consideration of its ability to interfere with polypeptide expression but also includes consideration of whether the siRNA polynucleotide manifests undesirably toxic effects, for example, apoptosis of a cell for which cell death is not a desired effect of RNA interference (e.g., interference of AIMP2-DX2 expression in a cell).

It should be appreciated that not all siRNAs designed using the above methods will be effective at silencing or interfering with expression of a desired target polypeptide. And further, that the siRNAs will effect silencing to different degrees. Such siRNAs must be tested for their effectiveness, and selections made therefrom based on the ability of a given siRNA to interfere with or modulate (e.g., decrease in a statistically significant manner) the expression of the target. Accordingly, identification of specific siRNA polynucleotide sequences that are capable of interfering with expression of a desired target polypeptide requires production and testing of each siRNA, as demonstrated in greater detail below (see Examples).

Furthermore, not all siRNAs that interfere with protein expression will have a physiologically important effect. The inventors here have designed, and describe herein, physiologically relevant assays for measuring the influence of modulated target polypeptide expression, for instance, cellular proliferation, induction of apoptosis, and/or altered levels of protein tyrosine phosphorylation (e.g., insulin receptor phosphorylation), to determine if the levels of interference with target protein expression that were observed using the siRNAs of the invention have clinically relevant significance. Additionally, and according to non-limiting theory, the invention contemplates altered (e.g., decreased or increased in a statistically significant manner) expression levels of one or more polypeptides of interest, and/or altered (i.e., increased or decreased) phosphorylation levels of one or more phosphoproteins of interest, which altered levels may result from impairment of target protein expression and/or cellular compensatory mechanisms that are induced in response to RNAi-mediated inhibition of a specific target polypeptide expression.

Persons having ordinary skill in the art will also readily appreciate that as a result of the degeneracy of the genetic code, many nucleotide sequences may encode a polypeptide as described herein. That is, an amino acid may be encoded by one of several different codons and a person skilled in the art can readily determine that while one particular nucleotide sequence may differ from another (which may be determined by alignment methods disclosed herein and known in the art), the sequences may encode polypeptides with identical amino acid sequences. By way of example, the amino acid leucine in a polypeptide may be encoded by one of six different codons (TTA, TTG, CTT, CTC, CTA, and CTG) as can serine (TCT, TCC, TCA, TCG, AGT, and AGC). Other amino acids, such as proline, alanine, and valine, for example, may be encoded by any one of four different codons (CCT, CCC, CCA, CCG for proline; GCT, GCC, GCA, GCG for alanine; and GTT, GTC, GTA, GTG for valine). Some of these polynucleotides bear minimal homology to the nucleotide sequence of any native gene. Nonetheless, polynucleotides that vary due to differences in codon usage are specifically contemplated by the present invention.

Polynucleotides, including target polynucleotides, may be prepared using any of a variety of techniques, which will be useful for the preparation of specifically desired siRNA polynucleotides and for the identification and selection of desirable sequences to be used in siRNA polynucleotides. For example, a polynucleotide may be amplified from cDNA prepared from a suitable cell or tissue type. Such polynucleotides may be amplified via polymerase chain reaction (PCR). For this approach, sequence-specific primers may be designed based on the sequences provided herein and may be purchased or synthesized. An amplified portion may be used to isolate a full-length gene, or a desired portion thereof, from a suitable library (e.g., human skeletal muscle cDNA) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences. Suitable sequences for a siRNA polynucleotide contemplated by the present invention may also be selected from a library of siRNA polynucleotide sequences.

For hybridization techniques, a partial sequence may be labeled (e.g., by nick-translation or end-labeling with .sup.32P) using well known techniques. A bacterial or bacteriophage library may then be screened by hybridizing filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full-length cDNA molecule can be generated by ligating suitable fragments, using well known techniques.

A number of specific siRNA polynucleotide sequences useful for interfering with target polypeptide expression, and are presented in the Examples, the Drawings, and the Sequence Listing. SiRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated to improve theur serum stability and/or delivery properties. Included as an aspect of the invention are the siRNAs described herein wherein the ribose has been removed therefrom. Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as T7, U6, H1, or SP6). In addition, a siRNA polynucleotide may be administered to a patient, as may be a DNA sequence (e.g., a recombinant nucleic acid construct as provided herein) that supports transcription (and optionally appropriate processing steps) such that a desired siRNA is generated in vivo.

Accordingly, a siRNA polynucleotide that is complementary to at least a portion of a target polypeptide-encoding sequence may be used to modulate gene expression, or as a probe or primer. Identification of siRNA polynucleotide sequences and DNA encoding genes for their targeted delivery involves techniques described herein. Identification of such siRNA polynucleotide sequences and DNA encoding genes for their targeted delivery involves techniques that are also described herein. As discussed above, siRNA polynucleotides exhibit desirable stability characteristics and may, but need not, be further designed to resist degradation by endogenous nucleolytic enzymes by using such linkages as phosphorothioate, methylphosphonate, sulfone, sulfate, ketyl, phosphorodithioate, phosphoramidate, phosphate esters, and other such linkages (see, e.g., Agrwal et al., Tetrahedron Lett. 28:3539-3542 (1987); Miller et al., J. Am. Chem. Soc. 93:6657-6665 (1971); Stec et al., Tetrahedron Lett. 26:2191-2194 (1985); Moody et al., Nucleic Acids Res. 12:4769-4782 (1989); Uznanski et al., Nucleic Acids Res. (1989); Letsinger at al., Tetrahedron 40:137-143 (1984); Eckstein, Annu. Rev. Biochem. 54:367402 (1985); Eckstein, Trends Biol. Sci. 14:97-100 (1989); Stein, In: Oligodeoxynucleotides. Antisense Inhibitors of Gene Expression, Cohen, ed., Macmillan Press, London, pp. 97-117 (1989); Jager et al., Biochemistry 27:7237-7246 (1988)).

Any polynucleotide of the invention may be further modified to increase stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives, and cosmids. Vectors of particular interest include expression vectors, replication vectors, probe generation vectors, and sequencing vectors. In general, a suitable vector contains an origin of replication functional in at least one organism, convenient restriction endonuclease sites, and one or more selectable markers. (See, e.g., WO 01/96584; WO 01/29058; U.S. Pat. No. 6,326,193; U.S. 2002/0007051). Other elements will depend upon the desired use, and will be apparent to those having ordinary skill in the art. For example, the invention contemplates the use of siRNA polynucleotide sequences in the preparation of recombinant nucleic acid constructs including vectors for interfering with the expression of a desired target polypeptide such as an AIMP2-DX2 or a chemotherapeutic target polypeptide in vivo; the invention also contemplates the generation of siRNA transgenic or "knockout" animals and cells (e.g., cells, cell clones, lines or lineages, or organisms in which expression of one or more desired polypeptides (e.g., a target polypeptide) is fully or partially compromised). An siRNA polynucleotide that is capable of interfering with expression of a desired polypeptide (e.g., a target polypeptide) as provided herein thus includes any siRNA polynucleotide that, when contacted with a subject or biological source as provided herein under conditions and for a time sufficient for target polypeptide expression to take place in the absence of the siRNA polynucleotide, results in a statistically significant decrease (alternatively referred to as "knockdown" of expression) in the level of target polypeptide expression that can be detected. Preferably the decrease is greater than 10%, more preferably greater than 20%, more preferably greater than 30%, more preferably greater than 40%, 50%, 60%, 70%, 75%, 80%, 85%, 90%, 95% or 98% relative to the expression level of the polypeptide detected in the absence of the siRNA, using conventional methods for determining polypeptide expression as known to the art and provided herein. Preferably, the presence of the siRNA polynucleotide in a cell does not result in or cause any undesired toxic effects, for example, apoptosis or death of a cell in which apoptosis is not a desired effect of RNA interference.

Within certain embodiments, siRNA polynucleotides may be formulated so as to permit entry into a cell of a mammal, and expression therein. Such formulations are particularly useful for therapeutic purposes, as described below. Those having ordinary skill in the art will appreciate that there are many ways to achieve expression of a polynucleotide in a target cell, and any suitable method may be employed. For example, a polynucleotide may be incorporated into a viral vector using well known techniques (see also, e.g., U.S. 2003/0068821). A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those having ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Within other embodiments, one or more promoters may be identified, isolated and/or incorporated into recombinant nucleic acid constructs of the present invention, using standard techniques. The present invention provides nucleic acid molecules comprising such a promoter sequence or one or more cis- or trans-acting regulatory elements thereof. Such regulatory elements may enhance or suppress expression of a siRNA. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding luciferase, beta-galactosidase, chloramphenicol acetyl transferase, secreted alkaline phosphatase, or the Green Fluorescent Protein gene (see, e.g., Ui-Tei et al., FEBS Lett. 479:79-82 (2000). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U or T is denoted in the context of the present invention, the ability to substitute a T or U is implied, unless otherwise stated.

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 79% or greater complementarity. For example, a mismatch in a duplex region consisting of 19 base pairs results in 94.7% complementarity, rendering the duplex region substantially complementary.

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

The term "specific" used herein in conjunction with siRNA is intended to express the inhibition of target gene expression with no influence on other genes. The siRNA of this invention is specific to the AIMP2-DX gene.

It is preferred that the siRNA of this invention comprise a sense strand containing a corresponding sequence to a junction sequence between exons 1 and 3 and an antisense strand containing a complementary sequence.

The phrase "inhibition of gene expression" means that the level of mRNA and/or protein generated from the target gene is quenched or reduced, which is induced by RNA interference via occurrence of mRNA cleavage.

The siRNA of this invention may be synthesized in vitro and then introduced into cells via transfection. In addition, it may be transfected into cells in the form of siRNA expression vector or PCR-derived siRNA expression cassette. Suitable preparation and transfection methods may be determined in considering the experiment aim and target gene function.

The sequences and length of the siRNA are not limited as long as it enables to suppress the AIMP2-DX2 expression. 3 illustrative siRNA expression vectors to silence AIMP2-DX2 are found in Examples described hereunder, suppressing cellular level of AIMP2-DX2 and restoring AIMP2 function and TGF-β signal transduction.

The preferable siRNA of this invention comprises a corresponding sequence to the junction sequence between exons 1 and 3 of the AIMP2-DX2 mRNA. More preferably, the siRNA of this invention is a RNA duplex described as (i) No. 3 siRNA consisting of two RNA molecules expressed from nucleotide sequences of SEQ ID NOs:9 and 10, (ii) No. 4 siRNA consisting of two RNA molecules expressed from nucleotide sequences of SEQ ID NOs:11 and 12, or (iii) No. 5 siRNA consisting of two RNA molecules expressed from nucleotide sequences of SEQ ID NOs:13 and 14. The siRNA consisting of two RNA molecules expressed from nucleotide sequences of SEQ ID NOs:11 and 12 is most preferred. The single or mixed type of siRNA molecules may be used.

In another aspect of this invention, there is provided an antisense oligonucleotide which is complementary to a region of an mRNA of the AIMP2-DX2 protein.

The term "antisense oligonucleotide" used herein is intended to refer to nucleic acids, preferably, DNA, RNA or its derivatives, that are complementary to the base sequences of a target mRNA, characterized in that they binds to the target mRNA and interfere its translation to protein. The antisense oligonucleotide of this invention means DNA or RNA sequences complementary and binding to AIMP2-DX2 mRNA, that are able to inhibit translation, translocation, maturation or other biological functions of AIMP2-DX2 mRNA. The antisense nucleic acid is 6-100, preferably, 8-60, more preferably, 10-40 nucleotides in length.

The antisense oligonucleotide may at lease one modification in its base, sugar or backbone for its higher inhibition efficacy (De Mesmaeker et al., *Curr Opin Struct Biol.*, 5(3): 343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA*, 86:6553 (1989)), cholic acid (Manoharan et al. *Bioorg. Med. Chem. Let.*, 4:1053 (1994)), a thioether, e.g., hexyl-S-tritylthiol (Manoharan et al. *Ann. N.Y. Acad. Sci.*, 660:306 (1992); Manoharan et al. *Bioorg. Med.*

Chem. Let., 3: 2765 (1993)), a thiocholesterol (Oberhauser et al., Nucl. Acids Res., 20:533 (1992)), an aliphatic chain, e.g., dodecandiol or undecyl residues (Saison-Behmoaras et al. EMBO J., 10:111 (1991); Kabanov et al. FEBS Lett., 259:327 (1990); Svinarchuk et al. Biochimie, 75:49 (1993), a phospholipid, e.g., di-hexadecyl-rac-glycerol or triethylammonium 1,2-di-O-hexadecyl-rac-glycero-3-H-phosphonate (Manoharan et al. Tetrahedron Lett., 36:3651 (1995); Shea et al. Nucl. Acids Res., 18:3777 (1990)), a polyamine or a polyethylene glycol chain (Manoharan et al. Nucleosides & Nucleotides, 14:969 (1995)), or adamantane acetic acid (Manoharan et al. Tetrahedron Lett., 36: 3651 (1995)). Oligonucleotides comprising lipophilic moieties, and methods for preparing such oligonucleotides are known in the art, for example, U.S. Pat. Nos. 5,138,045, 5,218,105 and 5,459,255. The modifications described above enhance stability against nuclease degradation and increase affinity of the antisense oligonucleotide toward its target mRNA.

It is preferred that the antisense oligonucleotide specific to AIMP2-DX2 comprises a complementary sequence to a junction region between exons 1 and 3 of AIMP2-DX2 mRNA.

The antisense RNA molecule is conventionally synthesized in vitro and then transmitted to cells. In addition, it is intracellularly produced by transcription from foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to peptide.

In another aspect of this invention, there is provided a pharmaceutical composition for treating cancer, which comprises (a) the antisense oligonucleotide or siRNA specific to AIMP2-DX2 mRNA as an active ingredient; and (b) a pharmaceutically acceptable carrier.

In still another aspect of this invention, there is provided a method for treating cancer in a patient, which comprises administrating into the patient a pharmaceutical composition (a) the antisense oligonucleotide or siRNA specific to AIMP2-DX2 mRNA as an active ingredient; and (b) a pharmaceutically acceptable carrier.

The pharmaceutical composition comprising at least one of AIMP2-DX2 siRNAs or antisense oligonucleotides may contain additional agent to suppress tumor cell proliferation and to facilitate the transduction of siRNA or antisense nucleic acid, for example, liposome (U.S. Pat. Nos. 4,897,355, 4,394,448, 4,235,871, 4,231,877, 4,224,179, 4,753,788, 4,673,567, 4,247,411 and 4,814,270), or lipophilic carrier including sterols such as cholesterol, cholate and deoxycholic acid. In addition, the siRNA or antisense nucleic acid is conjugated to cell-adsorbing peptides such as peptide hormones, antigens and peptide toxins (Haralambid et al, WO 89/03849; Lebleu et al., EP 0263740).

Where the pharmaceutical composition is formulated for oral administration, it may contain binder, lubricant, disintegrator, diluent, solubilizer, dispersing agent, stabilizer, suspending agent, pigment and sweetner. Where the pharmaceutical composition is formulated for injection, it may contain buffer, preservative, solubilizer, tonicity agent and stabilizer. For topical administration, the pharmaceutical composition may contain substrate, diluent, lubricant and preservative. The formulation of the pharmaceutical composition may be prepared by formulating with pharmaceutically acceptable carriers described above. For oral administration, the pharmaceutical composition may be in the form of tablet, troche, capsule, elixir, suspension, syrup and wafer. The injectable composition may be formulated in unit dosage ample or multi dosage form.

The correct dosage of the pharmaceutical compositions of this invention comprising AIMP2-DX2 siRNA or antisense oligonucleotide will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions.

The administration mode of the pharmaceutical composition includes oral and parenteral such as subcutaneous, intradermal, intramuscular, intravenous, intrabursa, intrasternal, intrathecal and intraperitoneal injections.

In further aspect of this invention, there is provided a method of screening for an agent which inhibits the formation of a heterodimer between the AIMP2-DX2 protein of claim 1 and the AIMP2 protein, comprising the steps of: (a) contacting a test substance to a composition which comprises the AIMP2-DX2 protein and the AIMP2 protein; and (b) determining whether the test substance inhibits the heterodimer formation between the AIMP2-DX2 protein and the AIMP2 protein, wherein the test substance to inhibit the heterodimer formation between the AIMP2-DX2 protein and the AIMP2 protein is evaluated as an anticancer agent.

The formation of the heterodimer between the AIMP2-DX2 protein and AIMP2 protein is associated with cancer as demonstrated in Examples described hereunder. Therefore, a substance capable of inhibiting the heterodimer formation is evaluated as a candidate for anticancer agent.

According to a preferred embodiment, the instant method is performed by a yeast-two-hybrid assay and in vitro pull-down assay.

Where the present method is carried out by yeast-two-hybrid assay format, the composition comprising the AIMP2-DX2 protein and the AIMP2 protein is a cell harboring the respective gene.

In a yeast two-hybrid assay, the AIMP2-DX2 protein and AIMP2 protein can be used as either "bait" or "prey" (see, e.g., U.S. Pat. No. 5,283,317; Zervos et al., Cell 72, 223-232 (1993); Madura et al., J. Biol. Chem. 268, 12046-12054 (1993); Bartel et al., BioTechniques 14, 920-924 (1993); Iwabuchi et al., Oncogene 8, 1693-1696 (1993); and Brent W0 94/10300), to identify substances which inhibits the interaction of AIMP2-DX2 with AIMP2 to form a heterodimer. The two-hybrid system is based on the modular nature of most transcription factors, which consist of separable DNA-binding and activation domains. Briefly, the assay utilizes two different DNA constructs. For example, in one construct, polynucleotide encoding the AIMP2-DX2 protein can be fused to a polynucleotide encoding the DNA binding domain of a known transcription factor (e.g. Lex). In the other construct a DNA sequence that encodes the AIMP2 protein can be fused to a polynucleotide that codes for the activation domain of the known transcription factor (e.g. B42).

If the test substance treated to cells expressing the two-hybrid system is able to inhibit the interaction between the AIMP2-DX2 protein and AIMP2 protein, the DNA-binding and activation domains of the transcription factor are not brought into close proximity. This proximity allows transcription of a reporter gene (e.g. lac Z), which is operably linked to a transcriptional regulatory site responsive to the transcription factor. Expression of the reporter gene can be easily detected.

In an in vitro, pull-down assay format, the AIMP2-DX2 gene and AIMP2 gene can be used as either bait or prey. For example, in one construct for bait, the AIMP2 protein is fused to a protein that allows the AIMP2 protein to be bound to a solid support. For example, glutathione-S-transferase (GST) fusion proteins can be adsorbed onto glutathione Sepharose beads or glutathione derivatized microtiter plates. In the other construct for prey, the AIMP2-DX2 protein is synthesized by in vitro translation system (e.g., reticulocyte lysate) using $^{35}S$. The radioactive AIMP2-DX2 protein is added to the GST-AIMP2 protein bound to glutathione Sepharose beads together with the addition of the test substance. The reaction mixture is washed and the proteins bound to the Sepharose beads are eluted, followed by electrophoresis.

If the test substance added to the reaction mixture is able to inhibit the interaction between the AIMP2-DX2 protein and AIMP2 protein, the electrophoresis result shows no band.

In still further aspect of this invention, there is provided a method of screening for an agent which inhibits the expression of the AIMP2-DX2 gene, comprising the steps of: (a) contacting a test substance to cells which express the AIMP2-DX2 gene; and (b) determining whether the test substance inhibits the expression of the AIMP2-DX2 gene, wherein the test substance to inhibit the expression of the AIMP2-DX2 gene is evaluated as an anticancer agent.

In the present method, the expression of the AIMP2-DX2 gene is assessed at mRNA or protein level. Where the present method is carried out to detect the AIMP2-DX2 mRNA expressed, it is preferably performed by RT-PCR using AIMP2-DX2 specific primers described hereinabove. Where the present method is carried out to detect the AIMP2-DX2 protein expressed, it is preferably performed by a variety of immunoassay processes using AIMP2-DX2 specific antibodies as described above.

The following specific examples are intended to be illustrative of the invention and should not be construed as limiting the scope of the invention as defined by appended claims.

EXAMPLES

Methods

Cell Culture, Chemicals and Cell Cycle Measurement

Cells were maintained in RPMI-1640 containing 10% FBS. Mouse embryonic fibroblasts (MEFs) were isolated from 12.5-14.5 day embryos and cultivated in DMEM (Dulbecco's Modified Eagle Medium) containing 20% FBS. To evaluate the effect of TGF-β on cell cycle, cells were incubated with 2 ng/ml TGF-β in serum-free or 1% FBS-containing medium for 24 hr and harvested for FACS analysis. Cell proliferation was also determined by [$^3$H] thymidine incorporation. Cells were incubated in serum-free medium with or without TGF-β for 20 hr, and then in the presence of 1 µCi/ml of [$^3$H] thymidine for 4 hr. The incorporated thymidine was quantified by liquid scintillation counting as previously described (Kim, M. J. et al., *Nat. Genet.* 34, 330-336 (2003)). TGF-β was purchased from R&D system, and anti-Smad2 and anti-Smad4 antibodies from Santa Cruz.

Normal lung cell line, WI-26, was purchased from Korea Cell Line Bank (KCLB) and NL-20 was a kind gift from Dr. M.-H. Cho (Seoul National University). Lung carcinoma cell lines A549, NCI-H460 were obtained from ATCC, H322 and H157 from KCLB. The siRNAs targeting AIMP2-F and -DX2 were designed by Invitrogen as previously described. The shRNA against DX2 was cloned to IMG-700 vector by SalI and XbaI (IMGENEX).

Production of Monoclonal Antibody of AIMP2-DX2

The monoclonal antibodies were produced by a known method (Kennettm McKearn, and Bechtol (eds.), *Monoclonal Antibodies, Hybridomas; A New Dimension in Biological Analyses*, Plenum Press, 1980). The monoclonal antibodies were produced by immunizing an animal with the AIMP2-DX2 protein as an immunogen, fusing the splenocytes of the immunized animal with myeloma cell, P3X63Ag8.653, (ATCC CRL-1580, USA) to produce a hybridomas, screening a hybridoma that selectively recognizes the AIMP2-DX2 protein, culturing the screened hybridoma, and isolating antibodies from the hybridoma culture. And the selected hybridoma was injected into abdominal cavity of mice, and after a given period of time, antibodies were isolated from the collected ascites of the mice. The immunoglobulin isotype of the isolated antibody (clone number 324) was determined using Isotyping kit (Zymed Labomouseories Inc. USA).

Immunoblotting and Immunoprecipitation

Cells were treated with TGF-β for the indicated times and proteins were extracted with protease-containing RIPA buffer (1% Nonidet P-40, 0.5% sodium deoxycholate, 0.1% SDS), separated by 10-12% SDS-PAGE, and immunoblotted with the specific antibodies using ECL system (Santa cruz biotech). For immunoprecipitation, the cell lysates were cleared by pre-incubation with IgG (Pierce) and agarose-conjugated protein A (Invitrogen). After centrifugation, the supernatants were incubated with the specific antibody, and agarose-conjugated protein A for 2 hr. After washing with ice-cold PBS twice and RIPA once, the bound proteins were precipitated with the specific antibody, eluted and subjected to Western blot analysis.

RT-PCR

Figure 8A:
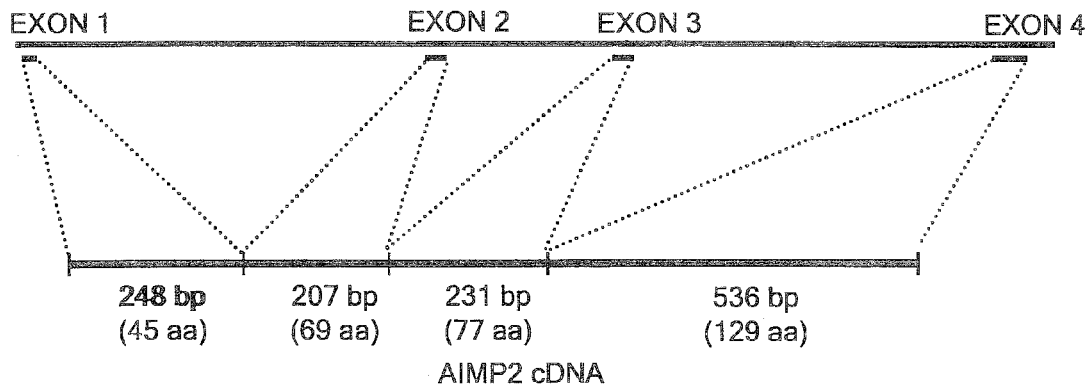
FIGS. 8a and 8b show the exon arrangement of human AIMP2 gene and the primer locations in AIMP2 cDNA.
Figure 8B:
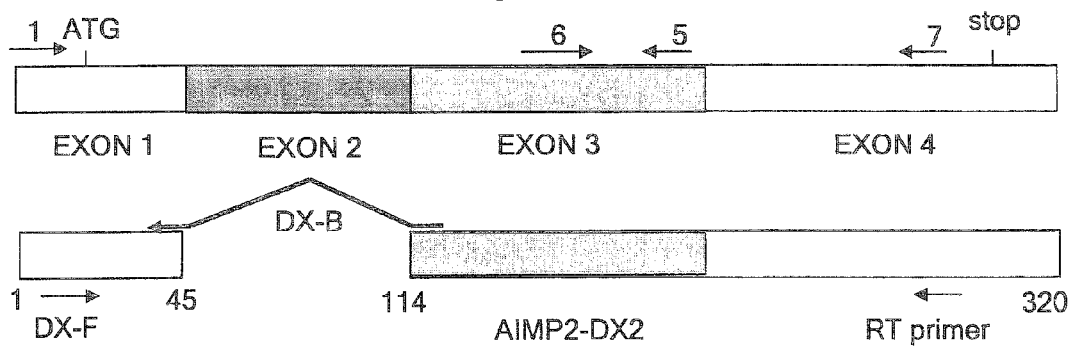

The total RNAs were isolated following the protocol of the manufacturer (Qiagen). Briefly, the freshly prepared tissues (3×3×3 mm) were chopped into small pieces, mixed with 350 µl lysis buffer and homogenized using homogenizer or syringe. After adding 350 µl of 70% ethanol, the lysates were inverted several times, loaded onto column, centrifuged at 13,000 RPM for 15 sec. After washing the column with wash buffer twice, RNAs were eluted with 40 µl RNase-free DW. For reverse transcription, 1 µg of the isolated RNA was used as a template with the AIMP2-specific primer (FIG. 8b). After the reaction, the mixture was diluted 3 fold with DW and 1 µl of its aliquot was used for 30 µl PCR reaction containing 0.5 µl dNTP (2.5 mM each), 0.5 µl of the indicated primers (each 10 pM), 1.5 µl DMSO and 0.1 µl Taq polymerase (5 U/µl).

Suppression of AIMP2-DX2 with si-RNA or sh-RNA

To suppress the expression of AIMP2-DX2, we designed the shRNA against AIMP2-DX2 with the sequence of

TCGA*GCTGGCCACGTGCAGGA*TTACGAGTACTGG*TAATCCTGCACGTGG

CCAGCTTTT* (SEQ ID NO: 26; italicized regions are matched to the AIMP2-DX2 sequence)

and cloned it into 16 IMT-700 vector system (Imgenex) using SalI and XbaI, followed by DNA sequencing for confirming the cloned sequence. H322 cells (ATCC, human lung epithelial carcinoma) were transfected with 2 µg of si-AIMP2-DX2 expression vector. Specifically, following 3-hr incubation with DNA-liposome complex in 1 ml serum-free media, H322 cells were treated with 1 ml RPMI-1640 containing 20% FBS. Then, cells were incubated in serum-free medium with or without TGF-β for 20 hr.

We also designed shRNA against AIMP2-DX2 (SEQ ID NO:26:

TCGA<u>GCTGGCCACGTGCAGG</u>ATTACGAGTACTGG<u>TAATCCTGCACGTGG
CCAGC</u>TTTT, underlined regions are matched to the DX2 sequence) and (SEQ ID NO:155:

TCGA<u>GCGGGCCACGTGCAGG</u>ACTATTCAAGAGAT<u>AGTCCTGCACGTGGC
CCGC</u> TTTT, underlined regions are matched to the DX2 sequence), and cloned into IMT-700 vector system (Imgenex) using SalI, and XbaI. The plasmid was then transfected into the indicated cells.

And we also designed duplex siRNA of AIMP2-F (Invitrogen) with the sense sequence of AGUCUAACCU GUCU-CUGCAA GCUCU (SEQ ID No:25). And we also designed duplex siRNA of AIMP2-DX2 (Invitrogen & Samchully) with the sense sequence of Table 1 below. The indicated cells were transfected with a mixture of the duplex siRNA and lipofectamin 2000 (invitrogen) (1:1 (volume:volume)). After 48 hrs incubation, the transfected cell was subjected to lysis by PBS buffer (containing 0.1% SDS and 1% tritonX 100) and western blotting with AIMP2-DX2 monoclonal antibody.

TABLE 1

| Lane No. | Sequence | SEQ ID NO |
|---|---|---|
| 1 | CAC GUG CAG GAU UAC GGG GCG CUG A | SEQ ID NO: 115 |
| 2 | CUG GCC ACG UGC AGG AUU A | SEQ ID NO: 27 |
| 3 | GCC ACG UGC AGG AUU ACG G | SEQ ID NO: 30 |
| 4 | CCA CGU GCA GGA UUA CGG G | SEQ ID NO: 31 |
| 5 | CGU GCA GGA UUA CGG GGC G | SEQ ID NO: 34 |
| 6 | ACG UGC AGG AUU ACG GGG C | SEQ ID NO: 33 |
| 7 | CGU GCA GGA UUA CGG GGC GCU GAA A | SEQ ID NO: 117 |
| 8 | ACG UGC AGG AUU ACG GGG CGC UGA A | SEQ ID NO: 116 |

Yeast Two-Hybrid Analysis

The cDNAs encoding human AIMP2 and Smad2 (and its deletion fragments) were obtained by PCR using specific primers. The PCR products of Smad2 and AIMP2 were digested with EcoRI and XhoI, and ligated into the same sites of pEG202 (LexA) and pJG4-5 (B42), respectively (Gyuris, J et al., a human G1 and S phase protein phosphatase that associates with Cdk2. *Cell* 75, 791-803 (1993)). The interactions between Lex-Smad2 fragments and B42-AIMP2 were analyzed for their ability to grow on yeast medium containing X-gal as previously described (Rho, S. B. et al., *Proc Natl Acad Sci USA* 96, 4488-93. (1999)).

In Vitro Pull-Down Assay

AIMP2, AIMP2-DX2 and CDK2 were expressed as GST fusion proteins and immobilized to glutathione-Sepharose 4B (Pharmacia). The cDNA fragments encoding the AIMP2 and AIMP2-DX2 were obtained by PCR using specific primers and cloned into pET-28a vector for in vitro transcription and translation (Promega). Aliquots (10 µl) of TNT products were incubated with 5 µg of GST-AIMP2, -AIMP2-DX2 and -CDK2 immobilized on the beads in 100 µl of PBS containing 0.5% Triton X-100, 0.5 mM EDTA, and 0.5 mM phenylmethylsulfonyl fluoride. The beads were vigorously washed with the binding buffer, and the bound proteins were eluted, resolved by SDS-PAGE, and determined by autoradiography.

Construction of Cells Stably Generating AIMP2-DX2

The wild type MEFs were transfected with pcDNA-AIMP2-DX2 or pcDNA (Invitrogen) itself and the transfectants were selected in DMEM medium containing 400 µg/ml G418. After removing the untransfected cells, the transfectants were cultured in the normal medium without G418 for 3 days, fixed with 2% PFA and stained with Giemsa.

Immunostaining and Histological Analysis

The frozen tissue slides were fixed with 2% paraformaldehyde and washed with ice cold PBS. After blocking and permeablization with PBS containing 0.2% Triton X-100 (PBST) and 1% BSA, the slides were incubated with anti-AIMP2 antibody for 2 hr. After washing with PBS, they were also incubated with anti-rabbit goat IgG-FITC (Pierce) and propidium iodide (50 µg/ml, Sigma) for 1 hr, washed with PBS, mounted, and observed under a confocal microscopy (Radiance, Bio-Rad).

Construction of AIMP2-DX2 Expression Vector

Figure 12:
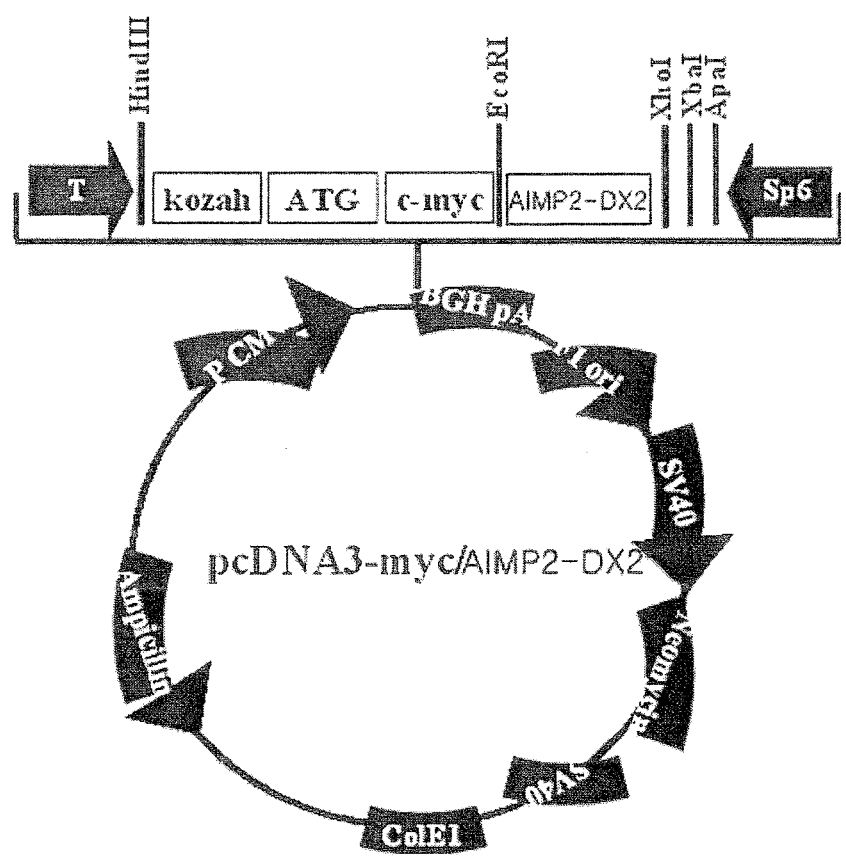
FIG. 12 shows the expression vector carrying the AIMP2-DX2 gene.

To construct the AIMP2-DX2 expressing vector, cDNA of AIMP2-DX2 was cloned into pcDNA3.1-myc. First, AIMP2-DX2 from H322 cDNA was amplified using primers with linker for EcoRI and XhoI and cloned into pcDNA3.1-myc (Invitrogen) using EcoRI and XhoI. The pcDNA3.1-myc/AIMP2-DX2 vector to express AIMP2DX (FIG. 12) was introduced into *E. coli* DH5a, which was deposited on Oct. 25, 2004 in the International Depository Authority, the Korean Collection for Type Cultures (KCTC) and was given accession number KCTC 10710BP. In the RECEIP IN THE CASE OF AN ORIGINAL DEPOSIT attached, while the identification reference read as *Escherichia coli* DH5@/p38DX2, it should be noted that p38DX2 is newly designated herein as AIMP2-DX2.

Lung Cancer Formation

32 AIMP2$^{+/-}$ mice (19 male and 13 female mice) and 25 AIMP2$^{+/+}$ mice (14 male and 11 female mice) were used for experiment. We induced lung tumor through the intraperitoneal injection of chemical carcinogen, benzo-(α)-pyrene (BP, 100 mg/kg, Sigma) into AIMP2$^{+/+}$ and AIMP2$^{+/-}$ mice, and monitored the tumor formation in lung. As a control group, 3 AIMP2$^{+/+}$ (2 male and 1 female) and 5 AIMP2$^{+/-}$ mice (4 male and 1 female) were injected with bical solution (10% DMSO and 35% PEG 40 in saline). The mice treated were sacrificed at the indicated time and their lung tissues were fixed in formaldehyde and undergone H&E staining as described in Kim, M. J. et al., *Nat. Genet.* 34:330-336 (2003), followed by the observation under a microscope.

In Situ Tissue Assay

The formalin fixed lung tissues were embedded with paraffin according to the standard procedure. The 4 µm tissue sections were stained with hematoxylin and eosin, and the tumor regions were analyzed using 1 mm cross stripes. To detect apoptosis in tissue, Apoptag kit (Chemicon) was used following manufacturer's instruction. Briefly, after deparaffinizing tissue sections, they were digested by proteinase K, incubated in the equilibration buffer, then with TdT enzyme, and followed by stop/wash buffer. After 50 µl of anti-digoxigenin-fluorescein was added to the tissue slides, the mounting solution containing 0.5 µg/ml propidium iodine was covered.

Quantitative RT-PCR

The expression of AIMP2-DX2 and -F were analyzed by quantitative real time RT-PCR. Fourteen normal lung samples and sixteen patients with lung adenocarcinoma were retrospectively identified from the surgical pathology files of the Department of Pathology at Samsung Medical Center and their archival formalin-fixed paraffin-embedded (FFPE) tissues were obtained. All the samples were collected anonymously according to Institutional Review Board guidelines. All patients had undergone a surgical operation and had received neither chemotherapy nor radiotherapy before surgical resection. For total RNA extraction from FFPE tissues, each tissue section was stained with hematoxylin and cancer regions were microdissected using laser microdissection system (ION LMD, JungWoo International, Korea). Paradise Whole Transcript RT Reagent System (Arcturus, Calif., USA) was used for RNA isolation and RT of FFPE samples. Due to the limitation of RNA amount extracted from FFPE tissues, half RNA and cDNA were used for reverse transcription and quantitative RT-PCR, respectively. PCR Primers and Taqman probes for this study are provided in Supplementary Table 1. Poly-A polymerase alpha (PAPOLA) was chosen as the endogenous reference gene for qRT-PCR. All PCR reactions were performed in a Lightcycler 2.0 (Roche Applied Science) according to standard procedures. PCR efficiency for each gene was determined by measuring serial dilutions of cDNA from H322 cells and one lung adenocarcinoma FFPE sample and calculating from Lightcycler 4.0 software. The differential gene expression of normal and cancer region was analyzed by Mann-Whitney test. All statistical analyses were done using SPSS software (SPSS, Chicago, Ill.). Mean differences were considered significant at P<0.05. For semi-quantitative RT-PCR analysis, total RNAs were isolated following the protocol of the manufacturer (Qiagen). Briefly, the freshly prepared tissues (3×3×3 mm) were chopped into small pieces, mixed with 350 l lysis buffer, homogenized using homogenizer or syringe. After adding 350 l of 70% ethanol, the lysates were inverted several times, loaded onto column, centrifuged at 13,000 RPM for 15 sec. After washing the column with wash buffer twice, RNAs were eluted with 40 µl RNase-free DW. For reverse transcription, 1 µg of the isolated RNA was used as the template with the AIMP2-specific primer. After the reaction, the mixture was diluted 3 fold with DW and 1 µl was used for 30 µl PCR reaction containing 0.5 µl dNTP (2.5 mM each), 0.5 µl of the indicated primers (each 10 pM), 1.5 µl DMSO and 0.1 µl Taq polymerase (5 U/µl).

Sequences of the quantitative RT-PCR primers and Taqman probes used for clinical specimen analysis. *PCR efficiency for each gene was determined by using serial dilution of the cDNAs obtained from lung adenocarcinoma FFPE tissues. Calculation of the efficiency was achieved using Roche Light Cycler software 4.0.

TABLE 2

| Gene | Probe | Primer | Amplicon size (bp) | PCR efficiency (dilution) * |
|---|---|---|---|---|
| AIMP 2-F | FAM-cattggtggttaaag tcgtgggctcatc-BBQ (SEQ ID NO: 157) | Forward: ctccaagatgatt caaacaccagat (SEQ ID NO: 19) Revers: ccgtaatcct tcccaagcac (SEQ ID NO: 20) | 121 | 1.94 |
| AIMP 2-DX2 | FAM-acatcgtgatcaacg caaacccg-BBQ (SEQ ID NO: 158) | Forward: gccacgtgc aggattacg (SEQ ID NO: 21) Revers: tgcaccgtg gacaggacc (SEQ ID NO: 22) | 125 | 2.07 |
| PAPO LA | DYXL-aggcgttgttttct gttggtgcac-BBQ (SEQ ID NO: 159) | Forward: aaactttttgaag ctccaaacttctt (SEQ ID NO: 23) Revers: caccaagcc cacccattc (SEQ ID NO: 24) | 135 | 1.94 |

Anchorage-Independent Colony Forming Assay

AIMP2-F, DX2 and pCDNA3 empty vector were transfected into 12.5 day mouse embryonic fibroblasts. The cell lines stably expressing each of the transfected plasmid were established by G418 selection. For soft agar colony assays, the cells were diluted into 0.3% agar in DMEM containing 10% FBS and seeded in triplicate onto 0.6% agar containing culture medium. 200 cells were seeded on each well in 12-well plate. The colonies were fed in every 3 to 4 days and evaluated after 5 weeks. To evaluate the correlation between the expression level of AIMP2-DX2 and colony formation, WI-26 cells (Korean Cell Line Bank) were treated with 0.1 µM Benzo[α]pyrene diolexpoxide (BPDE, NCI Chemical Repository) once a three days for 4 weeks and the surviving colonies were observed after 2 weeks from the chemical treatment. The 20 separate colonies were randomly selected to establish the cell lines.

In Vivo Tumor Formation

For xenograft experiment, NCI-H460 lung cancer cells ($10^8$ cells) stably expressing si-control or -AIMP2-DX2 were suspended in 0.9% saline 200 µl and subcutaneously injected into 6 week old female nude mouse. The tumor volumes were monitored three times a week. The volume was calculated by (length×width×height)/2. For chemical-induced lung cancer formation, benzo[a]pyrene (100 mg/kg, Sigma) was intraperitoneally injected into 6 weeks old outbred C57BL/6 mice, once a week two times. Benzo[a]pyrene was dissolved in 0.9% saline containing 35% PEG400 and 10% DMSO. To check tumor formation, the mice were randomly sacrificed at time interval from 6 weeks after injection. To determine survival rate and PET imaging, butylhydroxyltoluene (200 mg/kg, DukSan, Korea) was intraperitoneally injected into the mice four times in a week interval from 1 week after the last benzo[a]pyrene administration.

Gene Delivery

Inhalation therapy was examined as previously described (Kim, H. W., et al., Cancer Res. 64, 7971-7976 (2004)). Briefly, DNA vector was mixed with glucosylated polyethyleneimine (G-PEI) at 1.64:1 weight ratio. After 1 week from last chemical injection, the DNA mixture was delivered into lung through intranasal pathway using the humid vacuum chamber in which the DNA mixture was vaporized. The DNA vapor was inhaled for 30 min through the nose of the mice that were fixed in the cylinder using Bio-Rad compressor as previously described (Kim, H. W., et al., Cancer Res. 64, 7971-7976 (2004)). From 6 weeks after the last injection of BP, the administration of DNA was conducted twice a week for 4 weeks and the tumor areas were measured. For the analyses of survival and micro-PET, butylhydroxyltoluene was followed once a week for four week to further boost the cancer induction from 6 week after the BP administration. Then, the DNA was administered for 8 weeks in survival test and for 12 weeks in micro-PET and CT image analyses.

Ex Vivo Xenograft Test and Intratumoral Injection

Lung cancer NCI-H460 cells were transfected with si-control and si-AIMP2-DX2. After 24 h, $2 \times 10^7$ cells in 250 µl PBS were subcutaneously injected into 6 week old female nude mice (Orient Bio, Korea). Each of the control and si-AIMP2-DX2 treated groups was further divided to two groups of 6 individuals in 17 days after injection. In one group, si-control or si-DX2 were additionally injected directly into the growing tumors three times in 3 day interval. For intratumoral injection, 40 µl Lipofectamin 2000 (Invitrogen) and 1 nmole si-RNA in 100 l RPMI were used per 1 cm³ tumor volume. The siRNA mixtures were injected at 3 or 4 points of tumors using 31 gage needle. Tumor volumes were monitored three times a week. The experiments were terminated in 5 days after the last injection.

Image Analysis of Tumor Growth

The mice were injected with 250 µCi of [18F] fluoro-2-deoxy-D-glucose (18FDG) via tail vein. The mice were scanned for 30 min to obtain static images in 30 min after injection. We acquired Micro-PET R4 (Concorde Microsystems, Knoxyille Tenn.) that uses LSO crystals and allows timing windows of 6 nano second. The micro-PET data were reconstructed using ordered subsets expectation maximization (OSEM) algorithm with 4 iterations. The CT scans were performed using a GE Discovery LS PET/CT scanner. The CT imaging was performed with 1.2115 mm axial sampling. The CT and micro-PET images were co-registered using the fiducial markers and manually identified in both data sets to perform a point-based rigid co-registration using AMIDE (Amide's a Medical Image Data Examiner) and ASIPro (CTI Concorde Microsystems). Regions of interest (ROIs) were manually drawn over the lung region. Tracer uptake was quantified as standardized uptake values (SUVs) using the following formula: SUV=tissue activity concentration in ROI (Bq/mL)/injected dose (Bq)×body weight (g).

Results

Functional Importance and Working Mode of AIMP2 in TGF-β Signaling

Figure 1B:
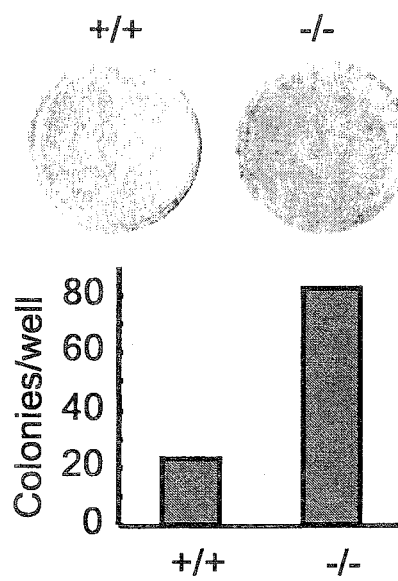
Figure 1C:
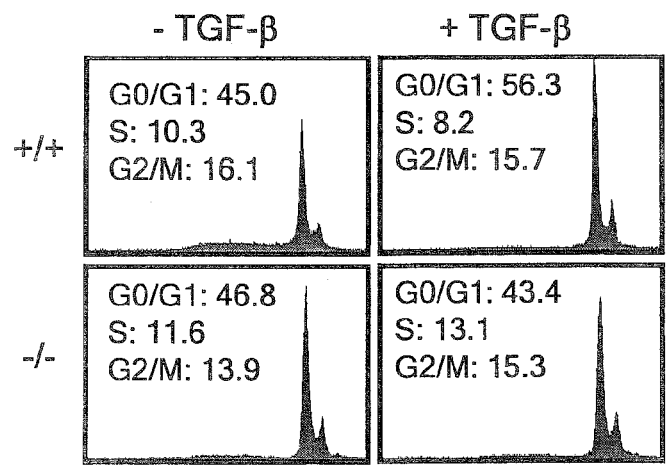
Figure 1D:
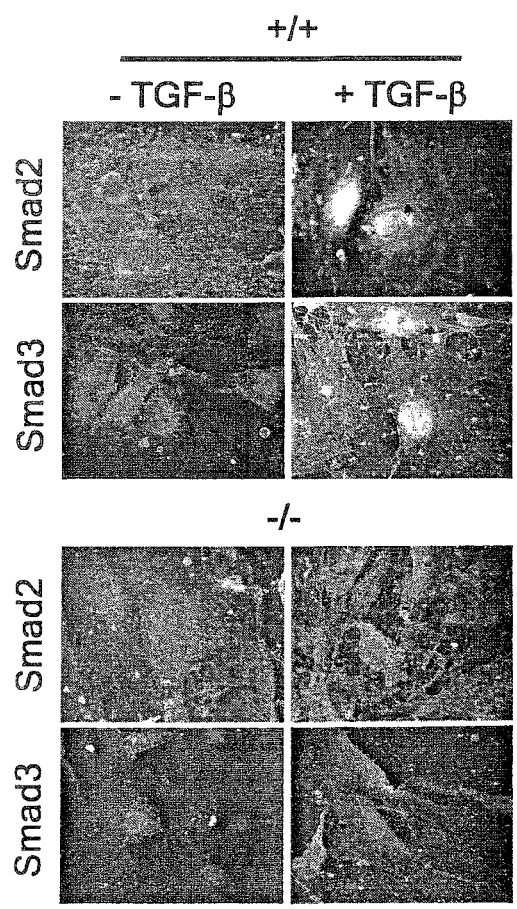

To see the importance of AIMP2 in TGF-β signaling, we compared the responses of the AIMP2$^{+/+}$ and AIMP2$^{-/-}$ MEFs to TGF-β-induced growth arrest, nuclear translocation of Smad2/3 and interaction of AIMP2 with Smad2/3. While the growth of the wild type cells was suppressed by TGF-β, the AIMP2-deficient cells did not respond to the signal as determined by thymidine incorporation, colony formation and flow cytometry (FIGS. 1a, 1b and 1c, respectively). When MEFs were treated with TGF-β, Smad2 and Smad3 were translocated to nuclei in the normal cells, but not in the AIMP2$^{-/-}$ cells (FIG. 1d). All of these results suggest the functional importance of AIMP2 in TGF-β signaling via Smad2 and Smad3.

Figure 1E:
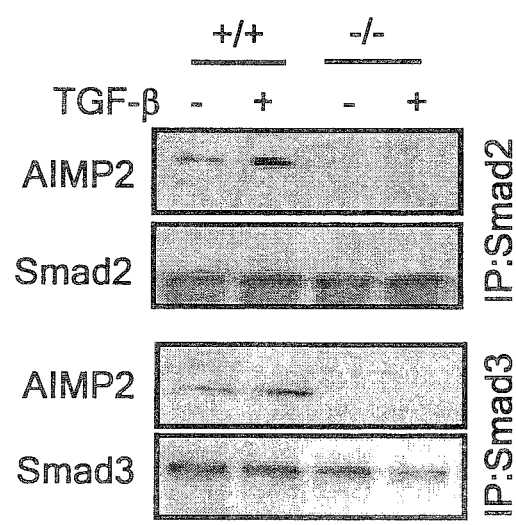
Figure 2A:
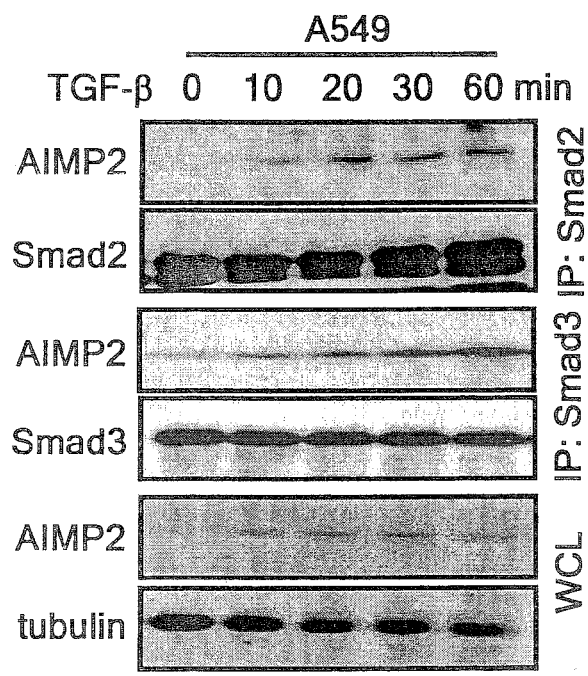
FIGS. 2a-2f represent the working mechanism of AIMP2 in TGF-β signaling.
Figure 2B:
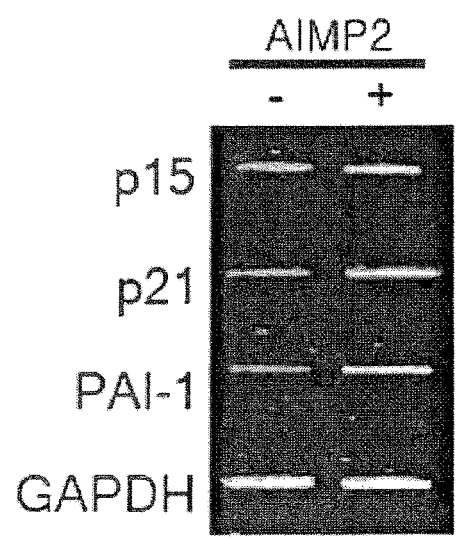
Figure 2C:
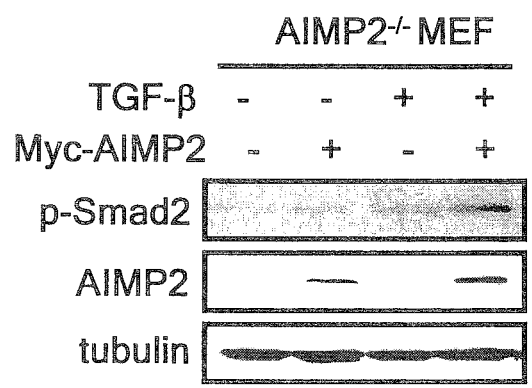
Figure 2D:
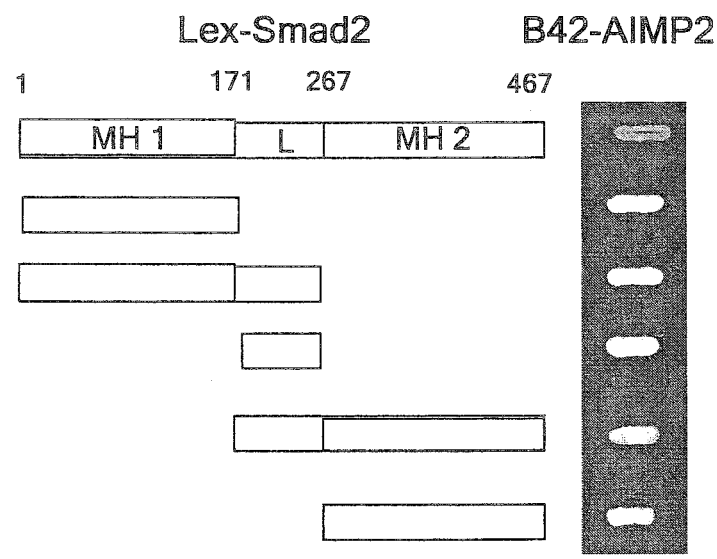
Figure 7:
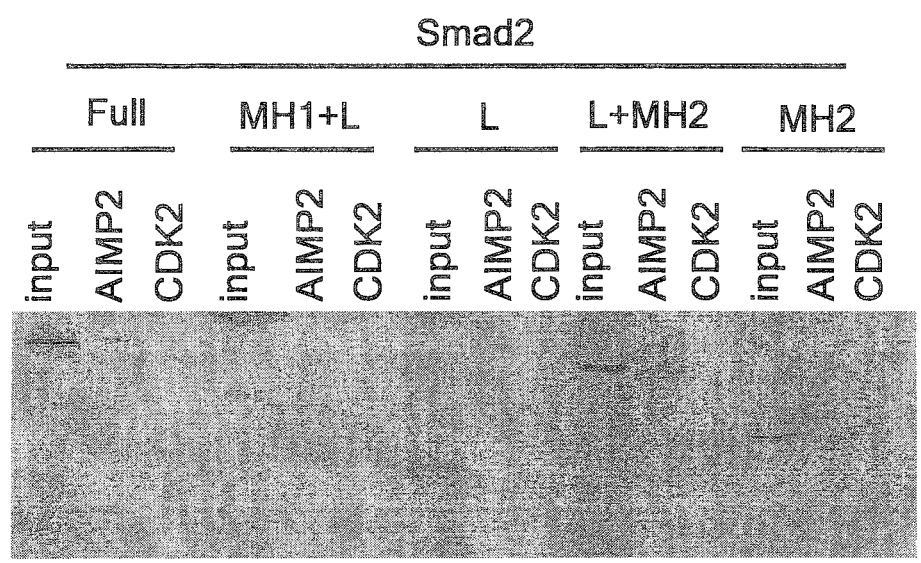
FIG. 7 represents the determination of the Smad2 domain involved in the interaction with AIMP2. We ligated the cDNAs encoding AIMP2 or CDK2 to the EcoRI and XhoI sites of pGEX4T-1 to express them in *E. coli* BL21 (DE3) as the GST-fusion proteins and purified them following the manufacturer's instruction. The different deletion fragments of Smad2 were, synthesized by in vitro translation in the presence of [$^{35}$S] methionine using the TNT coupled translation kit (Promega). The GST fusion proteins bound to the glutathione Sepharose beads were incubated with the [$^{35}$S] methionine-labeled Smad2 fragments in the binding buffer of PBS buffer (pH 7.4) containing 0.5 mM EDTA, 0.5 mM phenylmethylsulfonylfluoride (PMSF), and 1% Trition X-100. The binding mixture was incubated overnight 4° C. with rotation and washed four times with the binding buffer containing 0.5% Trition X-100. After addition of the SDS sample buffer, the bound proteins were eluted by boiling and separated by SDS gel electrophoresis. The presence of Smad2 fragments was determined by autoradiography.

We then checked the possible interaction of AIMP2 with Smad2 and 3 by coimmunoprecipitation. AIMP2 showed the interaction with Smad2/3 that was enhanced by TGF-β (FIG. 1e). The direct interaction of AIMP2 with two R-Smads was also confirmed by yeast two hybrid and in vitro pull-down assays (FIGS. 2 and 7). The amount of AIMP2 bound to Smad2/3 was increased according to the induction of AIMP2 by TGF-β (FIG. 2a). When the AIMP2 level was increased by transfection, the expression of the TGF-β target genes was enhanced, suggesting its stimulatory role in TGF-β signaling (FIG. 2b). Since AIMP2 binds to both of Smad2 and 3, we expected that it would work to these two R-Smads in a similar way and thus focused on its relationship to Smad2 in more detail. The TGF-β-dependent phosphorylation of Smad2 was suppressed in the AIMP2-deficient MEFs, but restored when AIMP2 was introduced to AIMP2$^{-/-}$ cells (FIG. 2c). We then determined the domain of Smad2 involved in the interaction with AIMP2 by yeast two hybrid (FIG. 2d) and in vitro pull-down assay (FIG. 7). The two experiments revealed that the interaction involves the MH2 domain of Smad2.

Figure 2E:
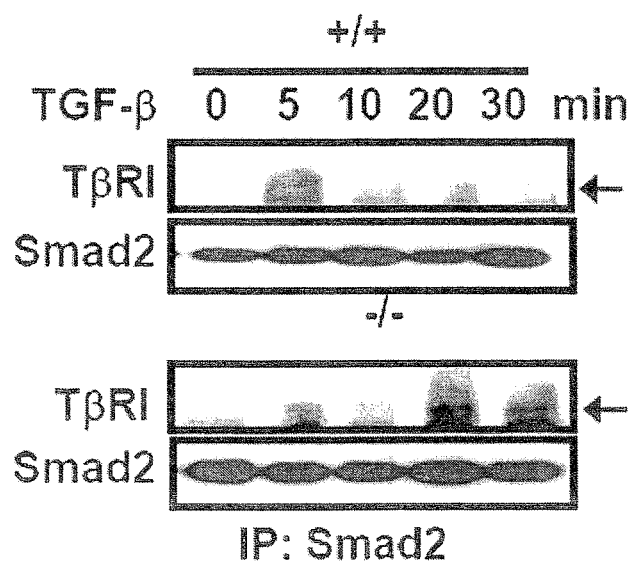
Figure 2F:
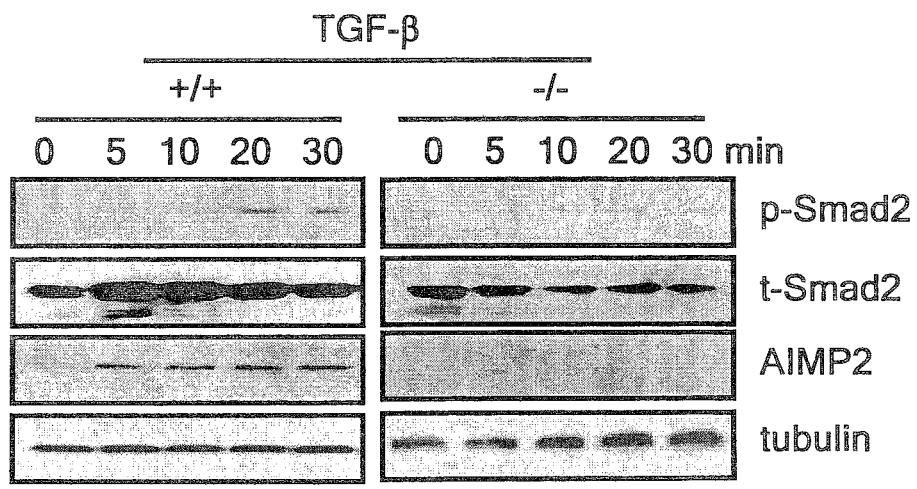

To determine the working mode of AIMP2 in TGF-β signaling, we compared the TGF-β-induced association of Smad2 with TGF-β receptor in the normal and AIMP2-deficient cells. The cells were treated with TGF-β and the association of Smad2 and the receptor was monitored by co-immunoprecipitation of type I receptor with Smad2 at time interval. While the TGF-β-induced Smad2 binding to TGF-β receptor was observed at early time point and decreased in the wild type cells, the receptor bound to Smad2 was accumulated in the late stage after TGF-β treatment in the AIMP2-deficient cells (FIG. 2e). In the TGF-β-induced phosphorylation of Smad2, the phosphorylated Smad2 was gradually increased in the wild type cells, but severely suppressed in the AIMP2$^{-/-}$ cells (FIG. 2f). These results demonstrate that AIMP2 plays a critical role in the TGF-β induced phosphorylation of R-Smads via its direct interaction with R-Smad2.

Suppression of AIMP2 and Generation of its Deletion Variant in Cancer Cells

Figure 3A:
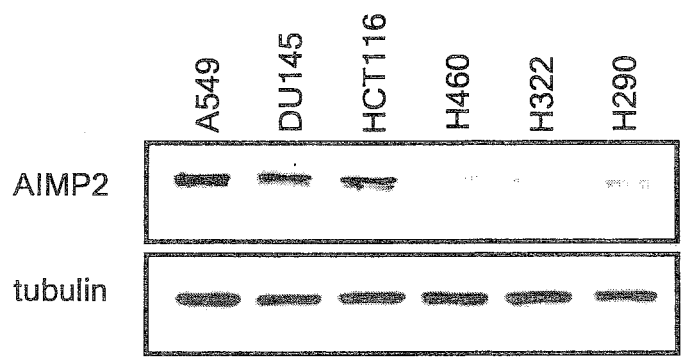
FIGS. 3a-3f represents the differential expression of AIMP2 and generation of its exon 2-deletion form. The AIMP2 levels were compared in various cancer cell lines by Western blot analysis (FIG. 3a) and flow cytometry (FIG. 3b). A549, NCI-H460, -H322, and H290 are lung cancer cell lines while DU145 and HCT116 are prostate and colon cancer cell lines, respectively.
Figure 3B:
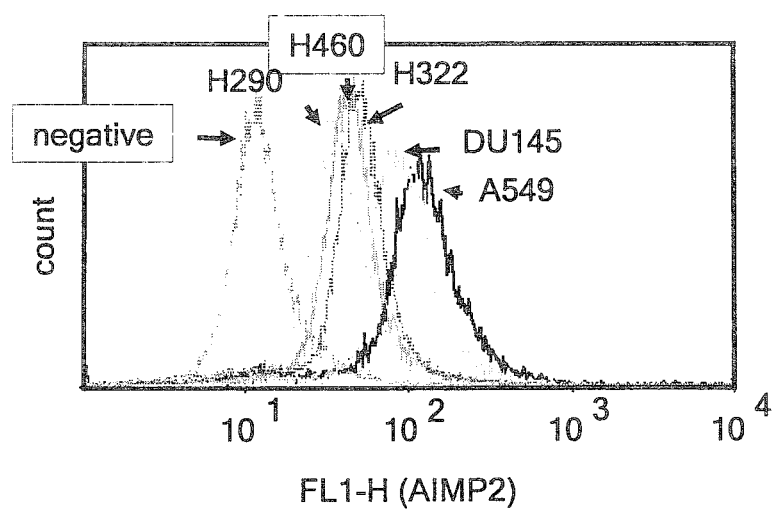
Figure 3C:
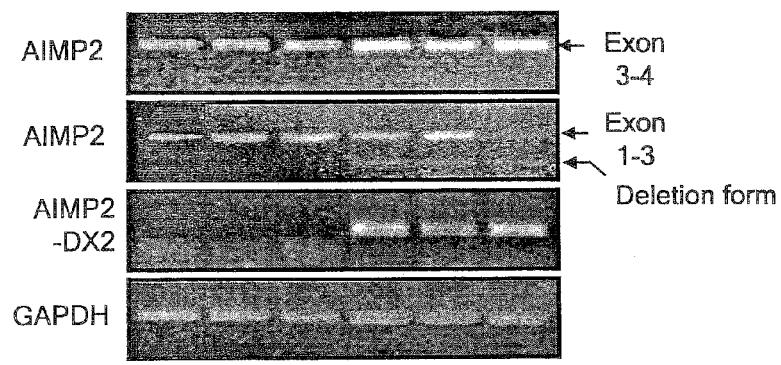

To explore the possible association of AIMP2 with cancer formation, we checked the variation of AIMP2 level in different cancer cell lines [A549 (lung epithelial carcinoma), DU145 (prostate carcinoma), HCT116 (human colorectal carcinoma), H460 (large cell lung carcinoma), H322 (lung bronchioalveolar carcinoma) and H290 (mesothelioma cancer cell line) available from ATCC]. Three of the six tested cell lines showed lower AIMP2 level in Western blot (FIG. 3a) and FACS analyses (FIG. 3b). All of the cell lines with low AIMP2 level expressed the normal level of the TGF-β type II receptor and retained its kinase activity, implying that the low AIMP2 level does not result from the mal-functionality of the receptor. To determine whether the variation of AIMP2 level resulted from the difference in transcription, we performed RT-PCR with different combinations of the AIMP2-specific primers. The AIMP2 gene consists of four exons (FIG. 8a). When the primers were used to generate AIMP2 cDNA spanning exon 3 and 4, the decrease of AIMP2 transcript was not observed in the cells showing the reduced level of AIMP2 (FIG. 3c, first row), suggesting that it does not result from lower transcription. When we used the primers generating the transcript from exon 1 to 3, we obtained not only the transcript of the expected size, but also a smaller one (FIG. 3c, second row). Sequencing analysis of this small transcript revealed that it lacks exon 2 encoding 69 aa of AIMP2 (FIG. 8b). To confirm the generation of this smaller transcript, we designed the primer (FIG. 8b, primer DX-B) targeting to the junction sequence of exon 1 and 3 that is generated by the deletion of exon 2, and conducted RT-PCR with this primer. The cell lines expressing lower AIMP2 level generated the smaller transcript (designated AIMP2-DX2, FIG. 3c, second and third rows).

Figure 3D:
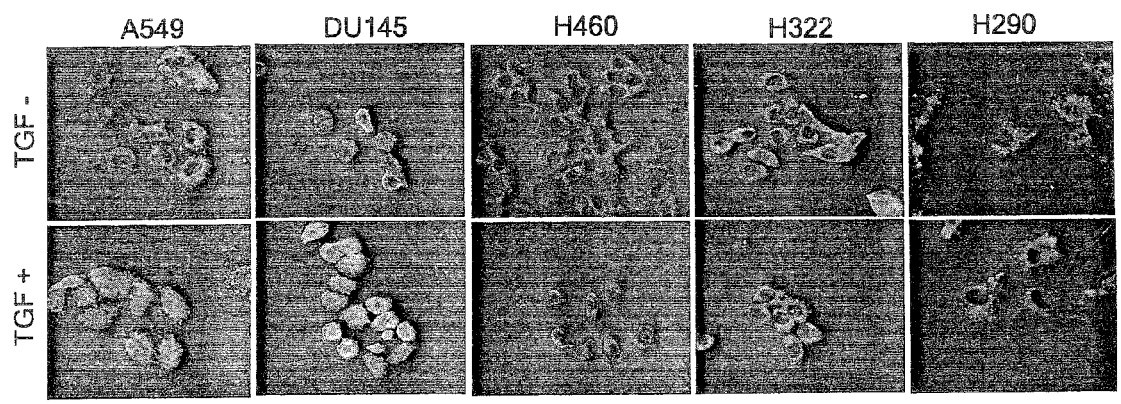
Figure 3E:
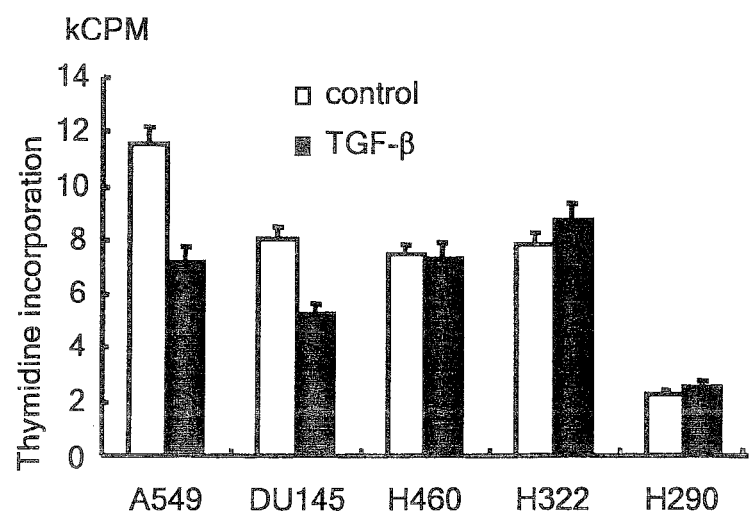
Figure 3F:
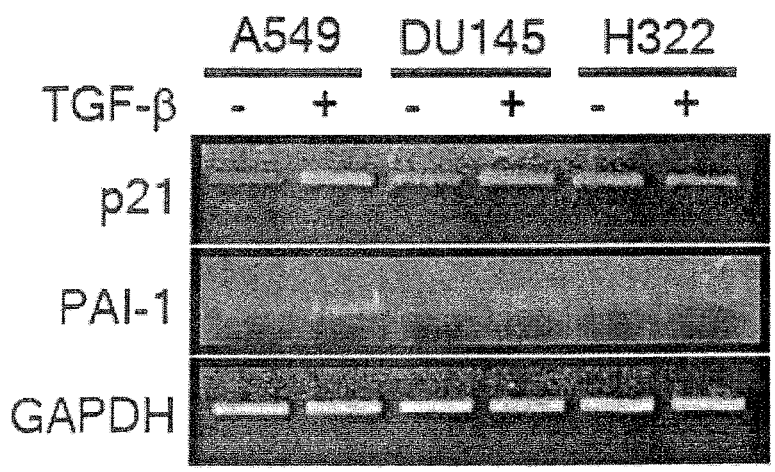
Figure 9A:
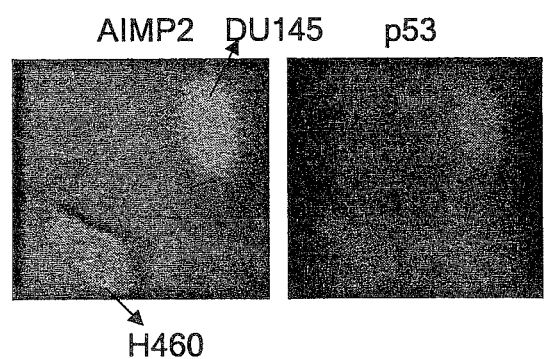
FIGS. 9a-9d demonstrate reduced expression of AIMP2, and generation of AIMP2-DX2 in cancer cell lines.
Figure 9B:
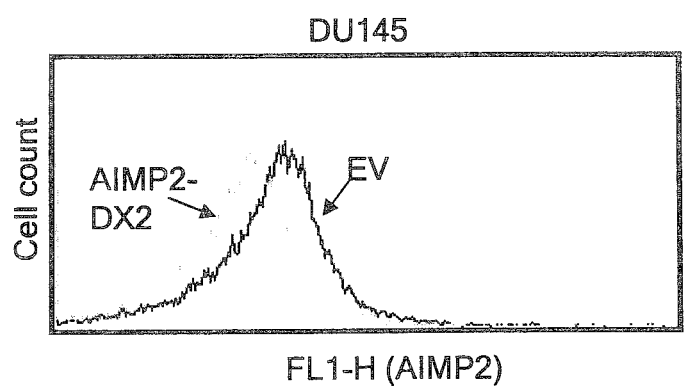
Figure 9C:
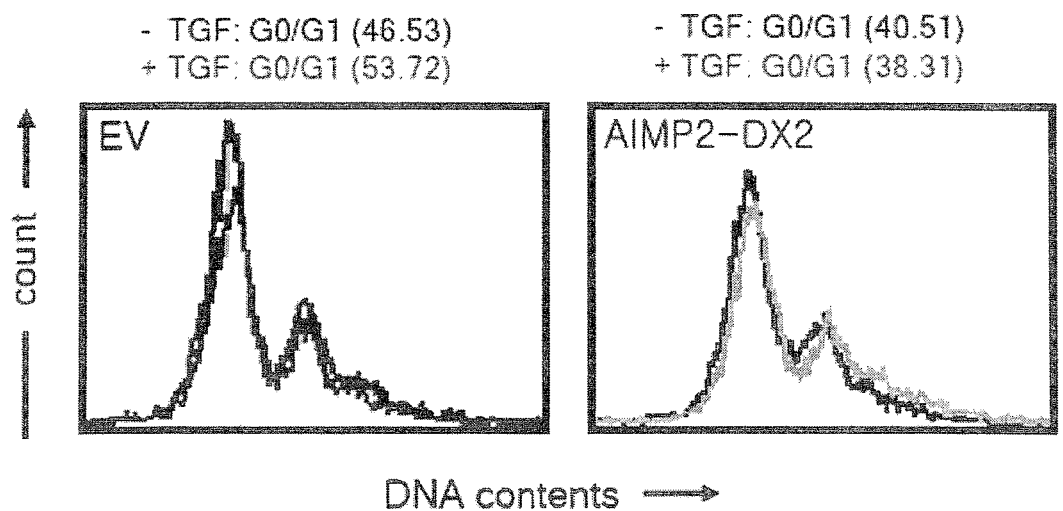
Figure 9D:
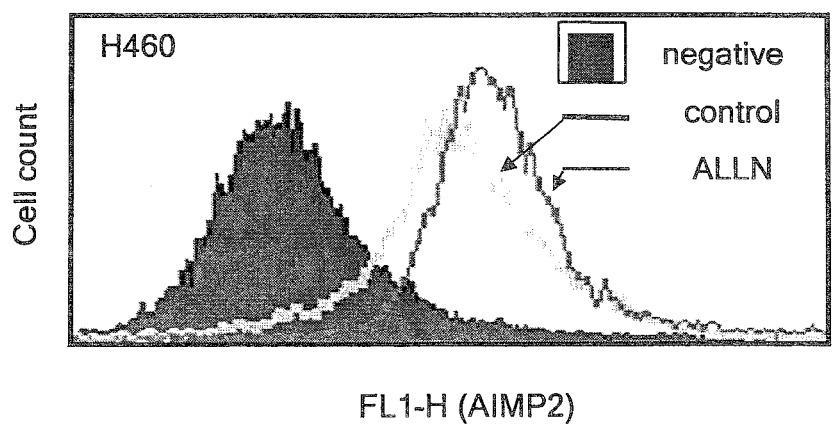

Western blot analysis with anti-AIMP2 antibody detected only the full-length AIMP2, but not AIMP2-DX2 (FIG. 2a), implying that AIMP2-DX2 may be very unstable at protein level. Immunofluorescence staining also demonstrated the lower AIMP2 level in H460, H322 and H290 (FIG. 3d). To exclude the possibility of staining artifact, we co-cultivated H460 and DU145 cells in the same plate and stained AIMP2. Again, the staining intensity of AIMP2 in H460 was much weaker than that in DU145 (FIG. 9a). In addition, the TGF-β-dependent nuclear localization of AIMP2 was not observed in the cells with low AIMP2 expression (FIG. 9d, bottom row). To address the linkage between the AIMP2 level and functionality of TGF-β, we measured growth suppression by TGF-β in these cell lines. While the growth of A549 and DU145 cells was suppressed by TGF-β, the cells with low AIMP2 level did not respond to TGF-β (FIG. 9e). This result is consistent with previous reports that A549 is sensitive whereas H460 is resistant to TGF-β signal (Osada, H. et al. Cancer Res. 61, 8331-8339 (2001); Kim, T. K. et al., Lung Cancer 31, 181-191 (2001)). In addition, the target genes were induced by TGF-β in A549 and DU145, but not in H322 and two other cell lines with low AIMP2 (FIG. 3f).

Furthermore, we tested by RT-PCR whether other cancer cell lines generates AIMP2-DX2. As a result, it was revealed that AIMP2-DX2 was detected in SaOS2 (osteosarcoma) and MCF7 (breast adenocarcinoma cell).

The Inactive Deletion Variant Forms a Complex with Functional AIMP2

Figure 4A:
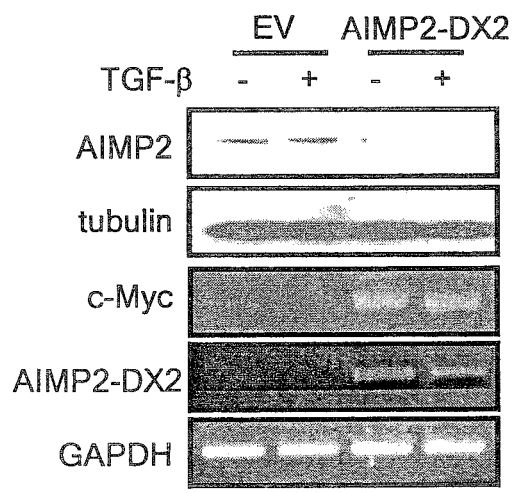
FIGS. 4a-4h demonstrates the Effect of AIMP2-DX2 on the cellular stability of AIMP2.
Figure 4B:
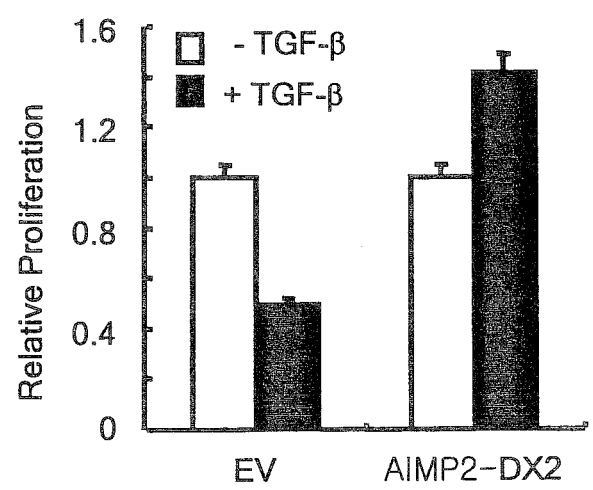
Figure 4C:
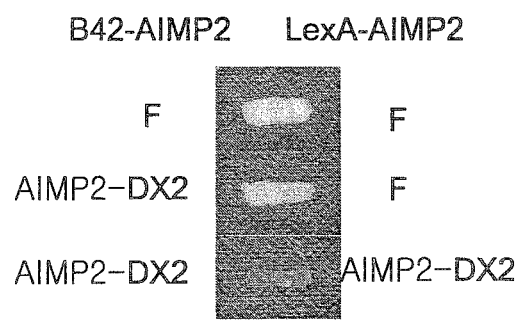
Figure 4D:
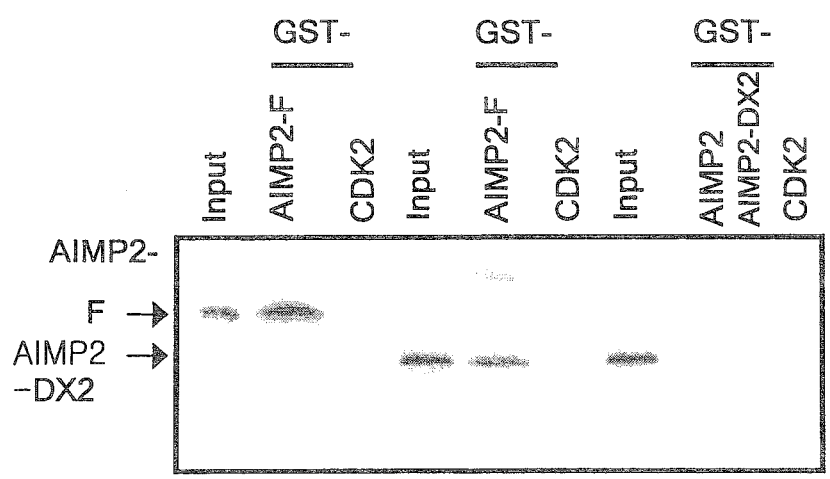
Figure 4E:
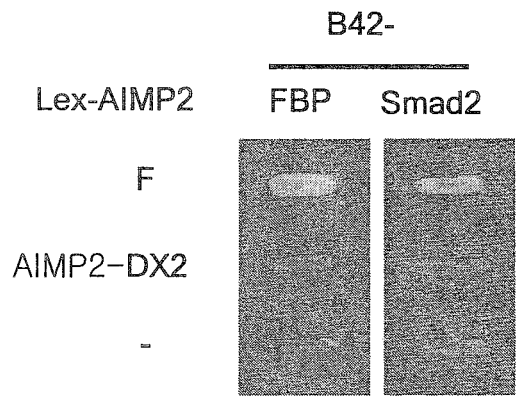

To comprehend the causal relationship of the AIMP2-DX2 generation and suppression of AIMP2, we checked the change of the AIMP2 level after transfection of AIMP2-DX2 into DU145. AIMP2 was reduced in the AIMP2-DX2-transfected cells, as demonstrated by Western blot (FIG. 4a, first row) and FACS analyses (FIG. 9b). Moreover, the expression of the AIMP2 target, c-myc, was elevated by the introduction of AIMP2-DX2 (FIG. 4a, third row). AIMP2-DX2 also relieved the growth arrest by TGF-β (FIGS. 4b and 9c). We then investigated how AIMP2-DX2 would affect the functional AIMP2 (AIMP2-F). Since AIMP2 has a potential to form a homodimer (Quevillon, S. et al., J. Mol. Biol. 285, 183-195 (1999); and Kim, J. Y. et al., Proc. Natl. Acad. Sci. USA 99, 7912-7916 (2002)), we examined whether AIMP2-DX2 would interact with AIMP2-F by yeast two hybrid assay. AIMP2-DX2 showed the interaction with AIMP2-F, but not with itself (FIG. 4c). In in vitro pull-down assay, both of radioactively synthesized AIMP2-F and AIMP2-DX2, but not AIMP2-DX2, were co-purified with GST-AIMP2-F (FIG. 4d), proving the direct interaction between AIMP2-F and AIMP2-DX2. To see whether AIMP2-DX2 is active in TGF-β signaling, we tested its interaction with Smad2 by yeast two hybrid assay. While AIMP2 interacted with Smad2 as well as FBP that is the known target of AIMP2 (Kim, M. J. et al., Nat. Genet. 34, 330-336 (2003)), AIMP2-DX2 did not bind to any of these proteins, suggesting that it would be functionally inactive (FIG. 4e).

Figure 4F:
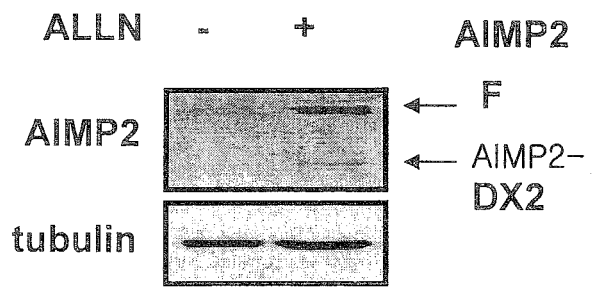
Figure 4G:
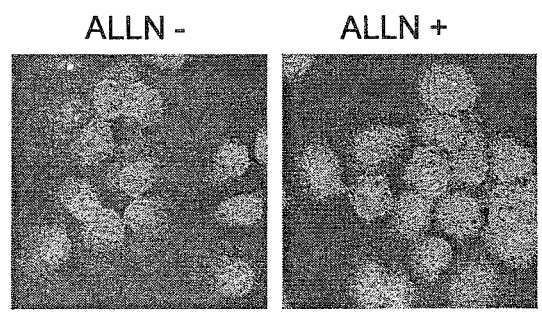
Figure 4H:
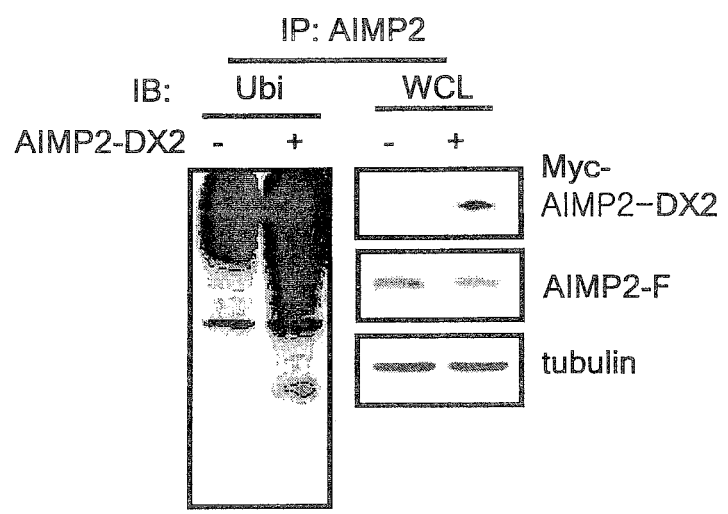

To understand how the heterodimer formation would suppress AIMP2, we checked whether the AIMP2 level is controlled by proteasome-dependent degradation process. The AIMP2-DX2-producing H322 cells were treated with the proteasome inhibitor, ALLN (Zhou, M., et al., J. Biol. Chem. 271, 24769-24775 (1996)) and tested whether the AIMP2 level is increased by the blockage of proteasome. The AIMP2 level was significantly increased by the treatment of ALLN as shown by Western blotting (FIG. 4f), immunofluorescence staining (FIG. 4g) and flow cytometry (FIG. 9d), suggesting that its cellular level would be controlled by proteasome-mediated degradation. In addition, AIMP2-DX2 form was also detected by the inhibition of proteasome (FIG. 4f), confirming the notion that AIMP2-DX2 would be unstable due to the rapid proteasome-dependent degradation. The low intensity of AIMP2-DX2 appears to result from its lower transcription compared to the normal AIMP2, as demonstrated by RT-PCR analysis (FIG. 3c) and/or less efficient recognition by anti-AIMP2 antibody. Since AIMP2 degradation is mediated by proteasome, we tested whether its ubiquitination is promoted by AIMP2-DX2. When AIMP2 was immunoprecipitated from the control and AIMP2-DX2-transfected cells that were treated with ALLN and blotted with anti-ubiquitin antibody, higher amount of the ubiquitinated AIMP2 was observed in the AIMP2-DX2-transfected cells compared to that in control cells (FIG. 4h). Combined together, AIMP2-DX2 appears to work as a dominant negative mutant to form an inactive complex with AIMP2 that is rapidly driven to degradation process.

AIMP2-DX2 Inactivates TGF-β Signaling and Promotes Cell Growth

Figure 5A:
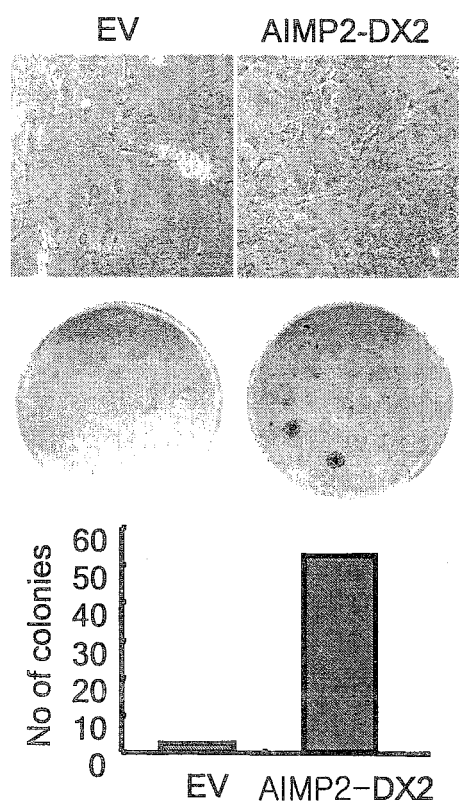
FIGS. 5a-5e represent the disruptive effect of AIMP2-DX2 on cell growth control and TGF-β signaling.
Figure 5B:
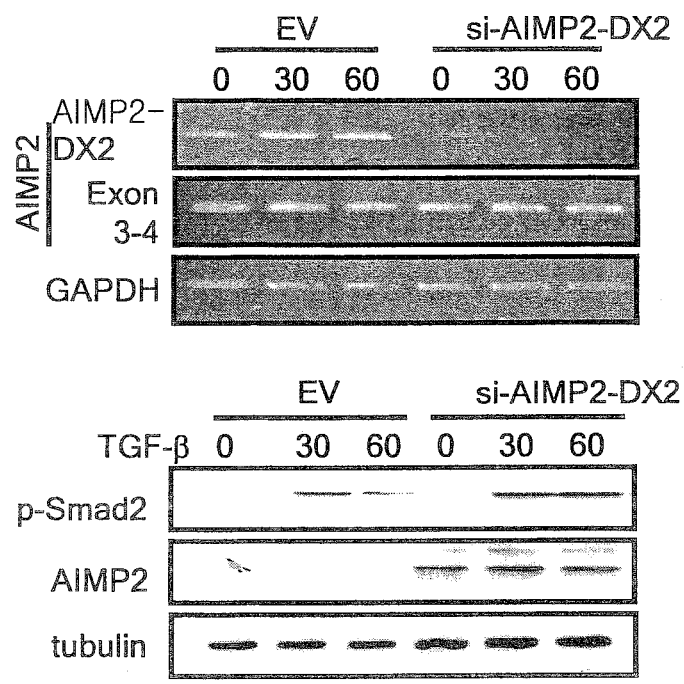
Figure 5C:
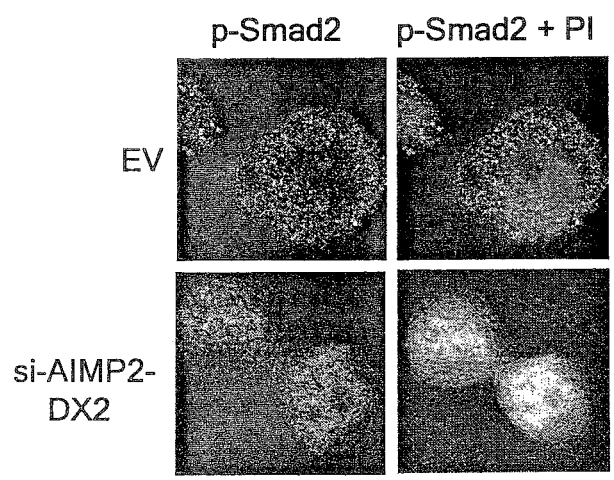
Figure 5D:
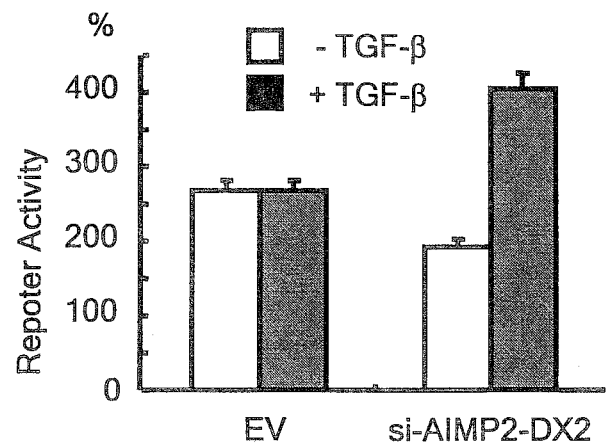
Figure 5E:
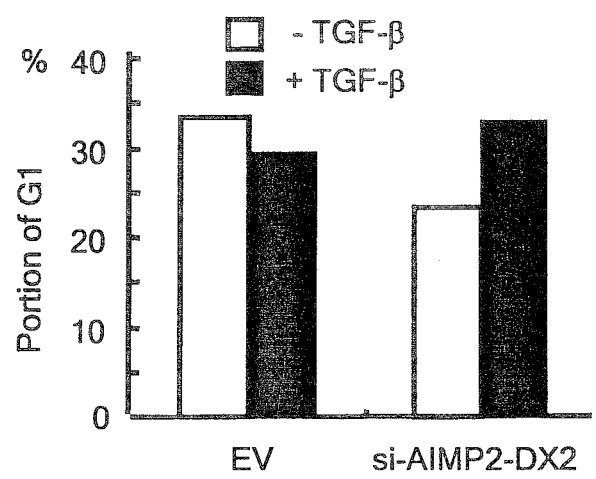

We transfected AIMP2-DX2 into MEFs and monitored its effect on cell growth by microscopic analysis and colony formation. The cell growth was significantly enhanced by the introduction of AIMP2-DX2 (FIG. 5a). We then introduced siRNA (si-AIMP2-DX2) that specifically suppresses the AIMP2-DX2 transcript and checked whether it can restore the normal level of AIMP2 and TGF-β signaling in H322 cells expressing AIMP2-DX2. si-AIMP2-DX2 ablated the AIMP2-DX2 transcript (FIG. 5b top) and resumed the normal AIMP2 level and TGF-β-induced phosphorylation of Smad2 (FIG. 5b bottom), nuclear localization of p-Smad2 (FIG. 5c), TGF-β-dependent reporter expression (FIG. 5d) and growth arrest (FIG. 5e). All of these results demonstrated the disruptive effect of AIMP2-DX2 on TGF-(3 signaling and cell growth control.

Association of AIMP2 Deletion Variant with Human Lung Cancer

Figure 6A:
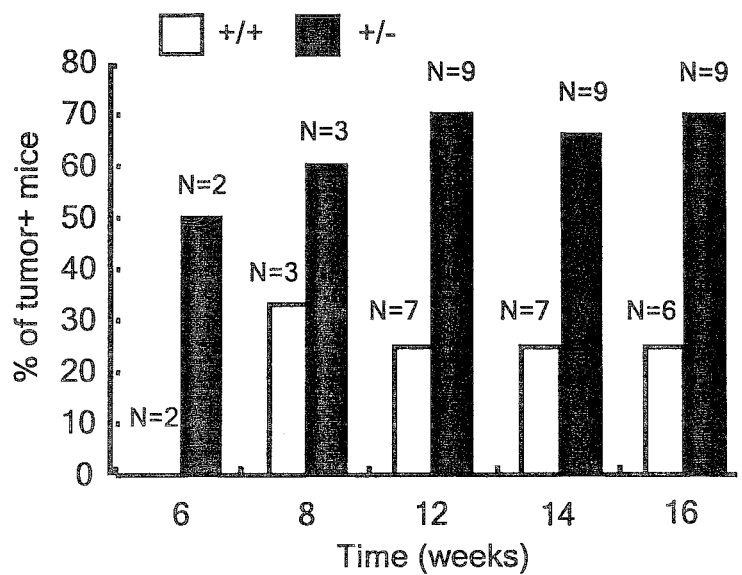
FIGS. 6a-6c represent the association of AIMP2 with lung cancer formation.
Figure 6B:
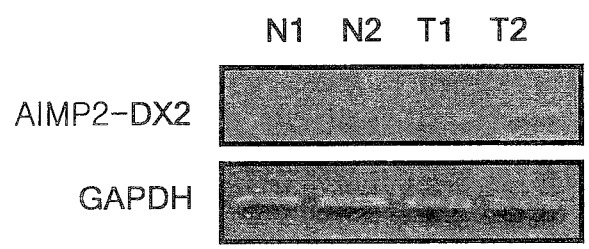
Figure 6C:
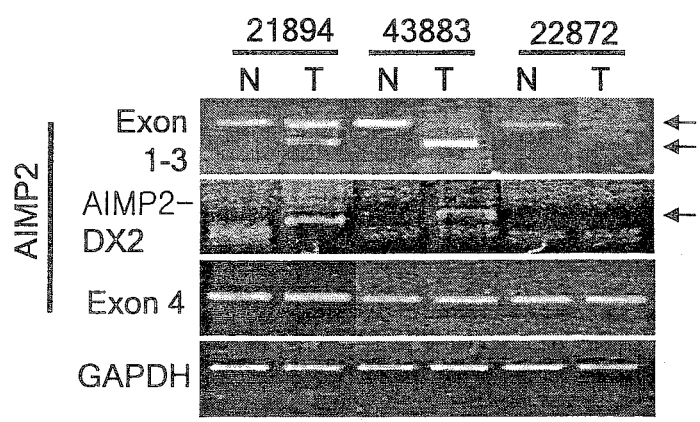
Figure 10:
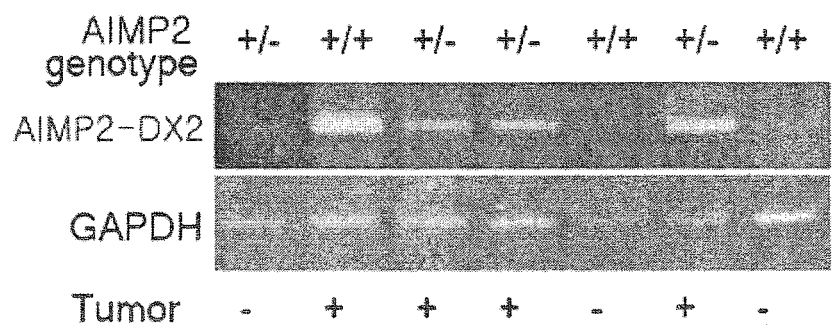
FIG. 10 shows the generation of AIMP2-DX2 and suppression of AIMP2 in lung cancer tissues. Lungs were isolated from the AIMP2$^{+/+}$ and AIMP2$^{+/-}$ mice injected with benzoypyrene, and RNAs were isolated from each lung for RT-PCR to determine the generation of AIMP2-DX2. All of the lungs generating AIMP2-DX2 showed tumor formation in lung (marked +).

Since the reduction of AIMP2 is frequently detected in different cancer cell lines (FIGS. 3a, 3b and 3d), and loss of AIMP2 leads to hyper-proliferation of lung cells (Kim, M. J. et al., Nat. Genet. 34, 330-336 (2003)), we examined the association of AIMP2 abnormality with lung cancer formation. We induced lung tumor through the intraperitoneal injection of chemical carcinogen, benzo-(α)-pyrene (BP, Wang, Y. et al., Cancer Res. 63, 4389-4395 (2003)) into AIMP2$^{+/+}$ and AIMP2$^{+/-}$ mice, and monitored the tumor formation in lung. From 6 weeks after the administration of BP, lung tumors were observed at 50-70% frequency in AIMP2$^{+/-}$ mice, and at about 30% in the wild type littermates (FIG. 6a), implying that the heterozygous mice are more susceptible to BP-induced tumorigenesis. We examined whether AIMP2-DX2 is generated in the lungs of the BP-injected mice. Three out of four lungs isolated from AIMP2$^{+/-}$ mice showed tumors, while only one developed tumors among three AIMP2$^{+/+}$ mice and all of these tumors generated AIMP2-DX2 (FIG. 10), further supporting the relevance of AIMP2-DX2 to tumor formation. Moreover, AIMP2-DX2 was generated only in tumor tissues (FIG. 6b). To exclude the possibility that the AIMP2 level and AIMP2-DX2 formation may vary depending on different individuals, we carried out RT-PCR analyses in the normal and tumor pairs isolated from the same patients. Again, the cancer-specific reduction of AIMP2 was coupled with the generation of AIMP2-DX2 (FIG. 6c). AIMP2-DX2 was not detected in one case showing the normal AIMP2 level in cancer region (FIG. 6c, patient 22872). We further examined 10 different pathologically-diagnosed lung adenocarcinoma, squamous cell carcinoma and large cell adenocarcinoma samples, and observed the cancer-specific reduction of AIMP2 and generation of AIMP2-DX2 in 8 cases (Table 1). Although AIMP2-DX2 was detected in the histologically normal regions in two cases, its occurrence was still coupled with the low level of AIMP2.

TABLE 1

The relationship between AIMP2 level and AIMP2-DX2 generation in different lung cancer patients

| No | Code (MLLG) | Cell type | Opdate | Recur | Sex | Age | AIMP2-F N | AIMP2-F T | AIMP2-DX2 N | AIMP2-DX2 T |
|----|------|-----|----------|-------|---|----|---|---|---|---|
| 1 | H004 | SQC | 01-06-26 | FALSE | M | 64 | + | − | − | + |
| 2 | H008 | ADC | 01-09-26 | FALSE | M | 62 | + | − | − | + |
| 3 | H001 | ADC | 01-12-14 | FALSE | M | 68 | + | − | − | + |
| 4 | H010 | SQC | 01-12-26 | FALSE | M | 56 | + | − | − | + |
| 5 | H018 | ADC | 02-04-26 | FALSE | M | 60 | − | − | + | + |
| 6 | H021 | ADC | 02-05-07 | TRUE  | F | 64 | − | − | + | + |
| 7 | H024 | ADC | 02-05-17 | FALSE | F | 59 | + | − | − | + |
| 8 | H025 | SQC | 02-05-28 | FALSE | M | 73 | + | − | − | + |
| 9 | H029 | ADC | 02-06-14 | FALSE | M | 67 | + | − | − | + |
| 10 | H031 | LAC | 02-07-08 | FALSE | M | 71 | + | − | − | + |

Positive (+) and negative (−) in the AIMP2-F column denote the immunofluorescence staining of AIMP2 in normal (N) and tumor (T) tissues determined by histological analysis.
Positive and negative in AIMP2-DX2 column indicate the generation of AIMP2-DX2 that was determined by RT-PCR.
Note for abbreviations:
Recur (recurrence),
SQC (squamous cell carcinoma),
ADC (adenocarcinoma),
LAC (large cell adenocarcinoma) and
Opdate (operation date).

Association of AIMP2 and its Deletion Variant with Human Liver Cancer

Figure 11:
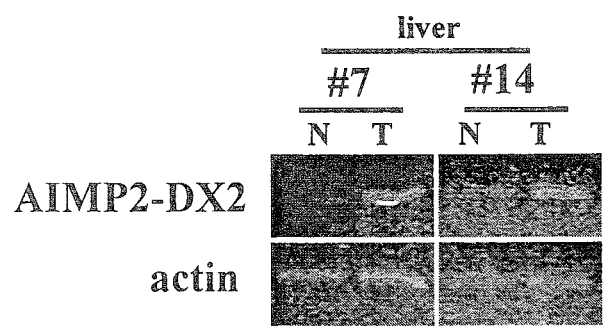
FIG. 11 represents the expression of AIMP2-DX2 and suppression of AIMP2 in liver cancer tissues. RT-PCR was performed to determine the expression of AIMP2-DX2 in liver cancer tissues.

We examined the relationship of AIMP2 or its deletion variant with human liver cancer using human tissues. The formation of AIMP2-DX2 was evaluated in normal and cancer tissue (hepatocellular carcinoma) by RT-PCR and the level of AIMP2 by immunofluorescence analyses as described previously. As a result, AIMP2-DX2 was detected in live cancer tissues (FIG. 11).

Increased Susceptibility of AIMP2$^{+/-}$ Mice to Tumorigenesis and Expression of its Splicing Variant.

Figure 13A:
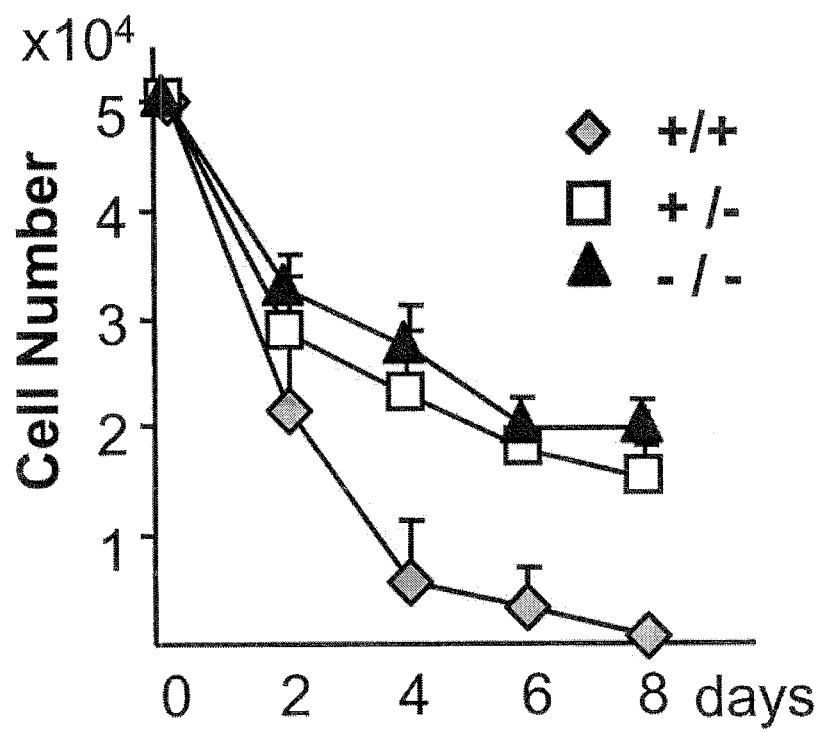
In FIG. 13a, apoptotic sensitivity of AIMP2 WT, hetero- and homozygous MEFs was compared by the cell count after the treatment of benzopyrene (BP) at time interval.
Figure 13B:
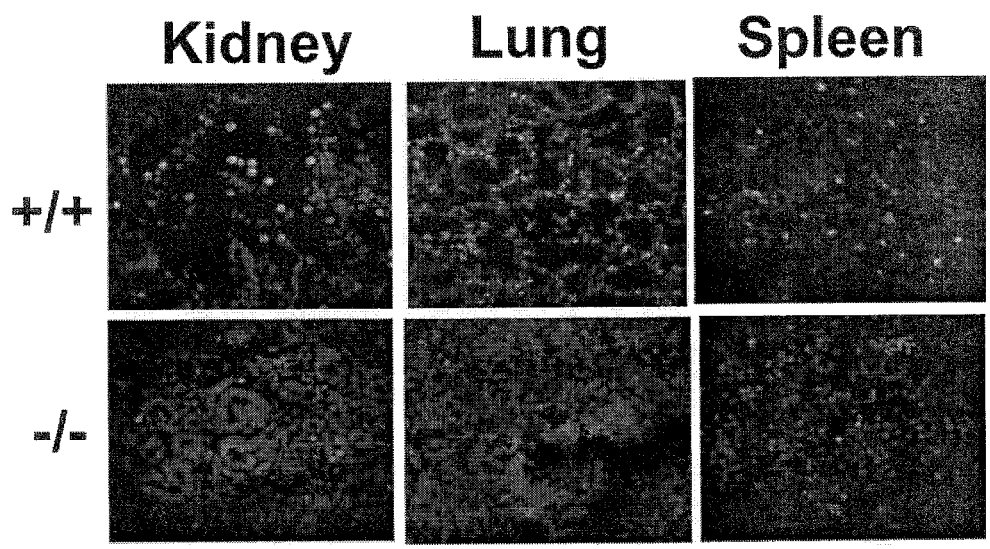
In FIG. 13b, apoptotic cells were visualized (×100) by Apoptag staining in different tissues isolated from AIMP2$^{+/+}$ and AIMP2$^{-/-}$ neonatal mice.
Figure 13C:
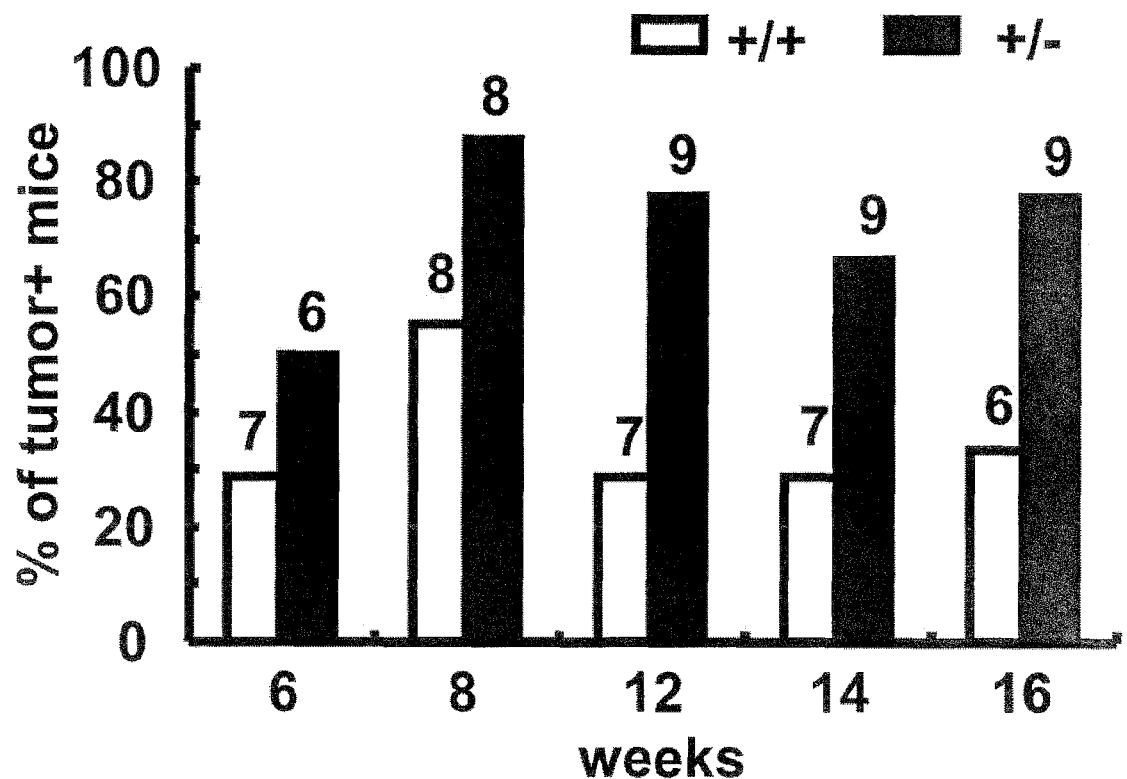
In FIG. 13c, tumor susceptibility of AIMP2$^{+/+}$ and AIMP2$^{+/-}$ mice was compared by lung tumorigenesis induced by BP. From 6 weeks after the BP treatment, lungs were isolated and tumor formation was determined at the indicated times. Numbers on the bar indicate the number of the examined mice.
Figure 13D:
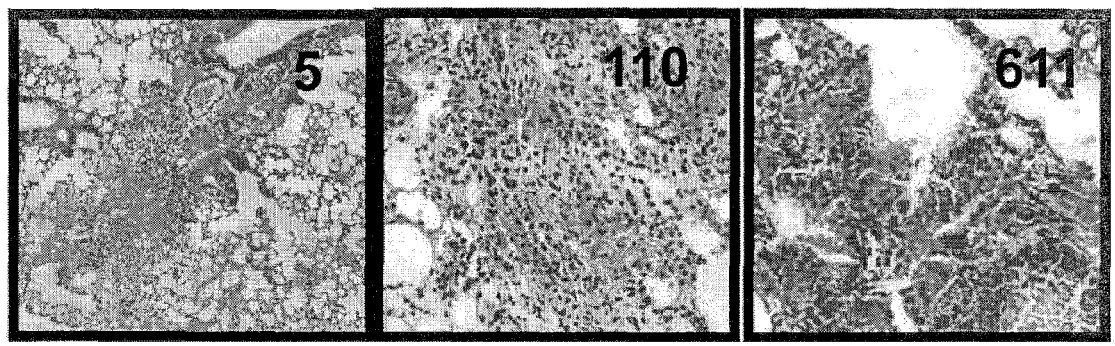
FIG. 13 shows increased susceptibility of AIMP2$^{+/-}$ mice to tumorigenesis and expression of its splicing variant.
In FIG. 13e, the relative expression of AIMP2-DX2 and -F were determined in adenocarcinoma (n=14) and normal (n=11) lung tissues by quantitative real-time RT-PCR. The cancer regions were obtained by laser microdissection system from archival formalin-fixed paraffin-embedded (FFPE) patient tissues for RT-PCR as described in Methods. Poly-A polymerase alpha (PAPOLA) was chosen as the reference gene for quantitative RT-PCR. The expression results were analyzed by Mann-Whitney test and statistical analyses were achieved using SPSS software (SPSS, Chicago, Ill.). Each dot represents the expression ratio of AIMP2-DX2 to -F and mean values were shown. The mean differences of P<0.05 were considered significant.

The potential tumor suppressive activity of AIMP2 was tested by lung tumorigenesis induced by benzopyrene. We previously observed that AIMP2-deficient mice show higher cell proliferation (Kim, M. J., Park, B.-J., Kang, Y.-S., Kim, H. J., Park, J.-H. Kang, J. W., Lee, S. W., Han, J. M., Lee, H.-W., Kim, S. Downregulation of fuse-binding protein and c-myc by tRNA synthetase cofactor, p38, is required for lung differentiation. Nat. Genet. 34, 330-336 (2003)). Here we checked whether AIMP2−/− cells would also show difference in cell death. We prepared mouse embryonic fibroblasts from AIMP2 wild type, hetero- and homozygous mice and compared them in the resistance to cell death induced by a carcinogen, benzopyrene (BP), treatment. The number of AIMP2 wild type MEFs was more rapidly decreased than the hetero- and homozygous cells by the BP treatment (FIG. 13a). We also compared the number of apoptotic cells in different tissues isolated from the wild type and homozygous cells. The AIMP2-deficient tissues showed decreased apoptotic cells compared to the corresponding regions of the wild type mice (FIG. 13b). Thus, the AIMP2 depletion appears to render resistance to cell death. We then checked how AIMP2 would affect the in vivo susceptibility to lung tumorigenesis that is induced by BP. Since AIMP2$^{-/-}$ mice are neo-natal lethal due to lung disorder (Kim, M. J., Park, B.-J., Kang, Y.-S., Kim, H. J., Park, J.-H. Kang, J. W., Lee, S. W., Han, J. M., Lee, H.-W., Kim, S. Downregulation of fuse-binding protein and c-myc by tRNA synthetase cofactor, p38, is required for lung differentiation. Nat. Genet. 34, 330-336 (2003)), we decided to use the heterozygous mice. We induced lung tumorigenesis by intraperitoneal injection of BP as previously described (Wang, Y., Zhang, Z., Kastens, E., Lubet, R. A. & You, M. Mice with alterations in both p53 and Ink4a/Arf display a striking increase in lung tumor multiplicity and progression: differential chemopreventive effect of budesonide in wild-type and mutant A/J mice. Cancer Res. 63, 4389-4395 (2003)) and compared the frequency of the tumor formation from 6 weeks after BP injection. AIMP2$^{+/-}$ mice developed lung tumors at about 2 fold higher frequency than the wild type littermates (FIGS. 13c and d). These results suggest pro-apoptotic and tumor suppressive activities of AIMP2.

Noticeable was that AIMP2-DX2 was more highly expressed in lung cancer cell lines (A549, H322, H460 and H157) than in normal cells (WI-26 and NL-20), implying its potential association with cancer formation. To confirm this possibility, we separated cancer and normal tissues from adenocarcinoma lung cancer patients by laser micro-dissection, isolated RNAs and then conducted quantitative real-time RT-PCR to measure the relative expression of AIMP2-DX2 to AIMP2-F. The expression of AIMP2-DX2 to AIMP2-F was generally higher in the cancerous regions compared to that of the normal counterparts (FIG. 13e). Higher expression of AIMP2-DX2 was also observed at high frequency in other lung cancer types (data not shown).

Oncogenic Property of AIMP2-DX2.

Figure 14A:
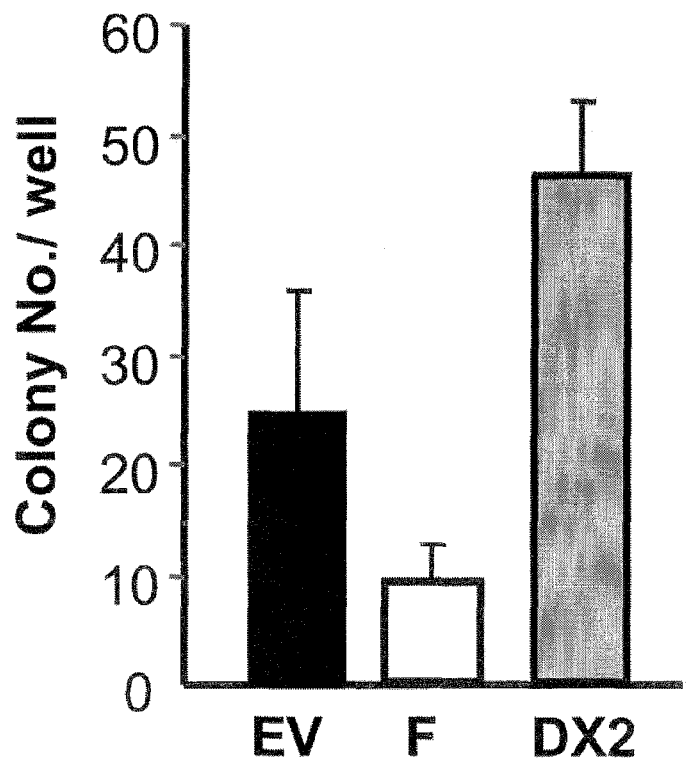
In FIG. 14a, mouse embryonic fibroblasts were transfected with EV (empty vector), AIMP2-F and -DX2 and selected by G418 to establish the stable cell lines. The colonies were selected from each transfectants and their ability to form anchorage-independent colonies was determined and represented as bar graph.
Figure 14B:
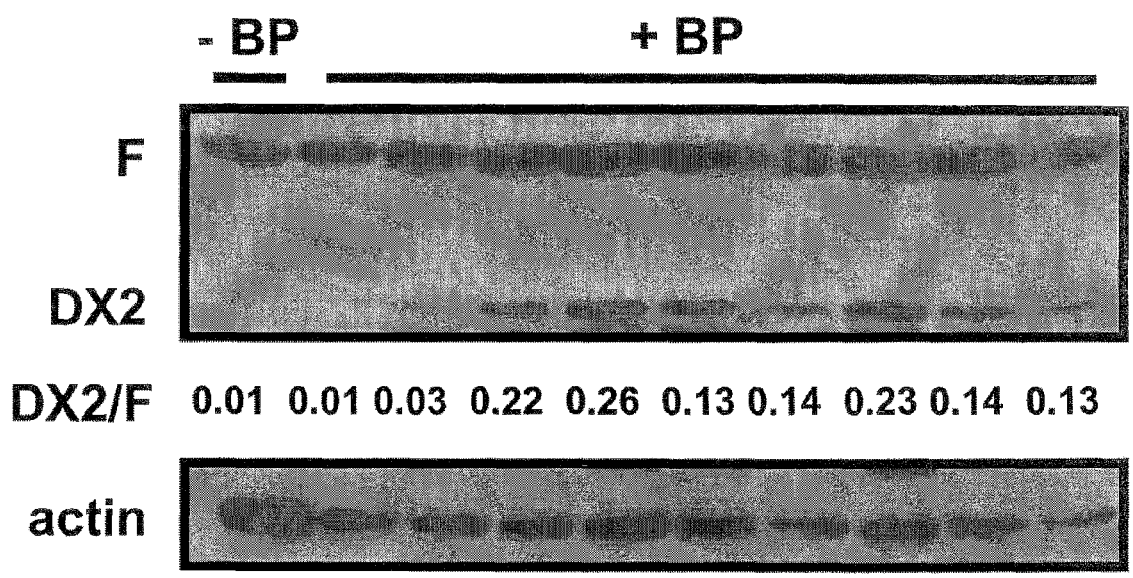
In FIG. 14b, normal lung WI-26 cells were incubated in the presence of BP for 4 weeks. The surviving cells were further cultivated for another 4 weeks after removal of BP and the colonies were isolated. The expression of AIMP2-F and -DX2 in each isolated colonies was determined by Western blotting with anti-AIMP2 antibody. The ratios of AIMP2-DX2 to -F were shown.
Figure 14C:
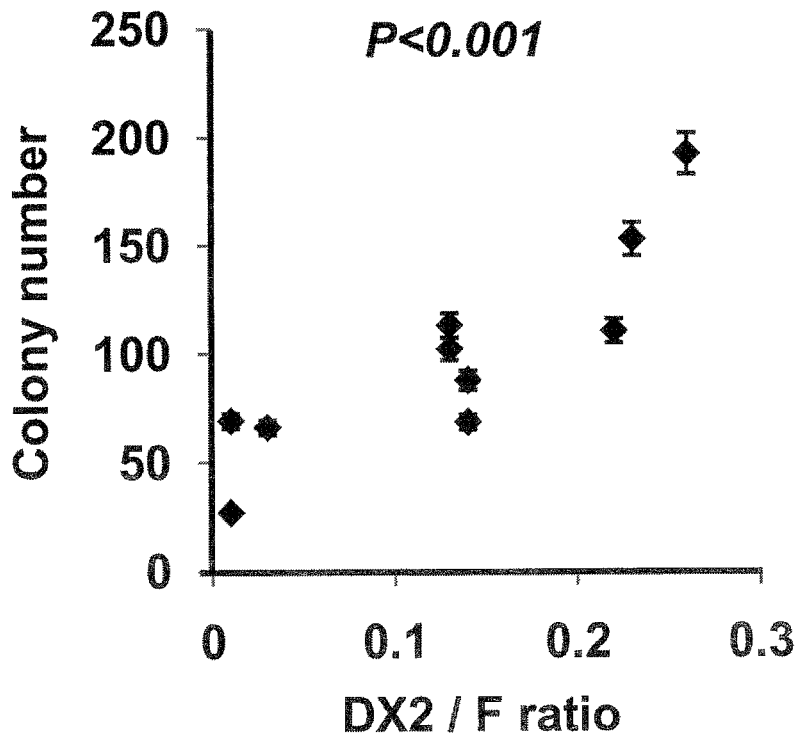
In FIG. 14c, the same numbers of the isolated colonies were plated and incubated to determine their ability to form anchorage-independent colony formation. The relationship between the ratio of AIMP2-DX2/F and the number of the resulting colonies was displayed as dot plot.
Figure 14D:
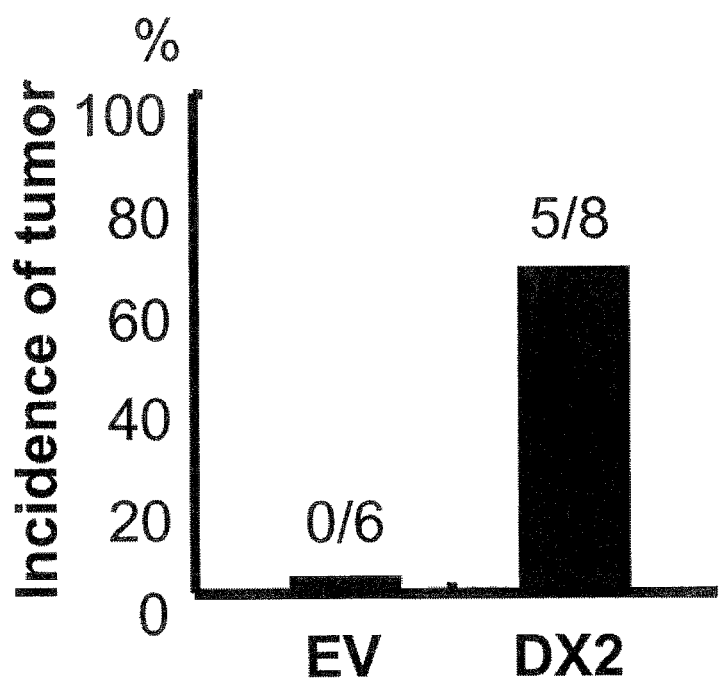
In FIG. 14d, mouse embryonic fibroblasts were transfected with EV or AIMP2-DX2, and the cell lines stably expressing AIMP2-DX2 were established by G418 selection. The same numbers of the selected colonies were then injected to nude mice and checked their ability to form tumors. Among eight mice injected with AIMP2-DX2 transfectants, five mice generated tumors whereas none of the six mice injected with the empty vector transfectants formed tumors.
Figure 14E:
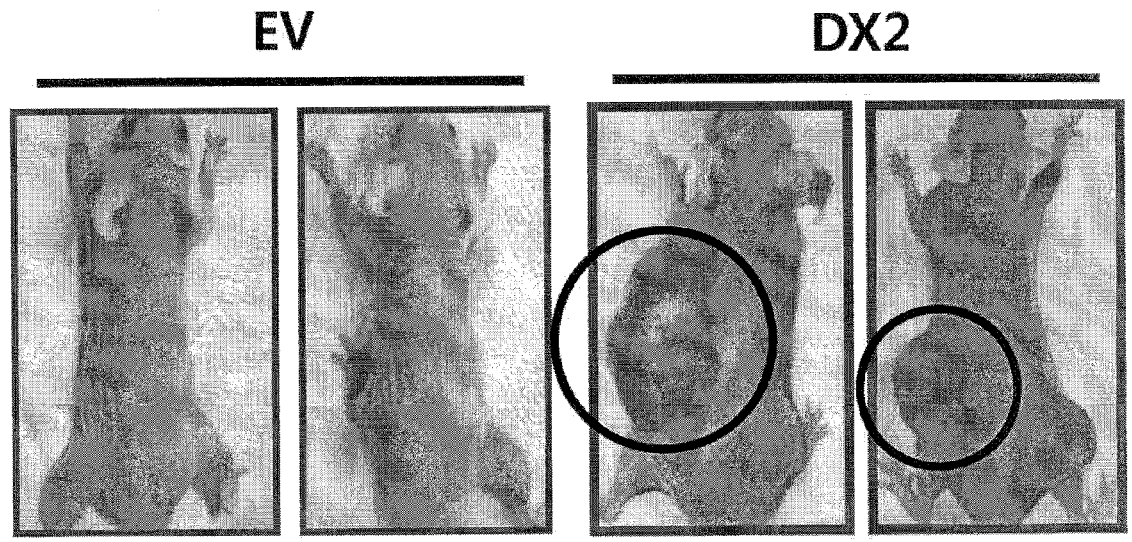
In FIG. 14e, a couple of the representative mice injected with the EV- or DX2-transfectants are shown.
Figure 14F:
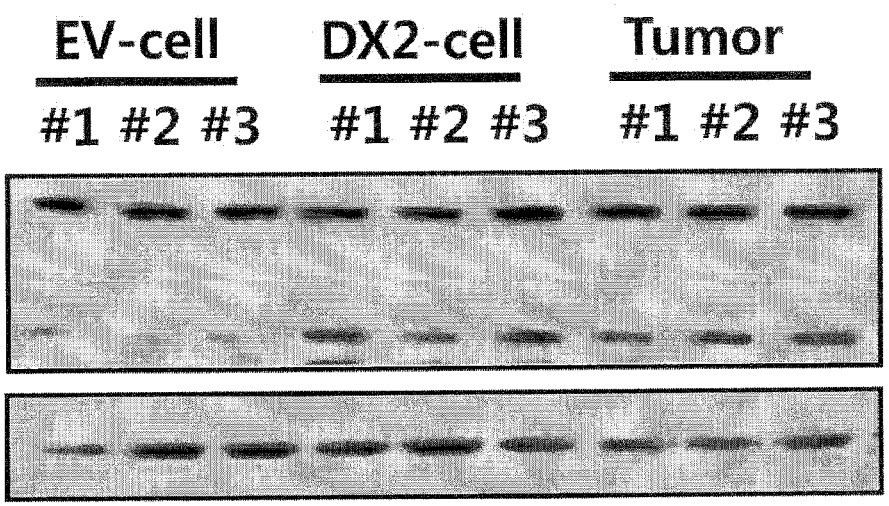
In FIG. 14f, the expression of AIMP2-F and -DX2 was determined by Western blotting with anti-AIMP2 antibody in the three EV and AIMP2-DX2 transfectants. The tumors resulting from the injection of the AIMP2-DX2 transfectant were obtained and the expression fm AIMP2-F and -DX2 was determined by Western blotting with anti-AIMP2 antibody.

We then checked whether high expression of AIMP2-DX2 can induce cell transformation by anchorage-independent colony formation assay. We introduced AIMP2-F or -DX2 into AIMP2-deficient MEFs and compared the number of the resulting colonies. While transfection of AIMP2-F generated fewer colonies than the empty vector, AIMP2-DX2 increased the colony formation (FIG. 14a). In another test, we used normal lung WI-26 cells in which AIMP2-DX2 level is very low or undetectable (FIG. 14b the left most lane), and incubated them in the presence of BP. We then selected the surviving colonies and checked whether these colonies have increased expression of AIMP2-DX2 by Western blotting. The most of the selected colonies expressed higher expression of AIMP2-DX2 compared to the control cells (FIG. 14b) although the ratio of AIMP2-DX2 to -F varied significantly depending on the cells (FIG. 14b). We then compared the selected colonies in their ability of anchorage-independent colony formation as above. The resulting colony numbers showed positive correlation to the expression ratio of AIMP2-DX2 to -F (FIG. 14c). We also introduced EV or AIMP2-DX2 into MEFs and established the stable cell lines by G418 selection. We then isolated three AIMP2-DX2-overexpression and three EV-transfected cell lines, and injected them to nude mice. Five out of the eight mice that were injected with the DX2-overexpression cell lines produced tumors whereas none of the six mice injected with the EV stable cells induced tumors (FIG. 14d-e). To confirm that high level expression of AIMP2-DX2 was still maintained in the tumors, we isolated the tumors that were formed from AIMP2-DX2 overexpression cells and re-examined the expression of this variant by Western blotting. All of the three examined tumors expressed AIMP2-DX2 at the level similar to their originally transplanted cells (FIG. 14f). All of these results support the potential oncogenic property of AIMP2-DX2. The results above suggest that the tumor suppressive activity of AIMP2-F would be compromised by the expression of DX2.

Knock-Down of AIMP2-DX2 Using si-RNA Suppresses Tumor Growth.

Figure 15B:
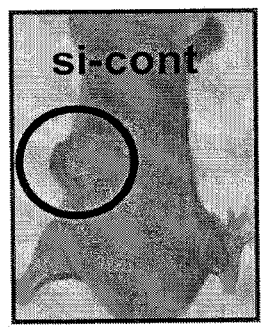
In FIG. 15b, the representative photographs of the si-control and -AIMP2-DX2-injected tumors growing on the nude mice.
Figure 15B:
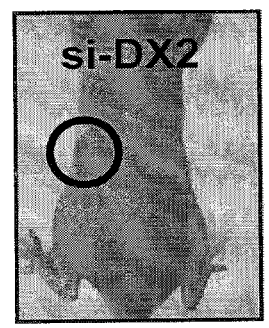
Figure 15C:
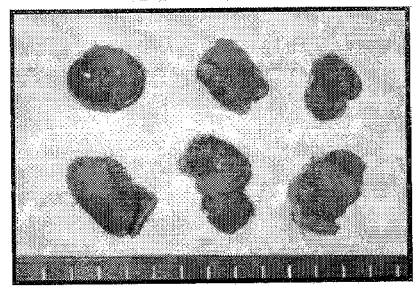
In FIG. 15c, the si-control and -AIMP2-DX2-injected tumors were isolated and their volumes are compared in the same scale. The scale unit represents 0.5 cm.
Figure 15C:
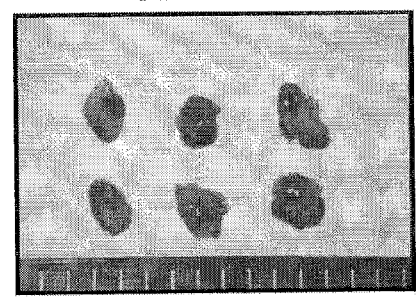
Figure 15D:
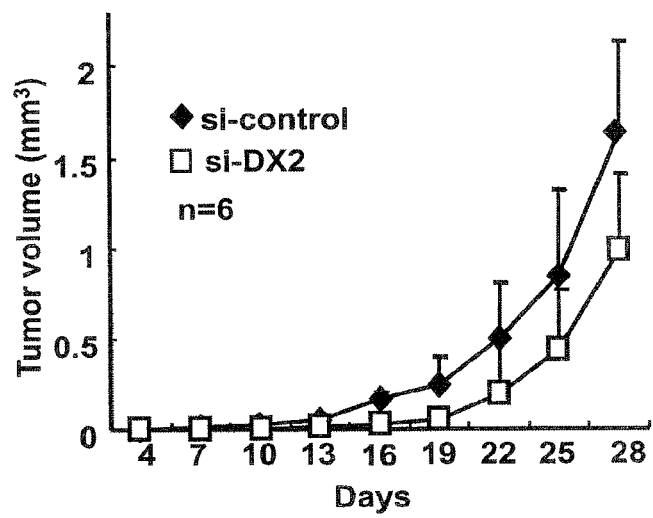
In FIG. 15d, the tumor growth of the si-control and -AIMP2-DX2 expressing H460 cells that were injected into the nude mice (n=6). The tumor volumes were measured at the indicated times.
Figure 15D:
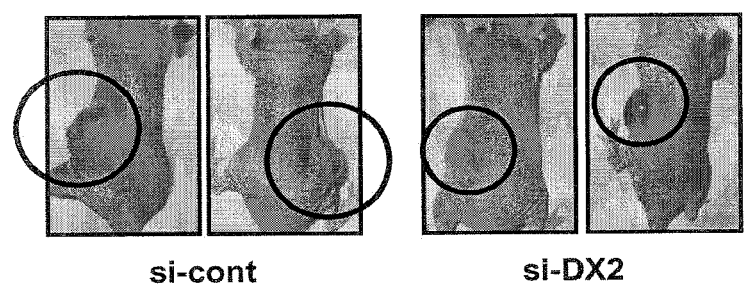
Figure 15E:
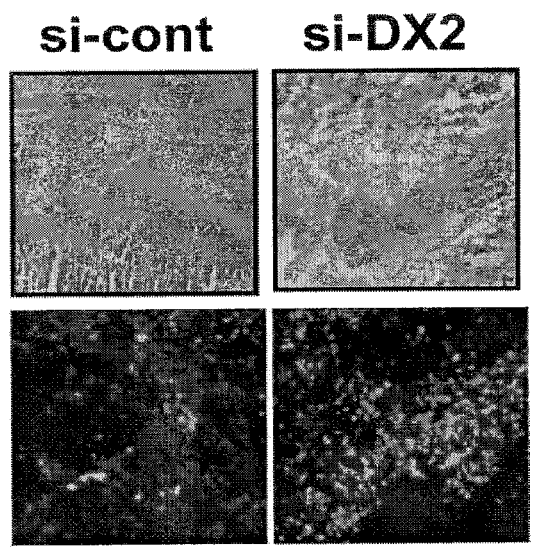
In FIG. 15e, the histological characteristics of the isolated tumors are compared by hematoxylin and eosin staining between si-control and -DX2 injected tumors (upper, ×100). The cell death between the two tumors was monitored by Apoptag staining (lower, ×100). The apoptotic cells and nuclei are shown in green and blue fluorescence, respectively.

We investigated whether tumor progression can be controlled by the suppression of AIMP2-DX2 expression. We introduced si-control or si-AIMP2-DX2 into lung cancer cell, NCI-H460, and transplanted the stable transfectants to nude mice and compared the tumor growth by measuring tumor volume at time interval. The si-AIMP2-DX2-transfected cells showed retarded tumor growth compared to the control tumors (FIG. 15d). To see whether additional administration of si-AIMP2-DX2 can further suppress the tumor growth, we directly injected si-control and si-AIMP2-DX2 into the growing tumors in 17, 21 and 23 days after the cell transplantation. The intratumoral injection of si-AIMP2-DX2 further suppressed tumor growth compared to the si-control-injected tumors as determined by tumor volume (FIG. 15a-c). We isolated tumors from si-control or si-AIMP2-DX2-treated mice after 28 days, and examined whether AIMP2-DX2 expression was actually suppressed by the delivery of si-AIMP2-DX2. We then isolated the si-control and -DX2-treated tumors and compared the cell density and death by histological analyses and Apoptag staining. The si-AIMP2-DX2-treated tumors showed less compact histological characteristics (FIG. 15e upper) and higher apoptotic cell population (FIG. 15e lower) than the si-control treated tumors, implying that the cell death should occur more actively in the AIMP2-DX2-suppressed tumors.

Figure 15F:
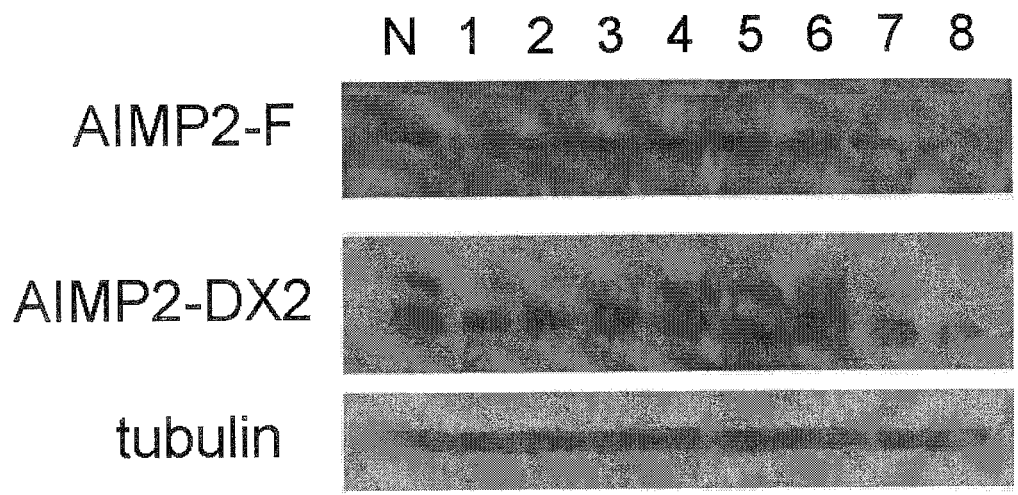
In FIG. 15f, the si-control and si-AIMP2-DX2 of Table 1 were transfected H460 cells, respectively, and expression of AIMP2-F and AIMP2-DX2 were determined by western blotting with monoclonal antibody (clone number 324).

We transfected si-control or si-AIMP2-DX2 of Table 1 into H460 cell, and compared the expression of AIMP2-F and AIMP2-DX2 using western blot with AIMP2-DX2 monoclonal antibody (clone number 324). As a result, AIMP2-DX2 expression was reduced in H460 cell by treating si-AIMP2-DX2 of Table 1 (FIG. 15f). The immunoglobulin isotype of AIMP2-DX2 monoclonal antibody (clone number 324) is IgG, and its epitope is from $84^{th}$ to $225^{th}$ of SEQ ID NO:2.

Delivery of GFP-Expressing Plasmid to the Various Parts of Mouse Lung Via Intranasal Inhalation.

Figure 16A:
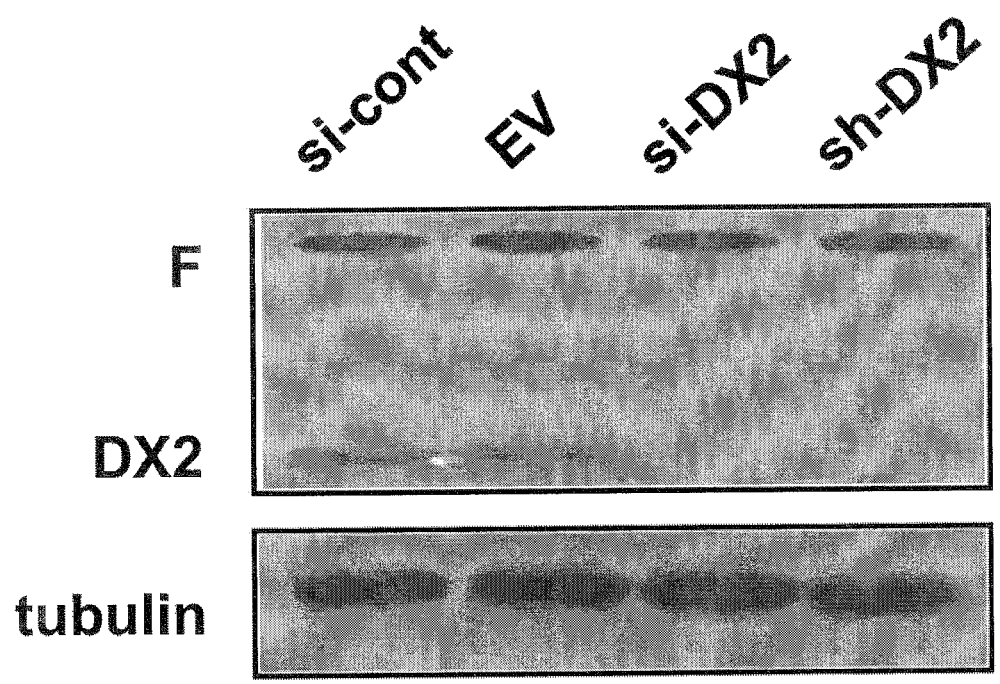
In FIG. 16a, the efficiency of si-AIMP2-DX2 and sh-AIMP2-DX2 in the suppression of AIMP2-DX2 was compared by Western blotting with anti-AIMP2 antibody. The siRNA targeting AIMP2-DX2 and the plasmid encoding sh-AIMP2-DX2 were introduced into A549 cells.
Figure 16B:
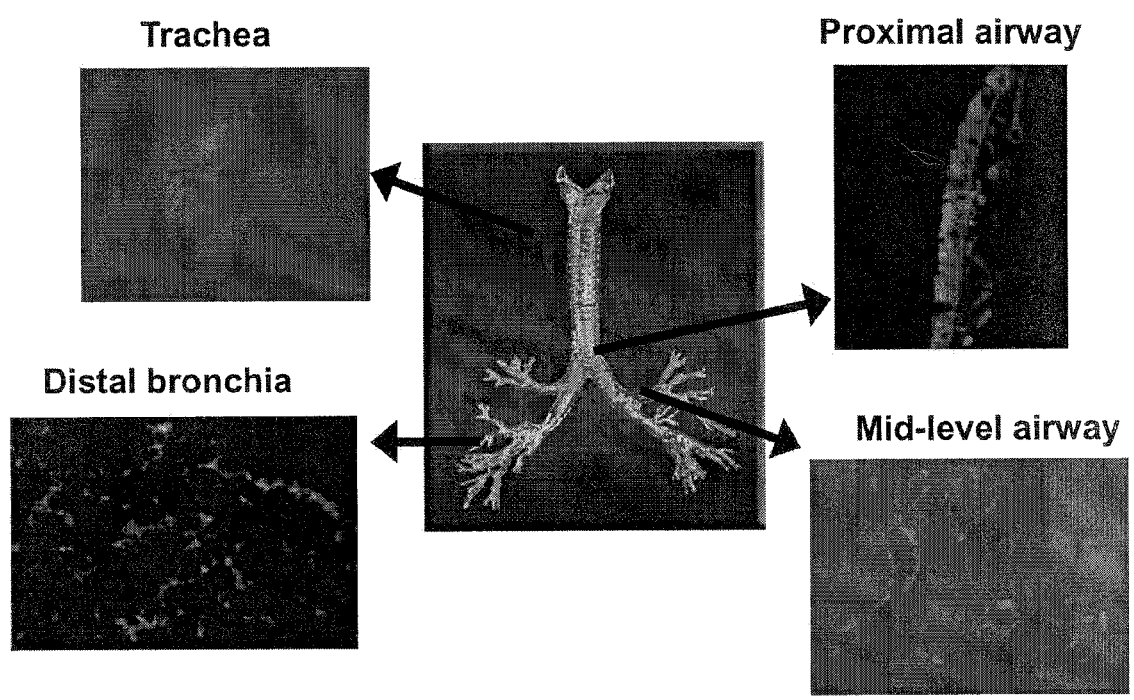
In FIG. 16b-c, GFP-encoding plasmid was delivered into mouse lung via intranasal inhalation as described. After 2 days, the mice were sacrificed and various regions of the lungs were fixed by paraffin block. The plasmid delivery was then monitored by fluorescence. About 50% of the examined lung area was evaluated as GFP positive.
Figure 16C:
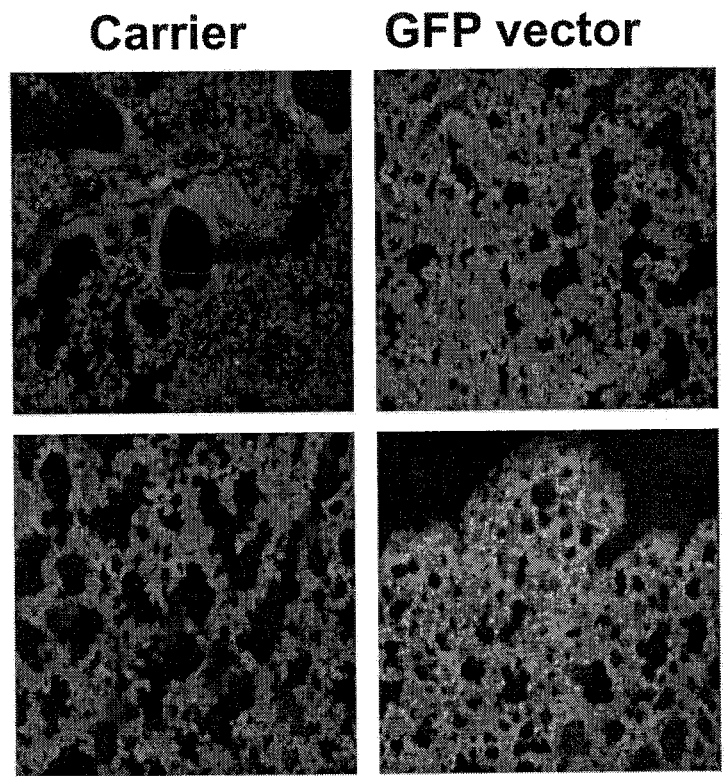

Since benzopyrene (BP) induces AIMP2-DX2 expression and lung tumors, we tested whether suppression of AIMP2-DX2 can retard the growth of the BP-induced tumors. For the experiment, we constructed the plasmid encoding shRNA (short hairpin RNA) suppressing AIMP2-DX2 and checked whether it can also retard tumor growth. The expressed shRNA specifically suppressed the expression of AIMP2-DX2, but not AIMP2-F, as determined by Western blotting of AIMP2 (FIG. 16a). For the delivery of the sh-AIMP2-DX2-encoding plasmid into lung, we used the nasal inhalation system that we previously used for the delivery of the plasmid encoding tumor suppressor PTEN (Kim, H. W., et al. Aerosol delivery of glucosylated polyethylenimine/phosphatase and tensin homologue deleted on chromosome 10 complex suppresses Akt downstream pathways in the lung of K-ras null mice. Cancer Res. 64, 7971-7976 (2004)). We checked the delivery efficiency of the plasmid DNA into various parts of lung by the expression of green fluorescence protein (GFP) encoded by the same plasmid. The GFP-plasmid was mixed with glucosylated PEI and the DNA vapor was generated by sonication in microwave chamber as previously described. After the inhalation, the mice were sacrificed and expression of GFP was examined in various regions of airway and lung alveoli. Most of the isolated tissues showed GFP expression (FIGS. 16b and c).

Knock-Down of AIMP2-DX2 Using sh-RNA Suppresses Tumor Growth.

Figure 17A:
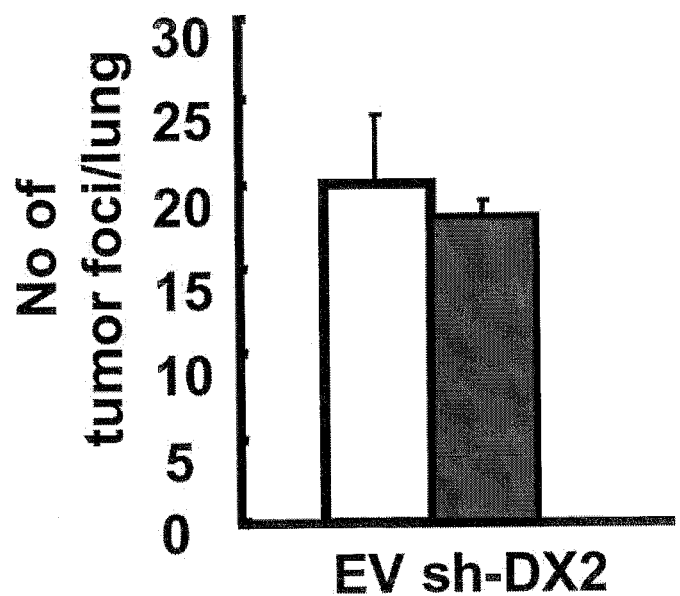
FIG. 17 shows knock-down of AIMP2-DX2 using sh-AIMP2-DX2 suppresses tumor growth. The lung tumors were induced by BP and the EV and sh-AIMP2-DX2 plasmids were delivered via nasal inhalation. After four weeks of the inhaled therapy, lungs were isolated and the number of tumor nodules (a) and tumor area (b) were determined after hematoxylin and eosin staining.
In FIG. 17c, the arrow heads indicate tumor nodules of the isolated lung lobes (upper) and the representative tumor area of the EV- and sh-DX2 treated lungs (lower).
In FIG. 17d, the CT (top) and micro-PET (middle) scanning images were superimposed (bottom) to locate tumor region. The tumor sizes were determined by standardized uptake values (SUVs) of radioactive FDG as described in methods. Numbers indicate different mouse id.
In FIG. 17e, the effect of sh-AIMP2-DX2 and EV plasmid delivery on the growth of lung tumors (n=2) was monitored by micro-PET analysis as described in Methods. The tumor sizes were reflected by standardized uptake values (SUVs) (shown in the table) using radioactive [18F] fluoro-2-deoxy-D-glucose (18FDG). The SUV values measured after the DNA delivery were divided by those before the treatment.
In FIG. 17f, the lung tumors were induced by BP treatment that was accompanied by butylhydroxyltoluene to boost tumor progression. The effect of sh-AIMP2-DX2 on the survival of tumor-containing mice was determined after the last DNA administration at time interval and represented as line graph.
Figure 17B:
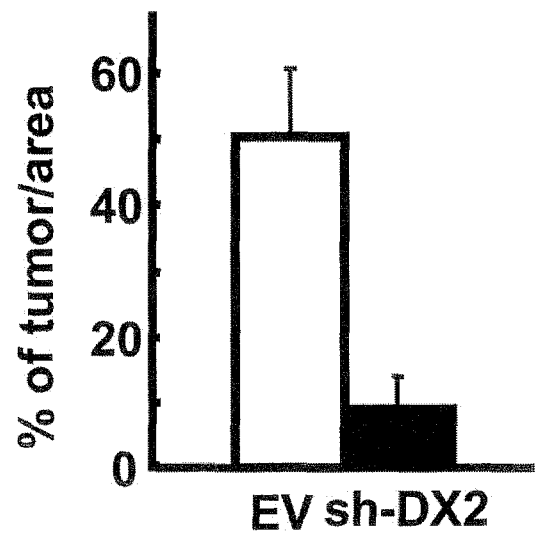
Figure 17C:
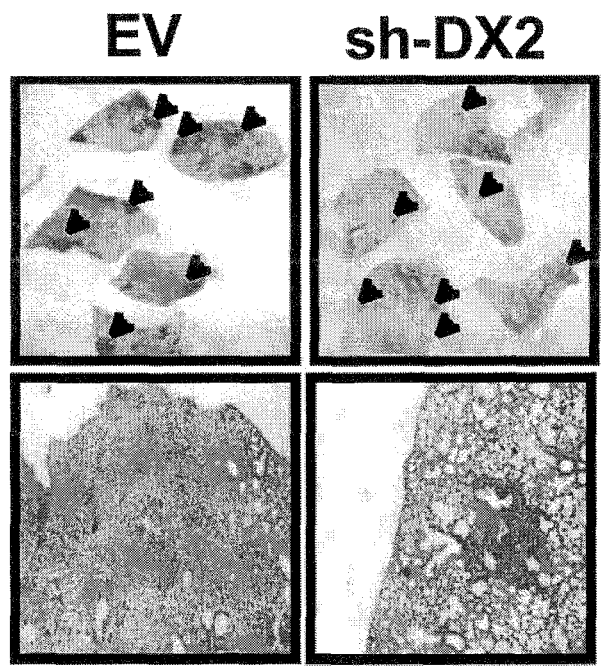
Figure 17D:
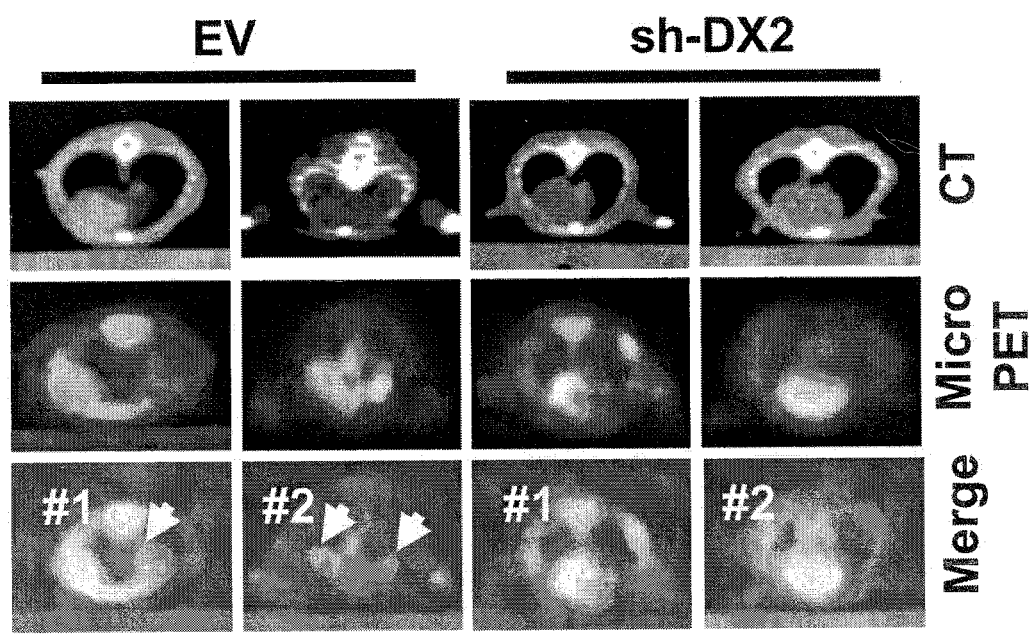
Figure 17E:
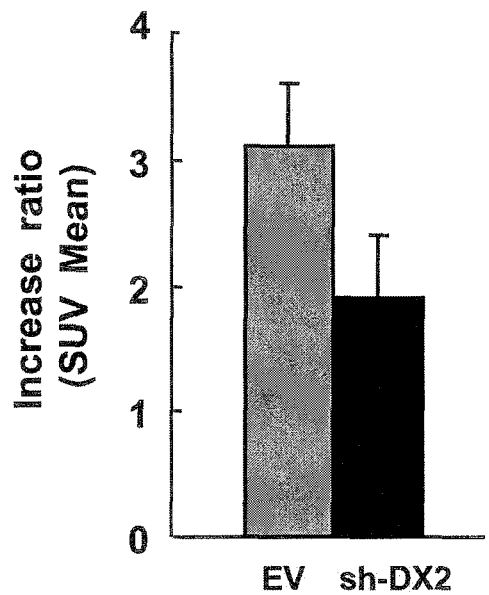

After confirming the efficient delivery of the DNA into lung alveoli, we delivered the sh-AIMP2-DX2-encoding plasmid DNA to the lungs of the mice twice a week from 6 weeks after the injection of BP. The mice were sacrificed 4 weeks after the administration of the DNA, and the tumor growth was monitored by morphological and histological analyses. The areas and histology of lung tumor region isolated from the sh-AIMP2-DX2-treated mice were compared with those of the control group. While the numbers of tumor nodules induced by BP were similar between the two groups of the mice (FIGS. 17a and c upper panel, arrow heads), the tumor area was reduced to about 10% of the total measured lung area in sh-AIMP2-DX2-treated lungs whereas about 50% remained as cancer region in the control group (FIGS. 17b and c lower panel). The lungs were selected from the EV and sh-DX2 plasmid-treated mice (n=2) and the tumor regions between the two groups were also compared by the combination of micro-PET and CT scanning analyses. For micro-PET analysis, we injected fluoro-2-deoxy-D-glucose (18FDG) into mice via tail vein and measured the FDG uptake rate in the tumors before and 12 weeks after DNA delivery. The FDG uptake rate in the sh-AIMP2-DX2 treated tumors increased less than 2 fold whereas more than 3 fold increase was observed in the control tumors (FIGS. 17d and e). In addition, we investigated whether the lung delivery of the sh-DX2 plasmid could improve the survival of the mice containing lung tumors. The survival rate of the sh-DX2 plasmid-treated group was significantly improved compared to the EV-treated group (FIG. 17f). Combined together, the inhibition of AIMP2-DX2 appears to suppress tumor growth and improve the survival of the lung tumor-containing mice.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. An isolated nucleic acid molecule encoding the AIMP2-DX2 protein having the amino acid sequence of SEQ ID NO: 2 or SEQ ID NO: 17.

2. The isolated nucleic acid molecule according to claim 1, wherein the nucleic acid molecule comprises a nucleotide sequence of SEQ ID NO:1 or SEQ ID NO: 16.

3. An expression vector which comprises the nucleic acid molecule of claim 1.

4. An isolated cell comprising the expression vector of claim 3.

* * * * *

SEQUENCE LISTING

<160> NUMBER OF SEQ ID NOS: 159

<210> SEQ ID NO 1
<211> LENGTH: 756
<212> TYPE: DNA
<213> ORGANISM: Homo sapiens
<220> FEATURE:
<221> NAME/KEY: CDS
<222> LOCATION: (1)..(753)
<223> OTHER INFORMATION: CDS of AIMP2-DX2-320 amino acids

<400> SEQUENCE: 1

```
atg ccg atg tac cag gta aag ccc tat cac ggg ggc ggc gcg cct ctc        48
Met Pro Met Tyr Gln Val Lys Pro Tyr His Gly Gly Gly Ala Pro Leu
 1               5                  10                  15 cgt gtg gag ctt ccc acc tgc atg tac cgg ctc ccc aac gtg cac ggc        96
Arg Val Glu Leu Pro Thr Cys Met Tyr Arg Leu Pro Asn Val His Gly
            20                  25                  30 agg agc tac ggc cca gcg ccg ggc gct ggc cac gtg cag gat tac ggg       144
Arg Ser Tyr Gly Pro Ala Pro Gly Ala Gly His Val Gln Asp Tyr Gly
        35                  40                  45 gcg ctg aaa gac atc gtg atc aac gca aac ccg gcc tcc cct ccc ctc       192
Ala Leu Lys Asp Ile Val Ile Asn Ala Asn Pro Ala Ser Pro Pro Leu
    50                  55                  60 tcc ctg ctt gtg ctg cac agg ctg ctc tgt gag cac ttc agg gtc ctg       240
Ser Leu Leu Val Leu His Arg Leu Leu Cys Glu His Phe Arg Val Leu
65                  70                  75                  80 tcc acg gtg cac acg cac tcc tcg gtc aag agc gtg cct gaa aac ctt       288
Ser Thr Val His Thr His Ser Ser Val Lys Ser Val Pro Glu Asn Leu
                85                  90                  95 ctc aag tgc ttt gga gaa cag aat aaa aaa cag ccc cgc caa gac tat       336
Leu Lys Cys Phe Gly Glu Gln Asn Lys Lys Gln Pro Arg Gln Asp Tyr
            100                 105                 110 cag ctg gga ttc act tta att tgg aag aat gtg ccg aag acg cag atg       384
Gln Leu Gly Phe Thr Leu Ile Trp Lys Asn Val Pro Lys Thr Gln Met
        115                 120                 125 aaa ttc agc atc cag acg atg tgc ccc atc gaa ggc gaa ggg aac att       432
Lys Phe Ser Ile Gln Thr Met Cys Pro Ile Glu Gly Glu Gly Asn Ile
    130                 135                 140 gca cgt ttc ttg ttc tct ctg ttt ggc cag aag cat aat gct gtc aac       480
Ala Arg Phe Leu Phe Ser Leu Phe Gly Gln Lys His Asn Ala Val Asn
145                 150                 155                 160 gca acc ctt ata gat agc tgg gta gat att gcg att ttt cag tta aaa       528
Ala Thr Leu Ile Asp Ser Trp Val Asp Ile Ala Ile Phe Gln Leu Lys
                165                 170                 175 gag gga agc agt aaa gaa aaa gcc gct gtt ttc cgc tcc atg aac tct       576
Glu Gly Ser Ser Lys Glu Lys Ala Ala Val Phe Arg Ser Met Asn Ser
            180                 185                 190 gct ctt ggg aag agc cct tgg ctc gct ggg aat gaa ctc acc gta gca       624
Ala Leu Gly Lys Ser Pro Trp Leu Ala Gly Asn Glu Leu Thr Val Ala
        195                 200                 205 gac gtg gtg ctg tgg tct gta ctc cag cag atc gga ggc tgc agt gtg       672
Asp Val Val Leu Trp Ser Val Leu Gln Gln Ile Gly Gly Cys Ser Val
    210                 215                 220 aca gtg cca gcc aat gtg cag agg tgg atg agg tct tgt gaa aac ctg       720
Thr Val Pro Ala Asn Val Gln Arg Trp Met Arg Ser Cys Glu Asn Leu
225                 230                 235                 240 gct cct ttt aac acg gcc ctc aag ctc ctt aag tga                       756
Ala Pro Phe Asn Thr Ala Leu Lys Leu Leu Lys
                245                 250
```

```
<210> SEQ ID NO 2
<211> LENGTH: 251
<212> TYPE: PRT
<213> ORGANISM: Homo sapiens

<400> SEQUENCE: 2

Met Pro Met Tyr Gln Val Lys Pro Tyr His Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
65                  70                  75                  80

Ser Thr Val His Thr His Ser Ser Val Lys Ser Val Pro Glu Asn Leu
                85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
    210                 215                 220

Thr Val Pro Ala Asn Val Gln Arg Trp Met Arg Ser Cys Glu Asn Leu
225                 230                 235                 240

Ala Pro Phe Asn Thr Ala Leu Lys Leu Leu Lys
                245                 250

<210> SEQ ID NO 3
<211> LENGTH: 20
<212> TYPE: DNA
<213> ORGANISM: Artificial Sequence
<220> FEATURE:
<223> OTHER INFORMATION: forward primer for exon 3-4

<400> SEQUENCE: 3
agtgctttgg agaacagaat                                            20

<210> SEQ ID NO 4
<211> LENGTH: 20
<212> TYPE: DNA
<213> ORGANISM: Artificial Sequence
<220> FEATURE:
<223> OTHER INFORMATION: reverse primer for exon 3-4

<400> SEQUENCE: 4
aagagcagag ttcatggagc                                            20
```

```
<210> SEQ ID NO 5
<211> LENGTH: 20
<212> TYPE: DNA
<213> ORGANISM: Artificial Sequence
<220> FEATURE:
<223> OTHER INFORMATION: forward primer for exon 1-3

<400> SEQUENCE: 5
tctgacggtt tctgagcgtt                                                    20

<210> SEQ ID NO 6
<211> LENGTH: 20
<212> TYPE: DNA
<213> ORGANISM: Artificial Sequence
<220> FEATURE:
<223> OTHER INFORMATION: reverse primer for exon 1-3

<400> SEQUENCE: 6
aagtgaatcc cagctgatag                                                    20

<210> SEQ ID NO 7
<211> LENGTH: 21
<212> TYPE: DNA
<213> ORGANISM: Artificial Sequence
<220> FEATURE:
<223> OTHER INFORMATION: forward primer for AIMP2-DX2

<400> SEQUENCE: 7
tgctttggtt ctgccatgcc g                                                  21

<210> SEQ ID NO 8
<211> LENGTH: 21
<212> TYPE: DNA
<213> ORGANISM: Artificial Sequence
<220> FEATURE:
<223> OTHER INFORMATION: reverse primer for AIMP2-DX2

<400> SEQUENCE: 8
cgtaatcctg cacgtggcca g                                                  21

<210> SEQ ID NO 9
<211> LENGTH: 54
<212> TYPE: DNA
<213> ORGANISM: Artificial Sequence
<220> FEATURE:
<223> OTHER INFORMATION: si-AIMP2-DX2 #3 coding nucleic acid sequence 1

<400> SEQUENCE: 9
tcgaggccac gtgcaggtta cgggagtagg ccgtaatcct gcacgtggcc tttt              54

<210> SEQ ID NO 10
<211> LENGTH: 55
<212> TYPE: DNA
<213> ORGANISM: Artificial Sequence
<220> FEATURE:
<223> OTHER INFORMATION: si-AIMP2-DX2 #3 coding nucleic acid sequence 2

<400> SEQUENCE: 10
ctagaaaagg ccacgtgcag gattacggca gactcccgta atcctgcacg tggcc             55

<210> SEQ ID NO 11
<211> LENGTH: 58
<212> TYPE: DNA
<213> ORGANISM: Artificial Sequence
<220> FEATURE:
<223> OTHER INFORMATION: si-AIMP2-DX2 #4 coding nucleic acid sequence 1
```

-continued

<400> SEQUENCE: 11
tcgagctggc cacgtgcagg attacgagta ctggtaatcc tgcacgtggc cagcttt    58

<210> SEQ ID NO 12
<211> LENGTH: 58
<212> TYPE: DNA
<213> ORGANISM: Artificial Sequence
<220> FEATURE:
<223> OTHER INFORMATION: si-AIMP2-DX2 #4 coding nucleic acid sequence 2

<400> SEQUENCE: 12
ctagaaaagc tggccacgtg caggattacc agtactcgta atcctgcacg tggccagc    58

<210> SEQ ID NO 13
<211> LENGTH: 56
<212> TYPE: DNA
<213> ORGANISM: Artificial Sequence
<220> FEATURE:
<223> OTHER INFORMATION: si-AIMP2-DX2 #5 coding nucleic acid sequence 1

<400> SEQUENCE: 13
tcgacacgtg caggattacg ggcgagtac tggccccgta atcctgcacg tgtttt    56

<210> SEQ ID NO 14
<211> LENGTH: 56
<212> TYPE: DNA
<213> ORGANISM: Artificial Sequence
<220> FEATURE:
<223> OTHER INFORMATION: si-AIMP2-DX2 #5 coding nucleic acid sequence 2

<400> SEQUENCE: 14
ctagaaaaca cgtgcaggat tacggggcca gtactcgccc cgtaatcctg cacgtg    56

<210> SEQ ID NO 15
<211> LENGTH: 15
<212> TYPE: DNA
<213> ORGANISM: Artificial Sequence
<220> FEATURE:
<223> OTHER INFORMATION: AIMP2-specific RT primer

<400> SEQUENCE: 15
cagcaccacg tctgc    15

<210> SEQ ID NO 16
<211> LENGTH: 729
<212> TYPE: DNA
<213> ORGANISM: Homo sapiens
<220> FEATURE:
<221> NAME/KEY: CDS
<222> LOCATION: (1)..(729)
<223> OTHER INFORMATION: CDS of AIMP2-DX2-312 amino acid

<400> SEQUENCE: 16

```
atg ccg atg tac cag gta aag ccc tat cac ggg ggc ggc gcg cct ctc     48
Met Pro Met Tyr Gln Val Lys Pro Tyr His Gly Gly Gly Ala Pro Leu
1               5                   10                  15 cgt gtg gag ctt ccc acc tgc atg tac cgg ctc ccc aac gtg cac ggc     96
Arg Val Glu Leu Pro Thr Cys Met Tyr Arg Leu Pro Asn Val His Gly
            20                  25                  30 agg agc tac ggc cca gcg ccg ggc gct ggc cac gtg cag gat tac ggg    144
Arg Ser Tyr Gly Pro Ala Pro Gly Ala Gly His Val Gln Asp Tyr Gly
        35                  40                  45 gcg ctg aaa gac atc gtg atc aac gca aac ccg gcc tcc cct ccc ctc    192
Ala Leu Lys Asp Ile Val Ile Asn Ala Asn Pro Ala Ser Pro Pro Leu
    50                  55                  60
```

```
tcc ctg ctt gtg ctg cac agg ctg ctc tgt gag cac ttc agg gtc ctg      240
Ser Leu Leu Val Leu His Arg Leu Leu Cys Glu His Phe Arg Val Leu
 65                  70                  75                  80 tcc acg gtg cac acg cac tcc tcg gtc aag agc gtc cct gaa aac ctt      288
Ser Thr Val His Thr His Ser Ser Val Lys Ser Val Pro Glu Asn Leu
                 85                  90                  95 ctc aag tgc ttt gga gaa cag aat aaa aaa cag ccc cgc caa gac tat      336
Leu Lys Cys Phe Gly Glu Gln Asn Lys Lys Gln Pro Arg Gln Asp Tyr
            100                 105                 110 cag ctg gga ttc act tta att tgg aag aat gtg ccg aag acg cag atg      384
Gln Leu Gly Phe Thr Leu Ile Trp Lys Asn Val Pro Lys Thr Gln Met
        115                 120                 125 aaa ttc agc atc cag acg atg tgc ccc atc gaa ggc gaa ggg aac att      432
Lys Phe Ser Ile Gln Thr Met Cys Pro Ile Glu Gly Glu Gly Asn Ile
130                 135                 140 gca cgt ttc ttg ttc tct ctg ttt ggc cag aag cat aat gct gtc aac      480
Ala Arg Phe Leu Phe Ser Leu Phe Gly Gln Lys His Asn Ala Val Asn
145                 150                 155                 160 gca acc ctt ata gat agc tgg gta gat att gcg att ttt cag tta aaa      528
Ala Thr Leu Ile Asp Ser Trp Val Asp Ile Ala Ile Phe Gln Leu Lys
                165                 170                 175 gag gga agc agt aaa gaa aaa gcc gct gtt ttc cgc tcc atg aac tct      576
Glu Gly Ser Ser Lys Glu Lys Ala Ala Val Phe Arg Ser Met Asn Ser
            180                 185                 190 gct ctt ggg aag agc cct tgg ctc gct ggg aat gaa ctc acc gta gca      624
Ala Leu Gly Lys Ser Pro Trp Leu Ala Gly Asn Glu Leu Thr Val Ala
        195                 200                 205 gac gtg gtg ctg tgg tct gta ctc cag cag atc gga ggc tgc agt gtg      672
Asp Val Val Leu Trp Ser Val Leu Gln Gln Ile Gly Gly Cys Ser Val
210                 215                 220 aca gtg cca gcc aat gtg cag agg tgg atg agg tct tgt gaa aac ctg      720
Thr Val Pro Ala Asn Val Gln Arg Trp Met Arg Ser Cys Glu Asn Leu
225                 230                 235                 240 gct cct ttt                                                          729
Ala Pro Phe <210> SEQ ID NO 17
<211> LENGTH: 243
<212> TYPE: PRT
<213> ORGANISM: Homo sapiens

<400> SEQUENCE: 17

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Asp Tyr Gly
        35                  40                  45

Ala Leu Lys Asp Ile Val Ile Asn Ala Asn Pro Ala Ser Pro Pro Leu
    50                  55                  60

Ser Leu Leu Val Leu His Arg Leu Leu Cys Glu His Phe Arg Val Leu
65                  70                  75                  80

Ser Thr Val His Thr His Ser Ser Val Lys Ser Val Pro Glu Asn Leu
                85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
```

```
              130                 135                 140
Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
    210                 215                 220

Thr Val Pro Ala Asn Val Gln Arg Trp Met Arg Ser Cys Glu Asn Leu
225                 230                 235                 240

Ala Pro Phe

<210> SEQ ID NO 18
<211> LENGTH: 58
<212> TYPE: DNA
<213> ORGANISM: Artificial Sequence
<220> FEATURE:
<223> OTHER INFORMATION: si-RNA target sequence

<400> SEQUENCE: 18
tcgagctggc cacgtgcagg attacgagta ctggtaatcc tgcacgtggc cagcttttt      58

<210> SEQ ID NO 19
<211> LENGTH: 25
<212> TYPE: DNA
<213> ORGANISM: Artificial Sequence
<220> FEATURE:
<223> OTHER INFORMATION: AIMP2-F forward Quantitative PCR primer

<400> SEQUENCE: 19
ctccaagatg attcaaacac cagat                                           25

<210> SEQ ID NO 20
<211> LENGTH: 20
<212> TYPE: DNA
<213> ORGANISM: Artificial Sequence
<220> FEATURE:
<223> OTHER INFORMATION: AIMP2-F reverse Quantitative PCR primer

<400> SEQUENCE: 20
ccgtaatcct tcccaagcac                                                 20

<210> SEQ ID NO 21
<211> LENGTH: 18
<212> TYPE: DNA
<213> ORGANISM: Artificial Sequence
<220> FEATURE:
<223> OTHER INFORMATION: AIMP2-DX2 forward Quantitative PCR primer

<400> SEQUENCE: 21
gccacgtgca ggattacg                                                   18

<210> SEQ ID NO 22
<211> LENGTH: 18
<212> TYPE: DNA
<213> ORGANISM: Artificial Sequence
<220> FEATURE:
<223> OTHER INFORMATION: AIMP2-DX2 reverse Quantitative PCR primer

<400> SEQUENCE: 22
```

```
tgcaccgtgg acaggacc                                                    18

<210> SEQ ID NO 23
<211> LENGTH: 26
<212> TYPE: DNA
<213> ORGANISM: Artificial Sequence
<220> FEATURE:
<223> OTHER INFORMATION: PAPOLA forward Quantitative PCR primer

<400> SEQUENCE: 23 aaacttttg aagctccaaa cttctt                                            26

<210> SEQ ID NO 24
<211> LENGTH: 18
<212> TYPE: DNA
<213> ORGANISM: Artificial Sequence
<220> FEATURE:
<223> OTHER INFORMATION: PAPOLA reverse Quantitative PCR primer

<400> SEQUENCE: 24
caccaagccc acccattc                                                    18

<210> SEQ ID NO 25
<211> LENGTH: 25
<212> TYPE: RNA
<213> ORGANISM: Artificial Sequence
<220> FEATURE:
<223> OTHER INFORMATION: siRNA of AIMP2-F

<400> SEQUENCE: 25
agucuaaccu gucucugcaa gcucu                                            25

<210> SEQ ID NO 26
<211> LENGTH: 58
<212> TYPE: DNA
<213> ORGANISM: Artificial Sequence
<220> FEATURE:
<223> OTHER INFORMATION: shRNA sequence of AIMP2-DX2

<400> SEQUENCE: 26
tcgagctggc cacgtgcagg attacgagta ctggtaatcc tgcacgtggc cagctttt        58

<210> SEQ ID NO 27
<211> LENGTH: 19
<212> TYPE: RNA
<213> ORGANISM: Artificial Sequence
<220> FEATURE:
<223> OTHER INFORMATION: AIMP2-DX2 siRNA 19mer #1

<400> SEQUENCE: 27
cuggccacgu gcaggauua                                                   19

<210> SEQ ID NO 28
<211> LENGTH: 19
<212> TYPE: RNA
<213> ORGANISM: Artificial Sequence
<220> FEATURE:
<223> OTHER INFORMATION: AIMP2-DX2 siRNA of 19mer #2

<400> SEQUENCE: 28
uggccacgug caggauuac                                                   19

<210> SEQ ID NO 29
<211> LENGTH: 19
<212> TYPE: RNA
<213> ORGANISM: Artificial Sequence
<220> FEATURE:
```

```
<223> OTHER INFORMATION: AIMP2-DX2 siRNA of 19mer #3

<400> SEQUENCE: 29
ggccacgugc aggauuacg                                              19

<210> SEQ ID NO 30
<211> LENGTH: 19
<212> TYPE: RNA
<213> ORGANISM: Artificial Sequence
<220> FEATURE:
<223> OTHER INFORMATION: 19mer of AIMP2-DX2 siRNA #4

<400> SEQUENCE: 30
gccacgugca ggauuacgg                                              19

<210> SEQ ID NO 31
<211> LENGTH: 19
<212> TYPE: RNA
<213> ORGANISM: Artificial Sequence
<220> FEATURE:
<223> OTHER INFORMATION: 19mer of AIMP2-DX2 siRNA #5

<400> SEQUENCE: 31
ccacgugcag gauuacggg                                              19

<210> SEQ ID NO 32
<211> LENGTH: 19
<212> TYPE: RNA
<213> ORGANISM: Artificial Sequence
<220> FEATURE:
<223> OTHER INFORMATION: 19mer of AIMP2-DX2 siRNA #6

<400> SEQUENCE: 32
cacgugcagg auuacgggg                                              19

<210> SEQ ID NO 33
<211> LENGTH: 19
<212> TYPE: RNA
<213> ORGANISM: Artificial Sequence
<220> FEATURE:
<223> OTHER INFORMATION: 19mer of AIMP2-DX2 siRNA #7

<400> SEQUENCE: 33
acgugcagga uuacggggc                                              19

<210> SEQ ID NO 34
<211> LENGTH: 19
<212> TYPE: RNA
<213> ORGANISM: Artificial Sequence
<220> FEATURE:
<223> OTHER INFORMATION: 19mer of AIMP2-DX2 siRNA #8

<400> SEQUENCE: 34
cgugcaggau uacggggcg                                              19

<210> SEQ ID NO 35
<211> LENGTH: 19
<212> TYPE: RNA
<213> ORGANISM: Artificial Sequence
<220> FEATURE:
<223> OTHER INFORMATION: 19mer of AIMP2-DX2 siRNA #8

<400> SEQUENCE: 35
cgugcaggau uacggggcg                                              19

<210> SEQ ID NO 36
```

```
<211> LENGTH: 19
<212> TYPE: RNA
<213> ORGANISM: Artificial Sequence
<220> FEATURE:
<223> OTHER INFORMATION: 19mer of AIMP2-DX2 siRNA #9

<400> SEQUENCE: 36
gugcaggauu acggggcgc                                                   19

<210> SEQ ID NO 37
<211> LENGTH: 19
<212> TYPE: RNA
<213> ORGANISM: Artificial Sequence
<220> FEATURE:
<223> OTHER INFORMATION: 19mer of AIMP2-DX2 siRNA #10

<400> SEQUENCE: 37
ugcaggauua cggggcgcu                                                   19

<210> SEQ ID NO 38
<211> LENGTH: 20
<212> TYPE: RNA
<213> ORGANISM: Artificial Sequence
<220> FEATURE:
<223> OTHER INFORMATION: 20mer of AIMP2-DX2 siRNA #1

<400> SEQUENCE: 38
gcuggccacg ugcaggauua                                                  20

<210> SEQ ID NO 39
<211> LENGTH: 20
<212> TYPE: RNA
<213> ORGANISM: Artificial Sequence
<220> FEATURE:
<223> OTHER INFORMATION: 20mer of AIMP2-DX2 siRNA #2

<400> SEQUENCE: 39
cuggccacgu gcaggauuac                                                  20

<210> SEQ ID NO 40
<211> LENGTH: 20
<212> TYPE: RNA
<213> ORGANISM: Artificial Sequence
<220> FEATURE:
<223> OTHER INFORMATION: 20mer of AIMP2-DX2 siRNA #3

<400> SEQUENCE: 40
uggccacgug caggauuacg                                                  20

<210> SEQ ID NO 41
<211> LENGTH: 20
<212> TYPE: RNA
<213> ORGANISM: Artificial Sequence
<220> FEATURE:
<223> OTHER INFORMATION: 20mer of AIMP2-DX2 siRNA #4

<400> SEQUENCE: 41
ggccacgugc aggauuacgg                                                  20

<210> SEQ ID NO 42
<211> LENGTH: 20
<212> TYPE: RNA
<213> ORGANISM: Artificial Sequence
<220> FEATURE:
<223> OTHER INFORMATION: 20mer of AIMP2-DX2 siRNA #5

<400> SEQUENCE: 42
```

```
gccacgugca ggauuacggg                                              20

<210> SEQ ID NO 43
<211> LENGTH: 20
<212> TYPE: RNA
<213> ORGANISM: Artificial Sequence
<220> FEATURE:
<223> OTHER INFORMATION: 20mer of AIMP2-DX2 siRNA #6

<400> SEQUENCE: 43
ccacgugcag gauuacgggg                                              20

<210> SEQ ID NO 44
<211> LENGTH: 20
<212> TYPE: RNA
<213> ORGANISM: Artificial Sequence
<220> FEATURE:
<223> OTHER INFORMATION: 20mer of AIMP2-DX2 siRNA #7

<400> SEQUENCE: 44
cacgugcagg auuacggggc                                              20

<210> SEQ ID NO 45
<211> LENGTH: 20
<212> TYPE: RNA
<213> ORGANISM: Artificial Sequence
<220> FEATURE:
<223> OTHER INFORMATION: 20mer of AIMP2-DX2 siRNA #8

<400> SEQUENCE: 45
acgugcagga uuacggggcg                                              20

<210> SEQ ID NO 46
<211> LENGTH: 20
<212> TYPE: RNA
<213> ORGANISM: Artificial Sequence
<220> FEATURE:
<223> OTHER INFORMATION: 20mer of AIMP2-DX2 siRNA #9

<400> SEQUENCE: 46
cgugcaggau uacggggcgc                                              20

<210> SEQ ID NO 47
<211> LENGTH: 20
<212> TYPE: RNA
<213> ORGANISM: Artificial Sequence
<220> FEATURE:
<223> OTHER INFORMATION: 20mer of AIMP2-DX2 siRNA #10

<400> SEQUENCE: 47
gugcaggauu acggggcgcu                                              20

<210> SEQ ID NO 48
<211> LENGTH: 20
<212> TYPE: RNA
<213> ORGANISM: Artificial Sequence
<220> FEATURE:
<223> OTHER INFORMATION: 20mer of AIMP2-DX2 siRNA #11

<400> SEQUENCE: 48
ugcaggauua cggggcgcug                                              20

<210> SEQ ID NO 49
<211> LENGTH: 21
<212> TYPE: RNA
<213> ORGANISM: Artificial Sequence
<220> FEATURE:
```

<223> OTHER INFORMATION: 21mer of AIMP2-DX2 siRNA #1

<400> SEQUENCE: 49
cgcuggccac gugcaggauu a                                              21

<210> SEQ ID NO 50
<211> LENGTH: 21
<212> TYPE: RNA
<213> ORGANISM: Artificial Sequence
<220> FEATURE:
<223> OTHER INFORMATION: 21mer of AIMP2-DX2 siRNA #2

<400> SEQUENCE: 50
gcuggccacg ugcaggauua c                                              21

<210> SEQ ID NO 51
<211> LENGTH: 21
<212> TYPE: RNA
<213> ORGANISM: Artificial Sequence
<220> FEATURE:
<223> OTHER INFORMATION: 21mer of AIMP2-DX2 siRNA #3

<400> SEQUENCE: 51
cuggccacgu gcaggauuac g                                              21

<210> SEQ ID NO 52
<211> LENGTH: 21
<212> TYPE: RNA
<213> ORGANISM: Artificial Sequence
<220> FEATURE:
<223> OTHER INFORMATION: 21mer of AIMP2-DX2 siRNA #4

<400> SEQUENCE: 52
uggccacgug caggauuacg g                                              21

<210> SEQ ID NO 53
<211> LENGTH: 21
<212> TYPE: RNA
<213> ORGANISM: Artificial Sequence
<220> FEATURE:
<223> OTHER INFORMATION: 21mer of AIMP2-DX2 siRNA #5

<400> SEQUENCE: 53
ggccacgugc aggauuacgg g                                              21

<210> SEQ ID NO 54
<211> LENGTH: 21
<212> TYPE: RNA
<213> ORGANISM: Artificial Sequence
<220> FEATURE:
<223> OTHER INFORMATION: 21mer of AIMP2-DX2 siRNA #6

<400> SEQUENCE: 54
gccacgugca ggauuacggg g                                              21

<210> SEQ ID NO 55
<211> LENGTH: 21
<212> TYPE: RNA
<213> ORGANISM: Artificial Sequence
<220> FEATURE:
<223> OTHER INFORMATION: 21mer of AIMP2-DX2 siRNA #7

<400> SEQUENCE: 55
ccacgugcag gauuacgggg c                                              21

<210> SEQ ID NO 56

```
<211> LENGTH: 21
<212> TYPE: RNA
<213> ORGANISM: Artificial Sequence
<220> FEATURE:
<223> OTHER INFORMATION: 21mer of AIMP2-DX2 siRNA #8

<400> SEQUENCE: 56
cacgugcagg auuacggggc g                                                 21

<210> SEQ ID NO 57
<211> LENGTH: 21
<212> TYPE: RNA
<213> ORGANISM: Artificial Sequence
<220> FEATURE:
<223> OTHER INFORMATION: 21mer of AIMP2-DX2 siRNA #9

<400> SEQUENCE: 57
acgugcagga uuacggggcg c                                                 21

<210> SEQ ID NO 58
<211> LENGTH: 21
<212> TYPE: RNA
<213> ORGANISM: Artificial Sequence
<220> FEATURE:
<223> OTHER INFORMATION: 21mer of AIMP2-DX2 siRNA #10

<400> SEQUENCE: 58
cgugcaggau uacggggcgc u                                                 21

<210> SEQ ID NO 59
<211> LENGTH: 21
<212> TYPE: RNA
<213> ORGANISM: Artificial Sequence
<220> FEATURE:
<223> OTHER INFORMATION: 21mer of AIMP2-DX2 siRNA #11

<400> SEQUENCE: 59
gugcaggauu acggggcgcu g                                                 21

<210> SEQ ID NO 60
<211> LENGTH: 21
<212> TYPE: RNA
<213> ORGANISM: Artificial Sequence
<220> FEATURE:
<223> OTHER INFORMATION: 21mer of AIMP2-DX2 siRNA #12

<400> SEQUENCE: 60
ugcaggauua cggggcgcug a                                                 21

<210> SEQ ID NO 61
<211> LENGTH: 22
<212> TYPE: RNA
<213> ORGANISM: Artificial Sequence
<220> FEATURE:
<223> OTHER INFORMATION: 22mer of AIMP2-DX2 siRNA #1

<400> SEQUENCE: 61
gcgcuggcca cgugcaggau ua                                                22

<210> SEQ ID NO 62
<211> LENGTH: 22
<212> TYPE: RNA
<213> ORGANISM: Artificial Sequence
<220> FEATURE:
<223> OTHER INFORMATION: 22mer of AIMP2-DX2 siRNA #2

<400> SEQUENCE: 62
```

-continued

```
cgcuggccac gugcaggauu ac                                              22

<210> SEQ ID NO 63
<211> LENGTH: 22
<212> TYPE: RNA
<213> ORGANISM: Artificial Sequence
<220> FEATURE:
<223> OTHER INFORMATION: 22mer of AIMP2-DX2 siRNA #3

<400> SEQUENCE: 63
gcuggccacg ugcaggauua cg                                              22

<210> SEQ ID NO 64
<211> LENGTH: 22
<212> TYPE: RNA
<213> ORGANISM: Artificial Sequence
<220> FEATURE:
<223> OTHER INFORMATION: 22mer of AIMP2-DX2 siRNA #4

<400> SEQUENCE: 64
cuggccacgu gcaggauuac gg                                              22

<210> SEQ ID NO 65
<211> LENGTH: 22
<212> TYPE: RNA
<213> ORGANISM: Artificial Sequence
<220> FEATURE:
<223> OTHER INFORMATION: 22mer of AIMP2-DX2 siRNA #5

<400> SEQUENCE: 65
uggccacgug caggauuacg gg                                              22

<210> SEQ ID NO 66
<211> LENGTH: 22
<212> TYPE: RNA
<213> ORGANISM: Artificial Sequence
<220> FEATURE:
<223> OTHER INFORMATION: 22mer of AIMP2-DX2 siRNA #6

<400> SEQUENCE: 66
ggccacgugc aggauuacgg gg                                              22

<210> SEQ ID NO 67
<211> LENGTH: 22
<212> TYPE: RNA
<213> ORGANISM: Artificial Sequence
<220> FEATURE:
<223> OTHER INFORMATION: 22mer of AIMP2-DX2 siRNA #7

<400> SEQUENCE: 67
gccacgugca ggauuacggg gc                                              22

<210> SEQ ID NO 68
<211> LENGTH: 22
<212> TYPE: RNA
<213> ORGANISM: Artificial Sequence
<220> FEATURE:
<223> OTHER INFORMATION: 22mer of AIMP2-DX2 siRNA #8

<400> SEQUENCE: 68
ccacgugcag gauuacgggg cg                                              22

<210> SEQ ID NO 69
<211> LENGTH: 22
<212> TYPE: RNA
<213> ORGANISM: Artificial Sequence
<220> FEATURE:
```

```
<223> OTHER INFORMATION: 22mer of AIMP2-DX2 siRNA #9

<400> SEQUENCE: 69
cacgugcagg auuacggggc gc                                           22

<210> SEQ ID NO 70
<211> LENGTH: 22
<212> TYPE: RNA
<213> ORGANISM: Artificial Sequence
<220> FEATURE:
<223> OTHER INFORMATION: 22mer of AIMP2-DX2 siRNA #10

<400> SEQUENCE: 70
acgugcagga uuacggggcg cu                                           22

<210> SEQ ID NO 71
<211> LENGTH: 22
<212> TYPE: RNA
<213> ORGANISM: Artificial Sequence
<220> FEATURE:
<223> OTHER INFORMATION: 22mer of AIMP2-DX2 siRNA #10

<400> SEQUENCE: 71
acgugcagga uuacggggcg cu                                           22

<210> SEQ ID NO 72
<211> LENGTH: 22
<212> TYPE: RNA
<213> ORGANISM: Artificial Sequence
<220> FEATURE:
<223> OTHER INFORMATION: 22mer of AIMP2-DX2 siRNA #11

<400> SEQUENCE: 72
cgugcaggau uacggggcgc ug                                           22

<210> SEQ ID NO 73
<211> LENGTH: 22
<212> TYPE: RNA
<213> ORGANISM: Artificial Sequence
<220> FEATURE:
<223> OTHER INFORMATION: 22mer of AIMP2-DX2 siRNA #12

<400> SEQUENCE: 73
gugcaggauu acggggcgcu ga                                           22

<210> SEQ ID NO 74
<211> LENGTH: 22
<212> TYPE: RNA
<213> ORGANISM: Artificial Sequence
<220> FEATURE:
<223> OTHER INFORMATION: 22mer of AIMP2-DX2 siRNA #13

<400> SEQUENCE: 74
ugcaggauua cggggcgcug aa                                           22

<210> SEQ ID NO 75
<211> LENGTH: 23
<212> TYPE: RNA
<213> ORGANISM: Artificial Sequence
<220> FEATURE:
<223> OTHER INFORMATION: 23mer of AIMP2-DX2 siRNA #1

<400> SEQUENCE: 75
ggcgcuggcc acgugcagga uua                                          23

<210> SEQ ID NO 76
```

```
<211> LENGTH: 23
<212> TYPE: RNA
<213> ORGANISM: Artificial Sequence
<220> FEATURE:
<223> OTHER INFORMATION: 23mer of AIMP2-DX2 siRNA #2

<400> SEQUENCE: 76
gcgcuggcca cgugcaggau uac                                            23

<210> SEQ ID NO 77
<211> LENGTH: 23
<212> TYPE: RNA
<213> ORGANISM: Artificial Sequence
<220> FEATURE:
<223> OTHER INFORMATION: 23mer of AIMP2-DX2 siRNA #3

<400> SEQUENCE: 77
cgcuggccac gugcaggauu acg                                            23

<210> SEQ ID NO 78
<211> LENGTH: 23
<212> TYPE: RNA
<213> ORGANISM: Artificial Sequence
<220> FEATURE:
<223> OTHER INFORMATION: 23mer of AIMP2-DX2 siRNA #4

<400> SEQUENCE: 78
gcuggccacg ugcaggauua cgg                                            23

<210> SEQ ID NO 79
<211> LENGTH: 23
<212> TYPE: RNA
<213> ORGANISM: Artificial Sequence
<220> FEATURE:
<223> OTHER INFORMATION: 23mer of AIMP2-DX2 siRNA #5

<400> SEQUENCE: 79
cuggccacgu gcaggauuac ggg                                            23

<210> SEQ ID NO 80
<211> LENGTH: 23
<212> TYPE: RNA
<213> ORGANISM: Artificial Sequence
<220> FEATURE:
<223> OTHER INFORMATION: 23mer of AIMP2-DX2 siRNA #6

<400> SEQUENCE: 80
uggccacgug caggauuacg ggg                                            23

<210> SEQ ID NO 81
<211> LENGTH: 23
<212> TYPE: RNA
<213> ORGANISM: Artificial Sequence
<220> FEATURE:
<223> OTHER INFORMATION: 23mer of AIMP2-DX2 siRNA  #7

<400> SEQUENCE: 81
ggccacgugc aggauuacgg ggc                                            23

<210> SEQ ID NO 82
<211> LENGTH: 23
<212> TYPE: RNA
<213> ORGANISM: Artificial Sequence
<220> FEATURE:
<223> OTHER INFORMATION: 23mer of AIMP2-DX2 siRNA #8

<400> SEQUENCE: 82
```

```
gccacgugca ggauuacggg gcg                                              23

<210> SEQ ID NO 83
<211> LENGTH: 23
<212> TYPE: RNA
<213> ORGANISM: Artificial Sequence
<220> FEATURE:
<223> OTHER INFORMATION: 23mer of AIMP2-DX2 siRNA #9

<400> SEQUENCE: 83
ccacgugcag gauuacgggg cgc                                              23

<210> SEQ ID NO 84
<211> LENGTH: 23
<212> TYPE: RNA
<213> ORGANISM: Artificial Sequence
<220> FEATURE:
<223> OTHER INFORMATION: 23mer of AIMP2-DX2 siRNA #10

<400> SEQUENCE: 84
cacgugcagg auuacggggc gcu                                              23

<210> SEQ ID NO 85
<211> LENGTH: 23
<212> TYPE: RNA
<213> ORGANISM: Artificial Sequence
<220> FEATURE:
<223> OTHER INFORMATION: 23mer of AIMP2-DX2 siRNA #11

<400> SEQUENCE: 85
acgugcagga uuacggggcg cug                                              23

<210> SEQ ID NO 86
<211> LENGTH: 23
<212> TYPE: RNA
<213> ORGANISM: Artificial Sequence
<220> FEATURE:
<223> OTHER INFORMATION: 23mer of AIMP2-DX2 siRNA #12

<400> SEQUENCE: 86
cgugcaggau uacggggcgc uga                                              23

<210> SEQ ID NO 87
<211> LENGTH: 23
<212> TYPE: RNA
<213> ORGANISM: Artificial Sequence
<220> FEATURE:
<223> OTHER INFORMATION: 23mer of AIMP2-DX2 siRNA #13

<400> SEQUENCE: 87
gugcaggauu acggggcgcu gaa                                              23

<210> SEQ ID NO 88
<211> LENGTH: 23
<212> TYPE: RNA
<213> ORGANISM: Artificial Sequence
<220> FEATURE:
<223> OTHER INFORMATION: 23mer of AIMP2-DX2 siRNA #14

<400> SEQUENCE: 88
ugcaggauua cggggcgcug aaa                                              23

<210> SEQ ID NO 89
<211> LENGTH: 24
<212> TYPE: RNA
<213> ORGANISM: Artificial Sequence
<220> FEATURE:
```

<223> OTHER INFORMATION: 24mer of AIMP2-DX2 siRNA #1

<400> SEQUENCE: 89
gggcgcuggc cacgugcagg auua                                          24

<210> SEQ ID NO 90
<211> LENGTH: 24
<212> TYPE: RNA
<213> ORGANISM: Artificial Sequence
<220> FEATURE:
<223> OTHER INFORMATION: 24mer of AIMP2-DX2 siRNA #2

<400> SEQUENCE: 90
ggcgcuggcc acgugcagga uuac                                          24

<210> SEQ ID NO 91
<211> LENGTH: 24
<212> TYPE: RNA
<213> ORGANISM: Artificial Sequence
<220> FEATURE:
<223> OTHER INFORMATION: 24mer of AIMP2-DX2 siRNA #3

<400> SEQUENCE: 91
gcgcuggcca cgugcaggau uacg                                          24

<210> SEQ ID NO 92
<211> LENGTH: 24
<212> TYPE: RNA
<213> ORGANISM: Artificial Sequence
<220> FEATURE:
<223> OTHER INFORMATION: 24mer of AIMP2-DX2 siRNA #4

<400> SEQUENCE: 92
cgcuggccac gugcaggauu acgg                                          24

<210> SEQ ID NO 93
<211> LENGTH: 24
<212> TYPE: RNA
<213> ORGANISM: Artificial Sequence
<220> FEATURE:
<223> OTHER INFORMATION: 24mer of AIMP2-DX2 siRNA #5

<400> SEQUENCE: 93
gcuggccacg ugcaggauua cggg                                          24

<210> SEQ ID NO 94
<211> LENGTH: 24
<212> TYPE: RNA
<213> ORGANISM: Artificial Sequence
<220> FEATURE:
<223> OTHER INFORMATION: 24mer of AIMP2-DX2 siRNA #6

<400> SEQUENCE: 94
cuggccacgu gcaggauuac gggg                                          24

<210> SEQ ID NO 95
<211> LENGTH: 24
<212> TYPE: RNA
<213> ORGANISM: Artificial Sequence
<220> FEATURE:
<223> OTHER INFORMATION: 24mer of AIMP2-DX2 siRNA #7

<400> SEQUENCE: 95
uggccacgug caggauuacg gggc                                          24

<210> SEQ ID NO 96

```
<211> LENGTH: 24
<212> TYPE: RNA
<213> ORGANISM: Artificial Sequence
<220> FEATURE:
<223> OTHER INFORMATION: 24mer of AIMP2-DX2 siRNA #8

<400> SEQUENCE: 96
ggccacgugc aggauuacgg ggcg                                    24

<210> SEQ ID NO 97
<211> LENGTH: 24
<212> TYPE: RNA
<213> ORGANISM: Artificial Sequence
<220> FEATURE:
<223> OTHER INFORMATION: 24mer of AIMP2-DX2 siRNA #9

<400> SEQUENCE: 97
gccacgugca ggauuacggg gcgc                                    24

<210> SEQ ID NO 98
<211> LENGTH: 24
<212> TYPE: RNA
<213> ORGANISM: Artificial Sequence
<220> FEATURE:
<223> OTHER INFORMATION: 24mer of AIMP2-DX2 siRNA #10

<400> SEQUENCE: 98
ccacgugcag gauuacgggg cgcu                                    24

<210> SEQ ID NO 99
<211> LENGTH: 24
<212> TYPE: RNA
<213> ORGANISM: Artificial Sequence
<220> FEATURE:
<223> OTHER INFORMATION: 24mer of AIMP2-DX2 siRNA #11

<400> SEQUENCE: 99
cacgugcagg auuacggggc gcug                                    24

<210> SEQ ID NO 100
<211> LENGTH: 24
<212> TYPE: RNA
<213> ORGANISM: Artificial Sequence
<220> FEATURE:
<223> OTHER INFORMATION: 24mer of AIMP2-DX2 siRNA #12

<400> SEQUENCE: 100
acgugcagga uuacggggcg cuga                                    24

<210> SEQ ID NO 101
<211> LENGTH: 24
<212> TYPE: RNA
<213> ORGANISM: Artificial Sequence
<220> FEATURE:
<223> OTHER INFORMATION: 24mer of AIMP2-DX2 siRNA #13

<400> SEQUENCE: 101
cgugcaggau uacggggcgc ugaa                                    24

<210> SEQ ID NO 102
<211> LENGTH: 24
<212> TYPE: RNA
<213> ORGANISM: Artificial Sequence
<220> FEATURE:
<223> OTHER INFORMATION: 24mer of AIMP2-DX2 siRNA #14

<400> SEQUENCE: 102
```
gugcaggauu acggggcgcu gaaa                                            24

<210> SEQ ID NO 103
<211> LENGTH: 24
<212> TYPE: RNA
<213> ORGANISM: Artificial Sequence
<220> FEATURE:
<223> OTHER INFORMATION: 24mer of AIMP2-DX2 siRNA #15

<400> SEQUENCE: 103
ugcaggauua cggggcgcug aaag                                            24

<210> SEQ ID NO 104
<211> LENGTH: 25
<212> TYPE: RNA
<213> ORGANISM: Artificial Sequence
<220> FEATURE:
<223> OTHER INFORMATION: 25mer of AIMP2-DX2 siRNA #1

<400> SEQUENCE: 104
cgggcgcugg ccacgugcag gauua                                           25

<210> SEQ ID NO 105
<211> LENGTH: 25
<212> TYPE: RNA
<213> ORGANISM: Artificial Sequence
<220> FEATURE:
<223> OTHER INFORMATION: 25mer of AIMP2-DX2 siRNA #2

<400> SEQUENCE: 105
gggcgcuggc cacgugcagg auuac                                           25

<210> SEQ ID NO 106
<211> LENGTH: 25
<212> TYPE: RNA
<213> ORGANISM: Artificial Sequence
<220> FEATURE:
<223> OTHER INFORMATION: 25mer of AIMP2-DX2 siRNA #3

<400> SEQUENCE: 106
ggcgcuggcc acgugcagga uuacg                                           25

<210> SEQ ID NO 107
<211> LENGTH: 25
<212> TYPE: RNA
<213> ORGANISM: Artificial Sequence
<220> FEATURE:
<223> OTHER INFORMATION: 25mer of AIMP2-DX2 siRNA #4

<400> SEQUENCE: 107
gcgcuggcca cgugcaggau uacgg                                           25

<210> SEQ ID NO 108
<211> LENGTH: 25
<212> TYPE: RNA
<213> ORGANISM: Artificial Sequence
<220> FEATURE:
<223> OTHER INFORMATION: 25mer of AIMP2-DX2 siRNA #5

<400> SEQUENCE: 108
cgcuggccac gugcaggauu acggg                                           25

<210> SEQ ID NO 109
<211> LENGTH: 25
<212> TYPE: RNA
<213> ORGANISM: Artificial Sequence
<220> FEATURE:

<223> OTHER INFORMATION: 25mer of AIMP2-DX2 siRNA #6

<400> SEQUENCE: 109
gcuggccacg ugcaggauua cgggg         25

<210> SEQ ID NO 110
<211> LENGTH: 25
<212> TYPE: RNA
<213> ORGANISM: Artificial Sequence
<220> FEATURE:
<223> OTHER INFORMATION: 25mer of AIMP2-DX2 siRNA #7

<400> SEQUENCE: 110
cuggccacgu gcaggauuac ggggc         25

<210> SEQ ID NO 111
<211> LENGTH: 25
<212> TYPE: RNA
<213> ORGANISM: Artificial Sequence
<220> FEATURE:
<223> OTHER INFORMATION: 25mer of AIMP2-DX2 siRNA #8

<400> SEQUENCE: 111
uggccacgug caggauuacg gggcg         25

<210> SEQ ID NO 112
<211> LENGTH: 25
<212> TYPE: RNA
<213> ORGANISM: Artificial Sequence
<220> FEATURE:
<223> OTHER INFORMATION: 25mer of AIMP2-DX2 siRNA #9

<400> SEQUENCE: 112
ggccacgugc aggauuacgg ggcgc         25

<210> SEQ ID NO 113
<211> LENGTH: 25
<212> TYPE: RNA
<213> ORGANISM: Artificial Sequence
<220> FEATURE:
<223> OTHER INFORMATION: 25mer of AIMP2-DX2 siRNA #10

<400> SEQUENCE: 113
gccacgugca ggauuacggg gcgcu         25

<210> SEQ ID NO 114
<211> LENGTH: 25
<212> TYPE: RNA
<213> ORGANISM: Artificial Sequence
<220> FEATURE:
<223> OTHER INFORMATION: 25mer of AIMP2-DX2 siRNA #11

<400> SEQUENCE: 114
ccacgugcag gauuacgggg cgcug         25

<210> SEQ ID NO 115
<211> LENGTH: 25
<212> TYPE: RNA
<213> ORGANISM: Artificial Sequence
<220> FEATURE:
<223> OTHER INFORMATION: 25mer of AIMP2-DX2 siRNA #12

<400> SEQUENCE: 115
cacgugcagg auuacggggc gcuga         25

<210> SEQ ID NO 116

```
<211> LENGTH: 25
<212> TYPE: RNA
<213> ORGANISM: Artificial Sequence
<220> FEATURE:
<223> OTHER INFORMATION: 25mer of AIMP2-DX2 siRNA #13

<400> SEQUENCE: 116
acgugcagga uuacggggcg cugaa                                              25

<210> SEQ ID NO 117
<211> LENGTH: 25
<212> TYPE: RNA
<213> ORGANISM: Artificial Sequence
<220> FEATURE:
<223> OTHER INFORMATION: 25mer of AIMP2-DX2 siRNA #14

<400> SEQUENCE: 117
cgugcaggau uacggggcgc ugaaa                                              25

<210> SEQ ID NO 118
<211> LENGTH: 25
<212> TYPE: RNA
<213> ORGANISM: Artificial Sequence
<220> FEATURE:
<223> OTHER INFORMATION: 25mer of AIMP2-DX2 siRNA #15

<400> SEQUENCE: 118
gugcaggauu acggggcgcu gaaag                                              25

<210> SEQ ID NO 119
<211> LENGTH: 25
<212> TYPE: RNA
<213> ORGANISM: Artificial Sequence
<220> FEATURE:
<223> OTHER INFORMATION: 25mer of AIMP2-DX2 siRNA #16

<400> SEQUENCE: 119
ugcaggauua cggggcgcug aaaga                                              25

<210> SEQ ID NO 120
<211> LENGTH: 26
<212> TYPE: RNA
<213> ORGANISM: Artificial Sequence
<220> FEATURE:
<223> OTHER INFORMATION: 26mer of AIMP2-DX2 siRNA #1

<400> SEQUENCE: 120
ccgggcgcug gccacgugca ggauua                                             26

<210> SEQ ID NO 121
<211> LENGTH: 26
<212> TYPE: RNA
<213> ORGANISM: Artificial Sequence
<220> FEATURE:
<223> OTHER INFORMATION: 26mer of AIMP2-DX2 siRNA #2

<400> SEQUENCE: 121
cgggcgcugg ccacgugcag gauuac                                             26

<210> SEQ ID NO 122
<211> LENGTH: 26
<212> TYPE: RNA
<213> ORGANISM: Artificial Sequence
<220> FEATURE:
<223> OTHER INFORMATION: 26mer of AIMP2-DX2 siRNA #3

<400> SEQUENCE: 122
```
gggcgcuggc cacgugcagg auuacg                                              26

<210> SEQ ID NO 123
<211> LENGTH: 26
<212> TYPE: RNA
<213> ORGANISM: Artificial Sequence
<220> FEATURE:
<223> OTHER INFORMATION: 26mer of AIMP2-DX2 siRNA #4

<400> SEQUENCE: 123
ggcgcuggcc acgugcagga uuacgg                                              26

<210> SEQ ID NO 124
<211> LENGTH: 26
<212> TYPE: RNA
<213> ORGANISM: Artificial Sequence
<220> FEATURE:
<223> OTHER INFORMATION: 26mer of AIMP2-DX2 siRNA #5

<400> SEQUENCE: 124
gcgcuggcca cgugcaggau uacggg                                              26

<210> SEQ ID NO 125
<211> LENGTH: 26
<212> TYPE: RNA
<213> ORGANISM: Artificial Sequence
<220> FEATURE:
<223> OTHER INFORMATION: 26mer of AIMP2-DX2 siRNA #6

<400> SEQUENCE: 125
cgcuggccac gugcaggauu acgggg                                              26

<210> SEQ ID NO 126
<211> LENGTH: 26
<212> TYPE: RNA
<213> ORGANISM: Artificial Sequence
<220> FEATURE:
<223> OTHER INFORMATION: 26mer of AIMP2-DX2 siRNA #7

<400> SEQUENCE: 126
gcuggccacg ugcaggauua cggggc                                              26

<210> SEQ ID NO 127
<211> LENGTH: 26
<212> TYPE: RNA
<213> ORGANISM: Artificial Sequence
<220> FEATURE:
<223> OTHER INFORMATION: 26mer of AIMP2-DX2 siRNA #8

<400> SEQUENCE: 127
cuggccacgu gcaggauuac ggggcg                                              26

<210> SEQ ID NO 128
<211> LENGTH: 26
<212> TYPE: RNA
<213> ORGANISM: Artificial Sequence
<220> FEATURE:
<223> OTHER INFORMATION: 26mer of AIMP2-DX2 siRNA #9

<400> SEQUENCE: 128
uggccacgug caggauuacg gggcgc                                              26

<210> SEQ ID NO 129
<211> LENGTH: 26
<212> TYPE: RNA
<213> ORGANISM: Artificial Sequence
<220> FEATURE:

```
<223> OTHER INFORMATION: 26mer of AIMP2-DX2 siRNA #10

<400> SEQUENCE: 129
ggccacgugc aggauuacgg ggcgcu                                            26

<210> SEQ ID NO 130
<211> LENGTH: 26
<212> TYPE: RNA
<213> ORGANISM: Artificial Sequence
<220> FEATURE:
<223> OTHER INFORMATION: 26mer of AIMP2-DX2 siRNA #11

<400> SEQUENCE: 130
gccacgugca ggauuacggg gcgcug                                            26

<210> SEQ ID NO 131
<211> LENGTH: 26
<212> TYPE: RNA
<213> ORGANISM: Artificial Sequence
<220> FEATURE:
<223> OTHER INFORMATION: 26mer of AIMP2-DX2 siRNA #12

<400> SEQUENCE: 131
ccacgugcag gauuacgggg cgcuga                                            26

<210> SEQ ID NO 132
<211> LENGTH: 26
<212> TYPE: RNA
<213> ORGANISM: Artificial Sequence
<220> FEATURE:
<223> OTHER INFORMATION: 26mer of AIMP2-DX2 siRNA #13

<400> SEQUENCE: 132
cacgugcagg auuacggggc gcugaa                                            26

<210> SEQ ID NO 133
<211> LENGTH: 26
<212> TYPE: RNA
<213> ORGANISM: Artificial Sequence
<220> FEATURE:
<223> OTHER INFORMATION: 26mer of AIMP2-DX2 siRNA #14

<400> SEQUENCE: 133
acgugcagga uuacggggcg cugaaa                                            26

<210> SEQ ID NO 134
<211> LENGTH: 26
<212> TYPE: RNA
<213> ORGANISM: Artificial Sequence
<220> FEATURE:
<223> OTHER INFORMATION: 26mer of AIMP2-DX2 siRNA #15

<400> SEQUENCE: 134
cgugcaggau uacggggcgc ugaaag                                            26

<210> SEQ ID NO 135
<211> LENGTH: 26
<212> TYPE: RNA
<213> ORGANISM: Artificial Sequence
<220> FEATURE:
<223> OTHER INFORMATION: 26mer of AIMP2-DX2 siRNA #16

<400> SEQUENCE: 135
gugcaggauu acggggcgcu gaaaga                                            26

<210> SEQ ID NO 136
```

```
<211> LENGTH: 26
<212> TYPE: RNA
<213> ORGANISM: Artificial Sequence
<220> FEATURE:
<223> OTHER INFORMATION: 26mer of AIMP2-DX2 siRNA #17

<400> SEQUENCE: 136
ugcaggauua cggggcgcug aaagac                                          26

<210> SEQ ID NO 137
<211> LENGTH: 27
<212> TYPE: RNA
<213> ORGANISM: Artificial Sequence
<220> FEATURE:
<223> OTHER INFORMATION: 27mer of AIMP2-DX2 siRNA #1

<400> SEQUENCE: 137
gccgggcgcu ggccacgugc aggauua                                         27

<210> SEQ ID NO 138
<211> LENGTH: 27
<212> TYPE: RNA
<213> ORGANISM: Artificial Sequence
<220> FEATURE:
<223> OTHER INFORMATION: 27mer of AIMP2-DX2 siRNA #2

<400> SEQUENCE: 138
ccgggcgcug gccacgugca ggauuac                                         27

<210> SEQ ID NO 139
<211> LENGTH: 27
<212> TYPE: RNA
<213> ORGANISM: Artificial Sequence
<220> FEATURE:
<223> OTHER INFORMATION: 27mer of AIMP2-DX2 siRNA #3

<400> SEQUENCE: 139
cgggcgcugg ccacgugcag gauuacg                                         27

<210> SEQ ID NO 140
<211> LENGTH: 27
<212> TYPE: RNA
<213> ORGANISM: Artificial Sequence
<220> FEATURE:
<223> OTHER INFORMATION: 27mer of AIMP2-DX2 siRNA #4

<400> SEQUENCE: 140
gggcgcuggc cacgugcagg auuacgg                                         27

<210> SEQ ID NO 141
<211> LENGTH: 27
<212> TYPE: RNA
<213> ORGANISM: Artificial Sequence
<220> FEATURE:
<223> OTHER INFORMATION: 27mer of AIMP2-DX2 siRNA #5

<400> SEQUENCE: 141
ggcgcuggcc acgugcagga uuacggg                                         27

<210> SEQ ID NO 142
<211> LENGTH: 27
<212> TYPE: RNA
<213> ORGANISM: Artificial Sequence
<220> FEATURE:
<223> OTHER INFORMATION: 27mer of AIMP2-DX2 siRNA #6

<400> SEQUENCE: 142
```

-continued

```
gcgcuggcca cgugcaggau uacgggg                                              27

<210> SEQ ID NO 143
<211> LENGTH: 27
<212> TYPE: RNA
<213> ORGANISM: Artificial Sequence
<220> FEATURE:
<223> OTHER INFORMATION: 27mer of AIMP2-DX2 siRNA #7

<400> SEQUENCE: 143
cgcuggccac gugcaggauu acggggc                                              27

<210> SEQ ID NO 144
<211> LENGTH: 27
<212> TYPE: RNA
<213> ORGANISM: Artificial Sequence
<220> FEATURE:
<223> OTHER INFORMATION: 27mer of AIMP2-DX2 siRNA #8

<400> SEQUENCE: 144
gcuggccacg ugcaggauua cggggcg                                              27

<210> SEQ ID NO 145
<211> LENGTH: 27
<212> TYPE: RNA
<213> ORGANISM: Artificial Sequence
<220> FEATURE:
<223> OTHER INFORMATION: 27mer of AIMP2-DX2 siRNA #9

<400> SEQUENCE: 145
cuggccacgu gcaggauuac ggggcgc                                              27

<210> SEQ ID NO 146
<211> LENGTH: 27
<212> TYPE: RNA
<213> ORGANISM: Artificial Sequence
<220> FEATURE:
<223> OTHER INFORMATION: 27mer of AIMP2-DX2 siRNA #10

<400> SEQUENCE: 146
uggccacgug caggauuacg gggcgcu                                              27

<210> SEQ ID NO 147
<211> LENGTH: 27
<212> TYPE: RNA
<213> ORGANISM: Artificial Sequence
<220> FEATURE:
<223> OTHER INFORMATION: 27mer of AIMP2-DX2 siRNA #11

<400> SEQUENCE: 147
ggccacgugc aggauuacgg ggcgcug                                              27

<210> SEQ ID NO 148
<211> LENGTH: 27
<212> TYPE: RNA
<213> ORGANISM: Artificial Sequence
<220> FEATURE:
<223> OTHER INFORMATION: 27mer of AIMP2-DX2 siRNA #12

<400> SEQUENCE: 148
gccacgugca ggauuacggg gcgcuga                                              27

<210> SEQ ID NO 149
<211> LENGTH: 27
<212> TYPE: RNA
<213> ORGANISM: Artificial Sequence
<220> FEATURE:
```

```
<223> OTHER INFORMATION: 27mer of AIMP2-DX2 siRNA #13

<400> SEQUENCE: 149
ccacgugcag gauuacgggg cgcugaa                                      27

<210> SEQ ID NO 150
<211> LENGTH: 27
<212> TYPE: RNA
<213> ORGANISM: Artificial Sequence
<220> FEATURE:
<223> OTHER INFORMATION: 27mer of AIMP2-DX2 siRNA #14

<400> SEQUENCE: 150
cacgugcagg auuacggggc gcugaaa                                      27

<210> SEQ ID NO 151
<211> LENGTH: 27
<212> TYPE: RNA
<213> ORGANISM: Artificial Sequence
<220> FEATURE:
<223> OTHER INFORMATION: 27mer of AIMP2-DX2 siRNA #15

<400> SEQUENCE: 151
acgugcagga uuacggggcg cugaaag                                      27

<210> SEQ ID NO 152
<211> LENGTH: 27
<212> TYPE: RNA
<213> ORGANISM: Artificial Sequence
<220> FEATURE:
<223> OTHER INFORMATION: 27mer of AIMP2-DX2 siRNA #16

<400> SEQUENCE: 152
cgugcaggau uacggggcgc ugaaaga                                      27

<210> SEQ ID NO 153
<211> LENGTH: 27
<212> TYPE: RNA
<213> ORGANISM: Artificial Sequence
<220> FEATURE:
<223> OTHER INFORMATION: 27mer of AIMP2-DX2 siRNA #17

<400> SEQUENCE: 153
gugcaggauu acggggcgcu gaaagac                                      27

<210> SEQ ID NO 154
<211> LENGTH: 27
<212> TYPE: RNA
<213> ORGANISM: Artificial Sequence
<220> FEATURE:
<223> OTHER INFORMATION: 27mer of AIMP2-DX2 siRNA #18

<400> SEQUENCE: 154
ugcaggauua cggggcgcug aaagaca                                      27

<210> SEQ ID NO 155
<211> LENGTH: 57
<212> TYPE: DNA
<213> ORGANISM: Artificial Sequence
<220> FEATURE:
<223> OTHER INFORMATION: shRNA sequence of mouse AIMP2-DX2

<400> SEQUENCE: 155
tcgagcgggc cacgtgcagg actattcaag agatagtcct gcacgtggcc cgctttt     57

<210> SEQ ID NO 156
```

```
<211> LENGTH: 22
<212> TYPE: RNA
<213> ORGANISM: Artificial Sequence
<220> FEATURE:
<223> OTHER INFORMATION: mouse siRNA for AIMP2-DX2

<400> SEQUENCE: 156
gcgggccacg ugcaggacua uu                                            22

<210> SEQ ID NO 157
<211> LENGTH: 28
<212> TYPE: DNA
<213> ORGANISM: Artificial Sequence
<220> FEATURE:
<223> OTHER INFORMATION: AIMP2-F Quantitative PCR Probe

<400> SEQUENCE: 157
cattggtggt taaagtcgtg ggctcatc                                      28

<210> SEQ ID NO 158
<211> LENGTH: 23
<212> TYPE: DNA
<213> ORGANISM: Artificial Sequence
<220> FEATURE:
<223> OTHER INFORMATION: AIMP2-DX2 Quantitative PCR Probe

<400> SEQUENCE: 158
acatcgtgat caacgcaaac ccg                                           23

<210> SEQ ID NO 159
<211> LENGTH: 25
<212> TYPE: DNA
<213> ORGANISM: Artificial Sequence
<220> FEATURE:
<223> OTHER INFORMATION: PAPOLA Quantitative PCR Probe

<400> SEQUENCE: 159
aggcgttgtt tttctgttgg tgcac                                         25
```